US011220719B2

(12) United States Patent
Gao et al.

(10) Patent No.: US 11,220,719 B2
(45) Date of Patent: Jan. 11, 2022

(54) COMPOSITIONS AND METHODS FOR DETECTING OR QUANTIFYING HEPATITIS B VIRUS

(71) Applicant: Gen-Probe Incorporated, San Diego, CA (US)

(72) Inventors: Kui Gao, San Diego, CA (US); Jeffrey M. Linnen, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 70 days.

(21) Appl. No.: 16/672,224

(22) Filed: Nov. 1, 2019

(65) Prior Publication Data

US 2020/0063218 A1 Feb. 27, 2020

Related U.S. Application Data

(62) Division of application No. 15/816,036, filed on Nov. 17, 2017, now Pat. No. 10,508,313.

(60) Provisional application No. 62/424,956, filed on Nov. 21, 2016.

(51) Int. Cl.
*C12Q 1/70* (2006.01)
*C12Q 1/68* (2018.01)
*C12Q 1/686* (2018.01)
*C12Q 1/6851* (2018.01)

(52) U.S. Cl.
CPC ............ *C12Q 1/706* (2013.01); *C12Q 1/686* (2013.01); *C12Q 1/6851* (2013.01); *C12Q 2600/112* (2013.01); *C12Q 2600/156* (2013.01); *C12Q 2600/158* (2013.01); *C12Q 2600/16* (2013.01); *C12Q 2600/172* (2013.01)

(58) Field of Classification Search
CPC ..... C12Q 1/706; C12Q 2600/16; C12Q 1/686
See application file for complete search history.

(56) References Cited

U.S. PATENT DOCUMENTS

| 7,015,317 | B2 | 3/2006 | Mullen et al. | |
|---|---|---|---|---|
| 9,139,870 | B2 | 9/2015 | Nelson et al. | |
| 10,508,313 | B2 * | 12/2019 | Gao | C12Q 1/686 |
| 2003/0050470 | A1 | 3/2003 | An | |
| 2004/0023207 | A1 | 2/2004 | Polansky | |
| 2011/0081645 | A1 | 4/2011 | Linnen | |
| 2015/0307951 | A1 | 10/2015 | Schroder | |
| 2018/0155800 | A1 * | 6/2018 | Gao | C12Q 1/706 |
| 2020/0063218 | A1 * | 2/2020 | Gao | C12Q 1/706 |

FOREIGN PATENT DOCUMENTS

| AU | 2012202286 A1 * | 5/2012 | ............... C12Q 1/68 |
|---|---|---|---|
| AU | 2012202286 A1 | 5/2012 | |
| KR | 2012002263 | 1/2012 | |
| WO | WO 1996/022392 | 7/1996 | |
| WO | WO 2010/092595 A2 | 8/2010 | |
| WO | WO-2018094171 A1 * | 5/2018 | ............. C12Q 1/686 |

OTHER PUBLICATIONS

Okamoto et al. 1988. Typing hepatitis B virus by homology in nucleotide sequence: comparison of surface antigen subtypes. Journal of general Virology 69(10): 2575-2583. (Year: 1988).*
Muthukumar et al. 2008. Molecular tools for the detection and characterization of bacterial infections: a review. Laboratory Medicine 39(7):430-436. (Year: 2008).*
Wilhelm et al., 2006. Systematic comparison of the T7-IVT and SMART-based RNA preamplification techniques for DNA microarray experiments. Clinical chemistry, 52(6), pp. 1161-1167. (Year: 2006).*
Abe et al, 1999. Quantitation of hepatitis B virus genomic DNA by real-time detection PCR. Journal of clinical microbiology, 37(9), pp. 2899-2903. (Year: 1999).*
Sarrazin et al., 2000. Detection of residual hepatitis C virus RNA by transcription-mediated amplification in patients with complete virologic response according to polymerase chain reaction-based assays. Hepatology, 32(4), pp. 818-823. (Year: 2000).*
English translation of KR-2012-002263 by Hyun et al. (pub Jan. 5, 2012) (Year: 2012).*
Abbott Molecular Inc., "Abbott Real Time HBV," 26 pages (2010).
Chook, et al. "Universal Primers for Detection and Sequencing of Hepatitis B Virus Genomes across Genotypes A to G." *Journal of Clinical Microbiology*, 53(6): 1831-1835 (2015).
English Translation of KR2012-002263 by Hyun et al. (pub. Jan. 5, 2012).
Gen bank Accession No. GU078862—Hepatitis B virus isolate J 104 reverse transcriptase (P) gene, partial cds (submitted Oct. 2009, retrieved on Nov. 27, 2018 from http://www.ncbi.nlm.nih.gov/nuccore/GU078862). (2009).
Genbank Accession No. DQ899150—Hepatitis B virus isolate Colombia8, complete genome (submitted Aug. 2006, retrieved on Nov. 27, 2018 from http://www.ncbi.nlm.nih.gov/nuccore/DQ899150). (2006).
Genbank Accession No. FJ349240—Hepatitis B virus isolate C89, complete genome (submitted Oct. 2008, retrieved on Nov. 27, 2018 from http://www.ncbi.nlm.nih.gov/nuccore/FJ349240). (2008).
Genbank Accession No. FJ561039—Hepatitis B virus isolate S94 polymerase gene, partial cds; and S protein gene, complete cds (submitted Dec. 2008, retrieved on Nov. 27, 2018 from http://www.ncbi.nlm.nih.gov/nuccore/FJ561039). (2008).
Genbank Accession No. FJ709471—Hepatitis B virus isolate CHI 15 polymerase (P) and middle S protein (S) genes, partial cds (submitted Feb. 2009, retrieved on Nov. 27, 2018 from http://www.ncbi.nlm.nih.gov/nuccore/FJ709471 ). (2009).

(Continued)

*Primary Examiner* — Teresa E Strzelecka
*Assistant Examiner* — Olayinka A Oyeyemi
(74) *Attorney, Agent, or Firm* — McNeill Baur PLLC; Michael J. Gilly

(57) ABSTRACT

This disclosure provides oligomers, compositions, and kits for detecting and quantifying Hepatitis B virus (HBV), including different genotypes and variants thereof, and related methods and uses. In some embodiments, oligomers target the P and/or S open reading frames of HBV and are configured to provide substantially equivalent quantification of different genotypes and variants of HBV.

20 Claims, 15 Drawing Sheets

Specification includes a Sequence Listing.

(56) References Cited

OTHER PUBLICATIONS

Genbank Accession No. GQ922005—Hepatitis B virus isolate 282894, complete genome (submitted Sep. 2009, retrieved on Nov. 27, 2018 from http://www.ncbi.nlm.nih.gov/nuccore/GQ922005). (2009).
Genbank Accession No. KU679939—Hepatitis B virus isolate 083 WA Man, complete genome (submitted Feb. 2016, retrieved on Jan. 3, 2019 from http://www.ncbi.nlm.nih.gov/nuccore/KU679939). (2016).
Genbank Accession No. KX276834—Hepatitis B virus strain CH039, complete genome (submitted May 2016, retrieved on Dec. 17, 2018 from http://www.ncbi.nlm.nih.gov/nuccore/KX276834). (2016).
Gen-Probe Incorporated, "Procleix Ultrio Assay," (2012).
Hologic, "Aptima HBV Quant Assay," 37 pages (2015).
Hologic, "Aptima HBV Quant Assay," 5 pages, printed Mar. 10, 2016.
Huang et al., "Impact of Genetic Heterogeneity in Polymerase of Hepatitis B Virus on Dynamics of Viral Load and Hepatitis B Progression," PLOS 8(7): e70169 (2013).
Roche Molecular Systems, Inc., "cobas HBV Quantitative nucleic acid test for use on the cobas 6800/8800 systems," 42 pages (2015).
SantaLucia Jr, John. "Physical principles and visual-OMP software for optimal PCR design."PCR Primer Design. Humana Press: pp. 3-33. (2007).
Search Report and Written Opinion from PCT/US2017/062229, dated May 4, 2018, 16 pages.
Tong, et al. "New universal primers for genotyping and resistance detection of low HBV DNA levels." *Medicine*, 95:33(e4618), 7 pages (2016).

\* cited by examiner

```
Target Capture Oligomer 0707b(+)    -----GGGCTTTCCCCCACTGTTTGGCTTTTTTTAAAAAAAAAAAAAAAAAAAAAAAAAAAAAAAA
Target Capture Oligomer 733(+)      ------------------------------AGTTATATGGATGATGTGGTATTGGTTTAAAAAAA
----HBV Genotype Clones----
HBV Subtype A_adw_WHO Std_2         TCGTAGGGCTTTCCCCCACTGTTTGGCTTTCAGTTATATGGATGATGTGGTATTGGGGGCCAAGTC
HBV A calibrator insert (+) strand  TCGTAGGGCTTTCCCCCACTGTTTGGCTTTCAGTTATATGGATGATGTGGTATTGGGGGCCAAGTC
HBV B Clone digest (+) strand       TCGTAGGGCTTTCCCCCACTGTCTGGCTTTCAGTTATATGGATGATGTGGTATTGGGGGCCAAGTC
HBV C Clone digest (+) strand       TCGTAGGGCTTTCCCCCACTGTCTGGCTTTCAGTTATATGGATGATGTGGTATTGGTTTGGGGCCAAGTC
HBV C2 Clone digest (+) strand      TCGTAGGGCTTTCCCCCACTGTTTGGCTTTCAGTTATATGGATGATGTGGTATTGGGGGCCAAGTC
HBV D Clone digest (+) strand       TCGTAGGGCTTTCCCCCACTGTTTGGCTTTCAGTTATATGGATGATGTGGTATTGGGGGCCAAGTC
HBV E Clone digest (+) strand       TCGCCGGGCTTTCCCCCACTGTCTGGCTTTTAGTTATATGGATGATGTGGTATTGGGGGCCAAGTC
HBV F Clone digest (+) strand       GCGTAGGGCTTTCCCCCACTGTCTGGCTTTAGTTATTGGATGATCTGGTATTGGGGGCCAAATC
HBV G Clone digest (+) strand       TCGTAGGGCTTTCCCCCACTGTCTGGCTTTCAGCTATGTGGATGATGTGGTATTGGGGGCCAAATC
HBV H Clone digest (+) strand       GCGTAGGGCTTTCCCCCACTGTCTGGCTTTTAGTTATATGGATGATTGGTATTGGGGGCCAAGTC
```

Fig. 1A

| 1290 | ----TTGTTTGCTCGCAGCCGGTCTGGAGCg |
|---|---|
| A(1839) | GSNGY..........................NV |
| B(1152) | RCNGC.......A................NM |
| C(517)  | GCNGY.......A..........G..DM |
| D(159)  | GCNGC....................G..RA |
| E(136)  | GCNGC..........................RV |
| F(85)   | GCMGC....C....A.............RA |
| G(68)   | GCNGCC.......................DR |
| H(64)   | NNNNNNNNNNNNNNNNNNNNNNNNNNNNNN |
| I(59)   | GCVGC....C....A................R |
| J(27)   | GCAGCC...C.....................A |

Fig. 1B

| 1168 | ---GTCTGTGCCAAGTGTTTGCTGACGCTT |
|---|---|
| A(2283) | HNR.............................AA |
| B(846)  | CNR....C........................VA |
| C(335)  | CNR..................T..........AA |
| D(247)  | CNG....T........................AA |
| E(132)  | CNG....A........................AA |
| F(117)  | CDG.C...........................AA |
| G(65)   | NNNNNNNNNNNNNNNNNNNNNNNNNNNNNN |
| H(34)   | CWG....C....................T..RA |
| I(29)   | CMG....A........................AA |
| J(26)   | CHG..G.C........................AA |

Fig. 1C

```
NT7 oligomer 474-455(-)                    ------------------------------------   ------------------------------------
T7 oligomer 376-397(+)                     ------------------------------------   AATTTAATACGACTCACTATAGGGAGAGATGTGTCTGCGGCG
T7 oligomer 376-402(+)                     ------------------------------------   AATTTAATACGACTCACTATAGGGAGAGATGTGTCTGCGGCG
Probe oligomer 408-435(-)                  ------------------------------------   ------------------------------------
----HBV Genotype Clones----
HBV_Subtype_A_adw_WHO_Std_2                ACTCACCAACCTCCTGTCCTCCAATTTGTCCTGGTTATCGCTGGATGTGTCTGCGGCG
HBV_A calibrator insert(+)strand           ACTCACCAACCTCCTGTCCTCCAATTTGTCCTGGCTATCGCTGGATGTGTCTGCGGCG
HBV B Clone digest (+) strand              ACTCACCAACTTGTGTCCTCCGATTTGTCCTGGTTATCGCTGGATGTGTCTGCGGCG
HBV C Clone digest (+) strand              ACTCACCAACCTCTTGTCCTTGTCCTCCAATTTGTCCTGGCTATCGCTGGATGTGTCTGCGGCG
HBV C2 Clone digest (+) strand             ACTCACCAACCTCCTTGTCCTCCAATTTGTCCTGGCTATCGTTGGATGTGTCTGCGGCG
HBV D Clone digest (+) strand              ACTCACCAACCTCCTGTCCTCCAACTTGTCCTGGTTATCGCTGGATGTGTCTGCGGCG
HBV E Clone digest (+) strand              ACTCACCAACCTCCTGTCCTCCAACTTGTCCTGGCTATCGCTGGATGTGTCTGCGGCG
HBV F Clone digest (+) strand              ACTTACCAACCTCCTGTCCTCCAACTTGTCCTGGCTATCGCTGGATGTGTCTGCGGCG
HBV G Clone digest (+) strand              ACTCACTAATCCTCCTTGTCCTCCAACTTGTCCTGGCTATCGCTGGATGTGTCTGCGGCG
HBV H Clone digest (+) strand              ACTTACCAACCTCCTGTCCTCCAACTTGTCCTGGCTATCGTTGGATGTGTCTGCGGCG
```

```
T7 oligomer 376-397 (+)                            ------------------------------AATTTAATACGACTCACTATAGGGAGAGATGTGTCTGCGGCGTTTTATC
T7 oligomer 376-402 (+)                            ------------------------------AATTTAATACGACTCACTATAGGGAGAGATGTGTCTGCGGCGTTTTATCATCT
Probe oligomer 408-435 (-)                                                                                                          GGGTGAGTGAGGA
----Genotype----
HBV A calibrator insert (+) strand       GCAGTCCCCAACCTCCAATCACTCACCAACCTCCTGTCC..CC.ATTTGTC..TGGC..TC.CTG................A..CCTCTTCATCCT
HBV B Clone digest (+) strand            GCAGTCCCCAAATCCAGTCACTCACCAACCTTGTTGTCC..CC.CGGATTTGTC..TGGT..TC.CTG....................CCTCTGCATCCT
HBV C Clone digest (+) strand            GCAGTCCCCAACCTCCAATCACTCACCAACCTCCTTGTCC..CC.ATTTGTC..TGGC..TC.CTG....................CCTCTTCATCCT
HBV C2 Clone digest (+) strand           GCAGTCCCCAACCTCCAATCACTCACCAACCTCTTGTCC..CC.ATTTGTC..TGGC..TC.TTG................A..CCTCTTCATCCT
HBV D Clone digest (+) strand            GCAGTCCCCAACCTCCAATCACTCACCAACCTCCTGTCC..CC.ACTTGTC..TGGT..TC.CTG....................CCTCTTCATCCT
HBV E Clone digest (+) strand            GCAGTCCCCAACCTCCAATCACTCACCAACCTCTTGTCC..CC.ACTTGTC..TGGC..TC.CTG....................CCTCTTCATCCT
HBV F Clone digest (+) strand            GCAGTCCCCAACCTCCAATCACTTACCAACCTCCTGTCC..CC.ACTTGTC..TGGC..TC.CTG....................CCTCTTCATCCT
HBV G Clone digest (+) strand            GCAGTCCCCAATCTCCAATCACTCACTAATCTCCTGTCC..CC.ACTTGTC..TGGC..TC.CTG................A..CCTCTTCATCCT
HBV H Clone digest (+) strand            GCAGTCCCCAATCTCCAATCACTTACCAACCTCCTGTCC..CC.ACTTGTC..TGGT..TC.TTG....................CCTCTTCATCCT
GQ183467_GAP*                            GCAGTCCCCAACCTCCAACCACTCACCAACCTCCTGTCC..CC.ACTTGTC..TGGT..TC.CTG......G..T..CGGC.....A..ACTCTTCCTCTT
```

```
----AmpA----
Oligomer A00(-)                                                                                           `ACGCGGACCGAGUCAAAUGAUCGCGU`
Probe oligomer 668A(-)                                     ----AATTTAATACGACTCACTATAGGGAGACCACAACGGTGGCCTCAGTCCGTTTCTC
T7 oligomer A02(+)                                         ----AATTTAATACGACTCACTATAGGGAGACCACAACGGTGGCCTCAGTCCGTTTCTC
T7 oligomer A35(+)                                         ----AATTTAATACGACTCACTATAGGGAGACCACAACGGTGGGCCTCAGTCCGTTTCTCTTGGCT
Oligomer 452B(+)
Capture oligomer 0707b(+)
Capture oligomer 733(+)
Capture oligomer 1168(+)
Capture oligomer 1290(+)
*****HBV Genotype Clone Insert*****
HBV_Subtype A_adw WHO Std_2            GTATTCCCATCCCATCCCATCGTCCTGGGCTTTCGCAAAATACCTATGGGAGTGGGCCTCAGTCCGTTTCTCTTGGCTCAGTTTACTAGTGCC
HBV_A calibrator insert(+)strand       GTATTCCCATCCCATCCCATCGTCCTGGGCTTTCGCAAAATACCTATGGGAGTGGGCCTCAGTCCGTTTCTCTTGGCTCAGTTTACTAGTGCC
HBV B Clone digest (+) strand          GTATTCCCATCCCATCCATCATCTTGGGCTTTCGCAAGATTCCTATGGGAGTGGGCCTCAGTCCGTTTCTCCTGGCTCAGTTTACTAGTGCC
HBV C Clone digest (+) strand          GTATTCCCATCCCATCCATCATCTTGGGCTTTCGCAAGATTCCTATGGGAGTGGGCCTCAGTCCGTTTCTCCTGGCTCAGTTTACTAGTGCC
HBV C2 Clone digest (+) strand         GTATTCCCATCCCATCCATCATCTTGGGCTTTCGCAAGATTCCTATGGGAGTGGGCCTCAGTCCGTTTCTCCTGGCTCAGTTTACTAGTGCC
HBV D Clone digest (+) strand          GTATTCCCATCCCATCCATCATGGGCTTTCGGAAAATTCCTATGGGAGTGGGCCTCAGCCGTTTCTCCTGGCTCAGTTTACTAGTGCC
HBV E Clone digest (+) strand          GTATTCCCATCCCATCCATCATCCTGGGCTTTCGGAAAATTCCTATGGGAGTGGGCCTCAGCCCGTTTCTCCTGGCTCAGTTTACTAGTGCC
HBV F Clone digest (+) strand          GTATTCCCATCCCATCCATCATCTGGGCTTTAGGAGAAAATACCTATGGGAGTGGGCCTCAGCCCGTTTCTCTCCGGCTCAGTTTACTAGTGCA
HBV G Clone digest (+) strand          GTATTCCCATCCCATCCATCATCTTGGGCTTTCGCAAATACCTATGGGAGTGGGCCTCAGTCCGTTTCGTTCTCATGGCTCAGTTTACTAGTGCC
HBV H Clone digest (+) strand          GTATTCCCATCCCATCCATCATCTTGGGCTTTCGGAAATACCTATGGGAGTGGGCCTCAGCCCGTTTCTCAGCCCGTTTCTCAGGCTCAGTTTACTAGTGCA
```

COMPOSITIONS AND METHODS FOR DETECTING OR QUANTIFYING HEPATITIS B VIRUS

CROSS-REFERENCE TO RELATED APPLICATIONS

This application is a divisional of application Ser. No. 15/816,036, filed Nov. 17, 2017, which claims the benefit of priority of provisional Application No. 62/424,956, filed Nov. 21, 2016, the entire contents of each application is incorporated herein by reference in their entirety.

SEQUENCE LISTING

The present application is filed with a Sequence Listing in electronic format. The Sequence Listing is provided as a file entitled "2021-06-08 01159-0003-01US SequenceListing ST25.txt" created on Jun. 7, 2021, which is 71,480 bytes in size. The information in the electronic format of the sequence listing is incorporated herein by reference in its entirety.

INTRODUCTION AND SUMMARY

Hepatitis B Virus (HBV) can cause acute and chronic disease, with infected individuals being at risk of liver cirrhosis and cancer. Approximately 240 million individuals worldwide are estimated to be infected, with more than 680,000 deaths per year attributable to hepatitis B-related liver disease according to the July 2016 WHO Hepatitis B Fact Sheet. Transmission of HBV can occur through sexual transmission, birth from an infected mother, and other contact with bodily fluids, including on shared items such as toothbrushes and razors as well as needles, and represents an occupational hazard for health care workers.

HBV is a partially double-stranded DNA (dsDNA) virus. Its distribution is worldwide, with genotypes A through H and multiple subtypes known. Antiviral therapy can be effective against chronic HBV, but reliable and sensitive nucleic acid-based detection and quantification are complicated by genetic heterogeneity that results in part from the error-prone nature of HBV replication, in which new viral DNA is reverse-transcribed from RNA by an enzyme lacking proofreading activity. See, e.g., Huang C-J et al. (2013), "Impact of Genetic Heterogeneity in Polymerase of Hepatitis B Virus on Dynamics of Viral Load and Hepatitis B Progression," *PLoS ONE* 8(7): e70169, doi:10.1371/journal.pone.0070169. Hepatitis B is not readily distinguishable on clinical grounds from other types of hepatitis, further emphasizing the importance of molecular detection approaches such as nucleic acid assays. Quantification can be useful, e.g., in monitoring viral load before, during or after antiviral therapy, or in assessing severity of infection. However, assaying for HBV nucleic acid in a manner that reliably detects and quantifies multiple genotypes is non-trivial in that a small set of e.g., two amplification oligomers and one probe is unlikely to amplify and quantify the many known genotypes and subtypes in a comparable manner and may be particularly susceptible to false negatives for some genotypes at low concentrations. On the other hand, using an increased number of oligomers can be complicated by factors that can impact accuracy, sensitivity, or specificity such as increased potential for interactions between oligomers or with unintended target sequences, differential amplification efficiency, resource competition, etc.

Accordingly, there is a need for sensitive, specific, and accurate detection and quantification of HBV irrespective of genotype. Compositions, kits, and methods are provided herein to meet this need, provide other benefits, or at least provide the public with a useful choice.

Provided herein is a composition or kit comprising at least first, second, third, and fourth amplification oligomers, wherein: the first amplification oligomer comprises a target-hybridizing sequence comprising at least 10 contiguous nucleotides of one of SEQ ID NOs: 2 or 3; the second amplification oligomer comprises a target-hybridizing sequence comprising at least 10 contiguous nucleotides of one of SEQ ID NOs: 20, 21, or 22; the third amplification oligomer comprises a target-hybridizing sequence comprising at least 10 contiguous nucleotides of SEQ ID NO: 41; and the fourth amplification oligomer comprises a target-hybridizing sequence comprising at least 10 contiguous nucleotides of one of SEQ ID NOs: 34 or 35; wherein the target-hybridizing sequences of the first, second, third, and fourth amplification oligomers each comprise at least about 14 contiguous nucleotides of Hepatitis B virus sequence or a complement thereof.

Also provided is a method of detecting Hepatitis B virus in a sample, comprising contacting the sample with at least first, second, third, and fourth amplification oligomers, thereby forming a composition, performing a nucleic acid amplification reaction in the composition which produces at least first and second amplicons in the presence of a Hepatitis B virus nucleic acid, and quantifying the first and second amplicons, wherein: the first amplicon is produced through extension of the first and second amplification oligomers in the presence of the Hepatitis B virus nucleic acid; the second amplicon is produced through extension of the third and fourth amplification oligomers in the presence of the Hepatitis B virus nucleic acid; the first amplification oligomer comprises a target-hybridizing sequence comprising at least 10 contiguous nucleotides of one of SEQ ID NOs: 2 or 3; the second amplification oligomer comprises a target-hybridizing sequence comprising at least 10 contiguous nucleotides of one of SEQ ID NOs: 20, 21, or 22; the third amplification oligomer comprises a target-hybridizing sequence comprising at least 10 contiguous nucleotides of SEQ ID NO: 41; and the fourth amplification oligomer comprises a target-hybridizing sequence comprising at least 10 contiguous nucleotides of one of SEQ ID NOs: 34 or 35; wherein the target-hybridizing sequences of the first, second, third, and fourth amplification oligomers each comprise at least about 14 contiguous nucleotides of Hepatitis B virus sequence or a complement thereof.

In some embodiments, one or more of the first, second, third, and fourth amplification oligomers is a promoter-primer. In some embodiments, the second amplification oligomer is a promoter-primer. In some embodiments, the fourth amplification oligomer is a promoter-primer. In some embodiments, one or more of the promoter-primers comprises a T7 promoter located 5' of the target-hybridizing sequence. In some embodiments, one or more promoter-primers comprises the sequence of SEQ ID NO: 8, 9, 10, 11, 12, or 13.

In some embodiments, one or more of the first, second, third, and fourth amplification oligomers comprises a non-nucleotide detectable label.

In some embodiments, the first amplification oligomer comprises a target-hybridizing sequence comprising at least one, two, or three of SEQ ID NOs: 4, 5, 6, or 7. In some embodiments, the second amplification oligomer comprises a target-hybridizing sequence comprising at least one, two, three, four, or five of SEQ ID NOs: 23, 24, 25, 26, 27, and 28. In some embodiments, the third amplification oligomer comprises a target-hybridizing sequence comprising at least one, two, or three of SEQ ID NOs: 42, 43, and 44. In some embodiments, the fourth amplification oligomer comprises a target-hybridizing sequence comprising at least one, two, or three of SEQ ID NOs: 36, 37, 38, and 39.

In some embodiments, the first amplification oligomer comprises at least 11, 12, 13, 14, 15, 16, 17, 18, 19, or 20 contiguous nucleotides of SEQ ID NO: 3. In some embodiments, the first amplification oligomer comprises the sequence of SEQ ID NO: 3. In some embodiments, the first amplification oligomer comprises at least 11, 12, 13, 14, 15, 16, 17, 18, 19, 20, 21, or 22 contiguous nucleotides of SEQ ID NO: 2. In some embodiments, the first amplification oligomer comprises the sequence of SEQ ID NO: 2.

In some embodiments, the composition or kit further comprises an additional amplification oligomer different from the first amplification oligomer, comprising at least 11, 12, 13, 14, 15, 16, 17, 18, 19, or 20 contiguous nucleotides of SEQ ID NO: 3. In some embodiments, the additional amplification oligomer comprises the sequence of SEQ ID NO: 3.

In some embodiments, the second amplification oligomer comprises at least 11, 12, 13, 14, 15, 16, 17, 18, 19, 20, or 21 contiguous nucleotides of SEQ ID NO: 21. In some embodiments, the second amplification oligomer comprises the sequence of SEQ ID NO: 21. In some embodiments, the second amplification oligomer comprises the sequence of SEQ ID NO: 14. In some embodiments, the second amplification oligomer comprises at least 11, 12, 13, 14, 15, 16, 17, 18, 19, 20, 21, 22, 23, 24, 25, or 26 contiguous nucleotides of SEQ ID NO: 22. In some embodiments, the second amplification oligomer comprises the sequence of SEQ ID NO: 22. In some embodiments, the second amplification oligomer comprises the sequence of SEQ ID NO: 15. In some embodiments, the second amplification oligomer comprises at least 11, 12, 13, 14, 15, 16, 17, 18, 19, 20, 21, 22, 23, 24, 25, 26, 27, or 28 contiguous nucleotides of SEQ ID NO: 20. In some embodiments, the second amplification oligomer comprises the sequence of SEQ ID NO: 20.

In some embodiments, the third amplification oligomer comprises at least 11, 12, 13, 14, 15, 16, 17, 18, or 19 contiguous nucleotides of SEQ ID NO: 41. In some embodiments, the third amplification oligomer comprises the sequence of SEQ ID NO: 41.

In some embodiments, the fourth amplification oligomer comprises at least 10 contiguous nucleotides of SEQ ID NO: 35 including the inosine at position 30 of SEQ ID NO: 35. In some embodiments, the fourth amplification oligomer comprises at least 11, 12, 13, 14, 15, 16, 17, 18, 19, 20, 21, 22, 23, 24, 25, 26, 27, or 28 contiguous nucleotides of SEQ ID NO: 34. In some embodiments, the fourth amplification oligomer comprises the sequence of SEQ ID NO: 34. In some embodiments, the fourth amplification oligomer comprises the sequence of SEQ ID NO: 30.

In some embodiments, the composition or kit further comprises a fifth amplification oligomer comprising at least 10 contiguous nucleotides of the sequence of SEQ ID NO: 69 and at least about 14 contiguous nucleotides of Hepatitis B virus sequence or a complement thereof. In some embodiments, the fifth amplification oligomer comprises at least one or two of SEQ ID NO: 70, 71, or 72. In some embodiments, the fifth amplification oligomer comprises at least 11, 12, 13, 14, 15, 16, 17, 18, 19, 20, 21, 22, 23, 24, 25, 26, 27, 28, or 29 contiguous nucleotides of SEQ ID NO: 69. In some embodiments, the fifth amplification oligomer comprises the sequence of SEQ ID NO: 69. In some embodiments, the fifth amplification oligomer is a promoter-primer. In some embodiments, the fifth amplification oligomer comprises the sequence of SEQ ID NO: 67.

In some embodiments, the composition or kit further comprises a sixth amplification oligomer comprising at least 10 contiguous nucleotides of the sequence of SEQ ID NO: 73 and at least about 14 contiguous nucleotides of Hepatitis B virus sequence or a complement thereof. In some embodiments, the sixth amplification oligomer comprises at least one or two of SEQ ID NO: 74, 75, or 76. In some embodiments, the sixth amplification oligomer comprises at least 11, 12, 13, 14, 15, 16, 17, 18, or 19 contiguous nucleotides of SEQ ID NO: 73. In some embodiments, the sixth amplification oligomer comprises the sequence of SEQ ID NO: 73.

In some embodiments, the composition further comprises HBV nucleic acid.

In some embodiments, the composition or kit further comprises at least one DNA polymerase. In some embodiments, the DNA polymerase is a reverse transcriptase. In some embodiments, the DNA polymerase is thermophilic. In some embodiments, the DNA polymerase is mesophilic.

In some embodiments, the composition or kit further comprises an RNA polymerase. In some embodiments, the RNA polymerase is T7 RNA polymerase.

In some embodiments, the composition or kit further comprises at least one, at least two, or each of Mg2+, a buffer, and dNTPs. In some embodiments, the composition or kit further comprises rNTPs.

In some embodiments, the composition or kit further comprises a first control amplification oligomer and a second control amplification oligomer that do not hybridize specifically to HBV. In some embodiments, the first control amplification oligomer comprises at least 10, 11, 12, 13, 14, 15, 16, 17, 18, or 19 contiguous nucleotides of the sequence of SEQ ID NO: 77. In some embodiments, the second control amplification oligomer comprises at least 10, 11, 12, 13, 14, 15, 16, 17, 18, 19, 20, 21, or 22 contiguous nucleotides of the sequence of SEQ ID NO: 86. In some embodiments, the first control amplification oligomer or the second control amplification oligomer is a promoter-primer. In some embodiments, the composition or kit further comprises at least one control probe oligomer configured to hybridize specifically to an amplicon produced from the first and second control amplification oligomers. In some embodiments, the control probe oligomer comprises at least 10, 11, 12, 13, 14, 15, 16, 17, 18, 19, 20, 21, 22, or 23 contiguous nucleotides of the sequence of SEQ ID NO: 79.

In some embodiments, the composition or kit further comprises at least one probe oligomer configured to hybridize specifically to an amplicon produced from the first and second amplification oligomers. In some embodiments, the probe oligomer comprises at least 10 contiguous nucleotides of the sequence of SEQ ID NO: 29 and at least about 14 contiguous nucleotides of Hepatitis B virus sequence or a complement thereof. In some embodiments, the probe oligomer comprises at least 10, 11, 12, 13, 14, 15, 16, 17, 18, 19, 20, 21, 22, 23, 24, 25, 26, 27, or 28 contiguous nucleotides of SEQ ID NO: 82. In some embodiments, the probe oligomer comprises the sequence of SEQ ID NO: 82. In some embodiments, the probe oligomer comprises at least 10, 11, 12, 13, 14, 15, 16, 17, 18, 19, 20, 21, 22, 23, 24, 25, 26, 27, or 28 contiguous nucleotides of SEQ ID NO: 82. In some embodiments, the probe oligomer comprises the sequence of SEQ ID NO: 29.

In some embodiments, the composition or kit further comprises at least one probe oligomer configured to hybridize specifically to an amplicon produced from the third and fourth amplification oligomers. In some embodiments, the probe oligomer comprises at least 10 contiguous nucleotides of the sequence of SEQ ID NO: 40 and at least about 14 contiguous nucleotides of Hepatitis B virus sequence or a complement thereof. In some embodiments, the probe oligomer comprises at least 10, 11, 12, 13, 14, or 15 contiguous nucleotides of SEQ ID NO: 83. In some embodiments, the probe oligomer comprises the sequence of SEQ ID NO: 83. In some embodiments, the probe oligomer comprises at least 11, 12, 13, 14, 15, 16, 17, 18, 19, 20, 21, 22, 23, 24, or 25 contiguous nucleotides of SEQ ID NO: 40. Also provided is a probe oligomer comprising a target-hybridizing region comprising the sequence of SEQ ID NO: 83. In some embodiments, the probe oligomer comprises the sequence of SEQ ID NO: 84. In some embodiments, the probe oligomer comprises the sequence of SEQ ID NO: 85. In some embodiments, the probe oligomer comprises at least 11, 12, 13, 14, 15, 16, 17, 18, 19, 20, 21, 22, 23, 24, or 25 contiguous nucleotides of SEQ ID NO: 40. In some embodiments, the probe oligomer comprises the sequence of SEQ ID NO: 40.

Also provided is an amplification oligomer comprising a target-hybridizing region comprising at least 10 contiguous nucleotides of SEQ ID NO: 35 including the inosine at position 30 of SEQ ID NO: 35 and at least 14 contiguous nucleotides of HBV sequence. In some embodiments, the amplification oligomer comprising a subsequence of SEQ ID NO: 34 or 35 comprises at least 11, 12, 13, 14, 15, 16, 17, 18, 19, 20, 21, 22, 23, 24, 25, 26, 27, 28, 29, 30, 31, 32, 33, or 34 contiguous nucleotides of SEQ ID NO: 35. In some embodiments, the amplification oligomer comprising a subsequence of SEQ ID NO: 34 or 35 comprises the sequence of SEQ ID NO: 35. In some embodiments, the amplification oligomer comprising a subsequence of SEQ ID NO: 34 or 35 comprises the sequence of SEQ ID NO: 31.

In some embodiments, at least one probe oligomer comprises a non-nucleotide detectable label. In some embodiments, the non-nucleotide detectable label is a fluorescent label. In some embodiments, the probe oligomer comprises a quencher. In some embodiments, the non-nucleotide detectable label is a fluorescent label and the quencher absorbs fluorescence to a greater extent when the probe is free than when the probe is annealed to a target nucleic acid. In some embodiments, the fluorescent label is FAM, HEX, or acridine. In some embodiments, the quencher is DABCYL or ROX. In some embodiments, the fluorescent label is attached to the 5'-terminus of the probe oligomer and the quencher is attached to the 3'-terminus of the probe oligomer, or the fluorescent label is attached to the 3'-terminus of the probe oligomer and the quencher is attached to the 5'-terminus of the probe oligomer. In some embodiments, at least about half, at least about 90%, or all of the sugars in the probe oligomer are 2'-O-methyl-ribose. In some embodiments, the probe oligomer comprises a first self-complementary region at its 5' end and a second self-complementary region at its 3' end. In some embodiments, the self-complementary regions can hybridize to form about 4 to 7 Watson-Crick or wobble base pairs. In some embodiments, the self-complementary regions can hybridize to form about 5 Watson-Crick or wobble base pairs.

Also provided is a composition or kit comprising two or more different capture oligomers selected from the following capture oligomers (i)-(iv): (i) a first capture oligomer comprising a target-hybridizing sequence comprising at least 10 contiguous nucleotides of SEQ ID NO: 49 or 99; (ii) a second capture oligomer comprising a target-hybridizing sequence comprising at least 10 contiguous nucleotides of SEQ ID NO: 53, 100, 101, or 104; (iii) a third capture oligomer comprising a target-hybridizing sequence comprising at least 10 contiguous nucleotides of SEQ ID NO: 57, 96, or 102; (iv) a fourth capture oligomer comprising a target-hybridizing sequence comprising at least 10 contiguous nucleotides of SEQ ID NO: 61, 97, 98, or 103; wherein the target-hybridizing sequences of the two or more different capture oligomers each comprise at least about 14 contiguous nucleotides of Hepatitis B virus sequence or a complement thereof.

Also provided is a method of isolating HBV nucleic acid from a sample, comprising contacting the sample with two or more different capture oligomers selected from the following capture oligomers (i)-(iv) under conditions permissive for forming one or more complexes of a capture oligomer and HBV nucleic acid, thereby forming a composition: (i) a first capture oligomer comprising a target-hybridizing sequence comprising at least 10 contiguous nucleotides of SEQ ID NO: 49 or 99; (ii) a second capture oligomer comprising a target-hybridizing sequence comprising at least 10 contiguous nucleotides of SEQ ID NO: 53, 100, 101, or 104; (iii) a third capture oligomer comprising a target-hybridizing sequence comprising at least 10 contiguous nucleotides of SEQ ID NO: 57, 96, or 102; (iv) a fourth capture oligomer comprising a target-hybridizing sequence comprising at least 10 contiguous nucleotides of SEQ ID NO: 61, 97, 98, or 103; wherein the target-hybridizing sequences of the two or more different capture oligomers each comprise at least about 14 contiguous nucleotides of Hepatitis B virus sequence or a complement thereof, and isolating the capture oligomers from the composition. In some embodiments, isolating the capture oligomers comprises associating the capture oligomers with a solid support, and washing the solid support. In some embodiments, the solid support comprises a poly-N sequence which is complementary to a portion of at least one or at least two capture oligomers. In some embodiments, the solid support comprises a binding agent that recognizes an affinity tag present in at least one or at least two capture oligomers.

In some embodiments, the composition or kit comprises at least three of the capture oligomers (i)-(iv). In some embodiments, the composition or kit comprises capture oligomers (i)-(iv).

In some embodiments, the first capture oligomer comprises a target-hybridizing sequence comprising at least one of SEQ ID NOs: 50, 51, and 52. In some embodiments, the first capture oligomer comprises at least 11, 12, 13, 14, 15, 16, 17, 18, 19, 20, 21, 22, 23, or 24 contiguous nucleotides of SEQ ID NO: 49. In some embodiments, the first capture oligomer comprises the sequence of SEQ ID NO: 49.

In some embodiments, the second capture oligomer comprises a target-hybridizing sequence comprising at least one of SEQ ID NOs: 54, 55, and 56. In some embodiments, the second capture oligomer comprises the sequence at least 11, 12, 13, 14, 15, 16, 17, 18, 19, 20, 21, 22, 23, or 24 contiguous nucleotides of SEQ ID NO: 53. In some embodiments, the second capture oligomer comprises of SEQ ID NO: 53.

In some embodiments, the third capture oligomer comprises a target-hybridizing sequence comprising at least one of SEQ ID NOs: 58, 59, and 60. In some embodiments, the third capture oligomer comprises at least 11, 12, 13, 14, 15, 16, 17, 18, 19, 20, 21, 22, 23, 24, or 25 contiguous nucleotides of SEQ ID NO: 57. In some embodiments, the third capture oligomer comprises the sequence of SEQ ID NO: 57.

In some embodiments, the fourth capture oligomer comprises a target-hybridizing sequence comprising at least one of SEQ ID NOs: 62, 63, and 64. In some embodiments, the fourth capture oligomer comprises at least 11, 12, 13, 14, 15, 16, 17, 18, 19, 20, 21, 22, 23, 24, 25, 26, or 27 contiguous nucleotides of SEQ ID NO: 61. In some embodiments, the fourth capture oligomer comprises the sequence of SEQ ID NO: 61.

In some embodiments, at least one of the capture oligomers further comprises a non-nucleotide affinity label. In some embodiments, at least one of the capture oligomers further comprises a non-HBV sequence. In some embodiments, the two, three, or four capture oligomers further comprise a non-HBV sequence. In some embodiments, at least one, two, three, or four capture oligomers further comprise a poly-N sequence. In some embodiments, the poly-N sequence is a poly-A or poly-T sequence.

In some embodiments, the composition or kit further comprises at least one amplification oligomer selected from a first amplification oligomer comprising a target-hybridizing sequence comprising at least 10 contiguous nucleotides of one of SEQ ID NOs: 2 or 3; a second amplification oligomer comprising a target-hybridizing sequence comprising at least 10 contiguous nucleotides of one of SEQ ID NOs: 20, 21, or 22; a third amplification oligomer comprising a target-hybridizing sequence comprising at least 10 contiguous nucleotides of SEQ ID NO: 41; a the fourth amplification oligomer comprising a target-hybridizing sequence comprising at least 10 contiguous nucleotides of one of SEQ ID NOs: 34 or 35; wherein the target-hybridizing sequences of the first, second, third, and fourth amplification oligomers each comprise at least about 14 contiguous nucleotides of Hepatitis B virus sequence or a complement thereof.

In some embodiments, the composition or kit comprises a first amplification oligomer disclosed herein. In some embodiments, the composition or kit comprises a second amplification oligomer disclosed herein. In some embodiments, the second amplification oligomer comprises at least 11, 12, 13, 14, 15, 16, 17, 18, 19, 20, 21, 22, 23, 24, 25, or 26 contiguous nucleotides of SEQ ID NO: 22 and the composition or kit further comprises an additional amplification oligomer that is different from the second amplification oligomer and comprises at least 11, 12, 13, 14, 15, 16, 17, 18, 19, 20, 21, 22, 23, 24, 25, 26, 27, or 28 contiguous nucleotides of SEQ ID NO: 20. In some embodiments, the second amplification oligomer comprises the sequence of SEQ ID NO: 22. In some embodiments, the additional amplification oligomer comprises the sequence of SEQ ID NO: 20. In some embodiments, the composition or kit comprises a amplification oligomer comprising a target-hybridizing sequence comprising at least 10 contiguous nucleotides of one of SEQ ID NOs: 34 or 35 disclosed herein.

In some embodiments, a method further comprises performing a linear amplification wherein at least one amplification oligomer is extended. In some embodiments, prior to the linear amplification, the amplification oligomer is associated with a complex of HBV nucleic acid and a capture oligomer and the complex is associated with a solid support, and the method comprises washing the solid support. In some embodiments, the solid support is a population of microbeads. In some embodiments, the microbeads of the population are magnetic. In some embodiments, following the washing step, the method comprises adding one or more additional amplification oligomers oppositely oriented to an amplification oligomer associated with the complex of HBV nucleic acid and the capture oligomer. In some embodiments, one or more oppositely oriented additional amplification oligomer is a promoter-primer. In some embodiments, one or more oppositely oriented additional amplification oligomer is not a promoter-primer. In some embodiments, the one or more oppositely oriented additional amplification oligomer includes a the first amplification oligomer disclosed herein. In some embodiments, the one or more oppositely oriented additional amplification oligomer includes a second amplification oligomer disclosed herein. In some embodiments, the one or more oppositely oriented additional amplification oligomer includes a third amplification oligomer disclosed herein. In some embodiments, the one or more oppositely oriented additional amplification oligomer includes a amplification oligomer comprising a target-hybridizing sequence comprising at least 10 contiguous nucleotides of one of SEQ ID NOs: 34 or 35 disclosed herein.

In some embodiments, a method further comprises performing an exponential amplification following the linear amplification. In some embodiments, the exponential amplification is transcription-mediated amplification.

In some embodiments, one, two, three, four, or more target-hybridizing sequences of an oligomer comprise at least about 15, 16, 17, 18, 19, 20, 21, 22, 23, 24, or 25 contiguous nucleotides of Hepatitis B virus sequence or a complement thereof.

Also provided is a method of determining a level of Hepatitis B virus in a sample comprising first and second Hepatitis B amplicons associated with first and second labels, respectively, the method comprising: detecting a first signal emitted from the first label; detecting a second signal emitted from the second label; determining whether the first signal or the second signal is above a predetermined threshold; and calculating a level of Hepatitis B virus in the sample, wherein if the first signal or the second signal is above a predetermined threshold, the level is calculated from the greater of the first and second signals; and wherein if the first signal and the second signal are below a predetermined threshold, the level is calculated from an average of the first and second signals.

In some embodiments, the sample is an in vitro sample. In some embodiments, the method comprises determining the average of the first and second signals by determining first and second levels corresponding to the first and second signals, and arithmetically averaging the first and second levels. In some embodiments, the level of Hepatitis B virus is a concentration. In some embodiments, the level of Hepatitis B virus is an amount. In some embodiments, one or both of the first and second amplicons comprise sequence from the S ORF of HBV. In some embodiments, one or both of the first and second amplicons comprise sequence from the P ORF of HBV. In some embodiments, one or both of the first and second amplicons comprise sequence from the overlap of the S and P ORFs of HBV. In some embodiments, the first amplicon comprises at least 10, 11, 12, 13, 14, 15, 16, 17, 18, 19, or 20 contiguous nucleotides of one of SEQ ID NOs: 2 or 3. In some embodiments, the first amplicon comprises at least 10, 11, 12, 13, 14, 15, 16, 17, 18, 19, or 20 contiguous nucleotides of one of SEQ ID NOs: 20, 21, or 22. In some embodiments, the second amplicon comprises at least 10, 11, 12, 13, 14, 15, 16, 17, 18, 19, or 20 contiguous nucleotides of SEQ ID NO: 41. In some embodiments, the second amplicon comprises at least 10, 11, 12, 13, 14, 15, 16, 17, 18, 19, or 20 contiguous nucleotides of one of SEQ ID NOs: 34 or 35.

In some embodiments, the predetermined threshold is at a value where expected random error is greater than or about equal to expected error due to a point mutation. In some embodiments, the predetermined threshold is at a value where expected error due to a point mutation is greater than or about equal to expected random error. In some embodiments, the predetermined threshold corresponds to a concentration in the range of about 10 IU/ml to about 200 IU/ml. In some embodiments, the predetermined threshold is in the range of about 20 IU/ml to about 40 IU/ml, about 40 IU/ml to about 60 IU/ml, about 60 IU/ml to about 80 IU/ml, or about 80 IU/ml to about 100 IU/ml.

In some embodiments, the first label, the second label, or both are fluorescent. In some embodiments, at least one of the first and second labels is attached to a probe. In some embodiments, the probe comprises a quencher.

Also provided is a kit or composition comprising a probe oligomer disclosed herein. Also provided is a kit or composition comprising an amplification oligomer disclosed herein. In some embodiments, the kit or composition further comprises a probe oligomer disclosed herein.

In some embodiments, a kit or composition further comprises at least one, two, three, or four of a first amplification oligomer disclosed herein; a second amplification oligomer disclosed herein; a third amplification oligomer disclosed herein; or a fourth amplification oligomer disclosed herein.

In some embodiments, a kit or composition further comprises at least one, two, three, or four of a first capture oligomer disclosed herein; a second capture oligomer disclosed herein; a third capture oligomer disclosed herein; or a fourth capture oligomer disclosed herein.

In some embodiments, a kit or composition further comprises at least one or two of a fifth amplification oligomer disclosed herein; or a sixth amplification oligomer disclosed herein.

In some embodiments, a kit or composition further comprises an additional amplification oligomer disclosed herein, wherein, if the kit or composition comprises a second amplification oligomer disclosed herein, the additional amplification oligomer is different from the second amplification oligomer.

In some embodiments, one, two or more oligomers disclosed herein are provided in a kit. In some embodiments, one, two or more oligomers disclosed herein are provided in a composition. In some embodiments, the composition is aqueous, frozen, or lyophilized.

Section headings are provided for the convenience of the reader and do not limit the scope of the disclosure.

BRIEF DESCRIPTION OF THE DRAWINGS

Figure 1D:
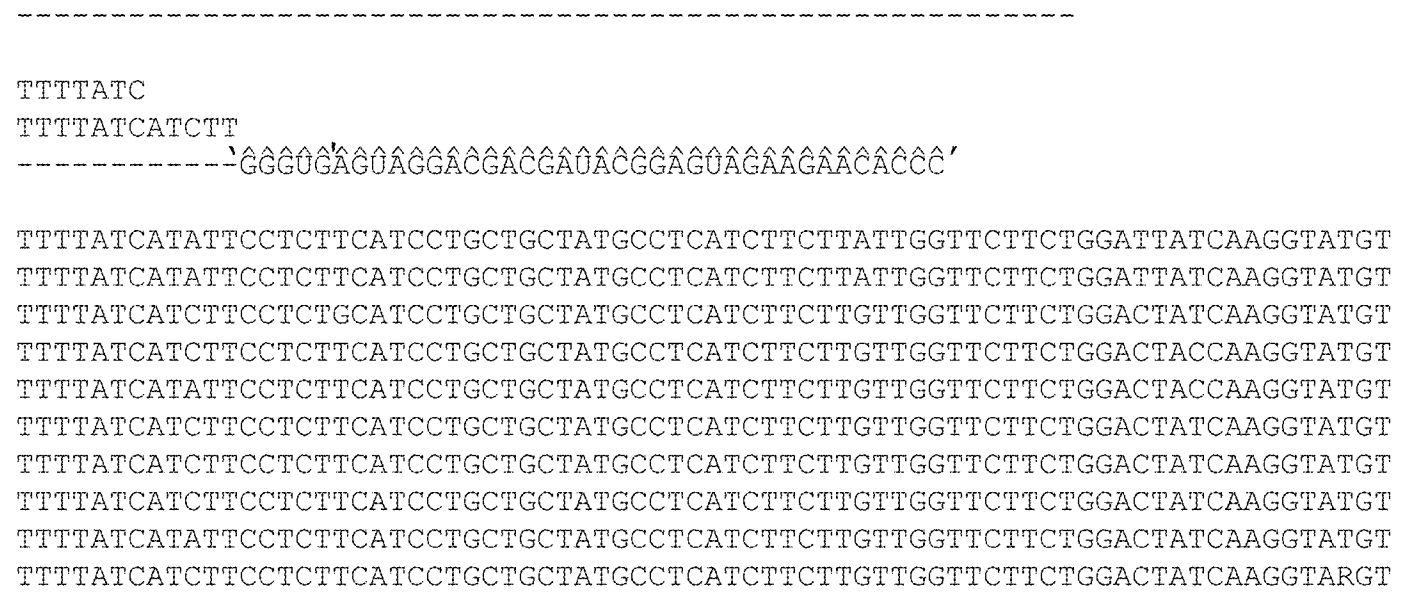

FIG. 1A shows an alignment of exemplary target capture oligomers 0707b and 733 with HBV clone sequences representative of genotypes A-H. The sequences shown in FIG. 1A are: Target Capture Oligomer 0707b(+) (SEQ ID NO:45); Target Capture Oligomer 733(+) (SEQ ID NO:46); HBV Subtype A adw WHO Std 2 (SEQ ID NO:126); HBV A calibrator insert (+) strand (SEQ ID NO:127); HBV B Clone digest (+) strand (SEQ ID NO:128); HBV C Clone digest (+) strand (SEQ ID NO:129); HBV C2 Clone digest (+) strand (SEQ ID NO:130); HBV D Clone digest (+) strand (SEQ ID NO:131); HBV E Clone digest (+) strand (SEQ ID NO:132); HBV F Clone digest (+) strand (SEQ ID NO:133); HBV G Clone digest (+) strand (SEQ ID NO:134); and HBV H Clone digest (+) strand (SEQ ID NO:135).

FIGS. 1B-1C show an alignment of exemplary target capture oligomers 1290 and 1168, respectively, with the 10 most common HBV database sequences at the corresponding locations. Rows are labeled with individual letters (which do not necessarily correspond to HBV genotype nomenclature) and the frequency of matching sequences is indicated. Dots indicate matches to the oligomer and mismatches are shown with letters. The series of N's in row H of FIG. 1B and row G of FIG. 1C indicate HBV sequences with an internal deletion. The sequences shown in FIG. 1B are: 1290 (SEQ ID NO:61); A(1839) (SEQ ID NO:136); B(1152) (SEQ ID NO:137); C(517) (SEQ ID NO:138); D(159) (SEQ ID NO:139); E(136) (SEQ ID NO:140); F(85) (SEQ ID NO:141); G(68) (SEQ ID NO:142); H(64) (SEQ ID NO:143); I(59) (SEQ ID NO:144); and J(27) (SEQ ID NO:145). The sequences shown in FIG. 1C are: 1168 (SEQ ID NO:146); A(2283) (SEQ ID NO:147); B(846) (SEQ ID NO:148); C(335) (SEQ ID NO:149); D(247) (SEQ ID NO:150); E(132) (SEQ ID NO:151); F(117) (SEQ ID NO:152); G(65) (SEQ ID NO:153); H(34) (SEQ ID NO:154); I(29) (SEQ ID NO:155); and J(26) (SEQ ID NO:156).

FIG. 1D shows an alignment of exemplary oligomers with sequences of different HBV clones in a region encompassing HBV positions 376-474. FIG. 1D (cont.) is a continuation of the alignment from the right end of FIG. 1D. The sequences shown in FIG. 1D are: T7 oligomer 376-397(+) (SEQ ID NO:14); T7 oligomer 376-402(+) (SEQ ID NO:15); Probe oligomer 408-435(–) (SEQ ID NO:29); HBV Subtype A adw WHO Std 2 (SEQ ID NO:157); HBV A calibrator insert (+) strand (SEQ ID NO:158); HBV B Clone digest (+)strand (SEQ ID NO:159); HBV C Clone digest (+)strand (SEQ ID NO:160); HBV C2 Clone digest (+)strand (SEQ ID NO:161); HBV D Clone digest (+)strand (SEQ ID NO:162); HBV E Clone digest (+)strand (SEQ ID NO:163); HBV F Clone digest (+)strand (SEQ ID NO:164); HBV G Clone digest (+)strand (SEQ ID NO:165); and HBV H Clone digest (+)strand (SEQ ID NO:166). Notably, SEQ ID NO:29 is presented in the 3' to 5' orientation.

FIG. 2A shows an alignment of exemplary oligomers with sequences of different HBV clones in which differences relative to the 376-402 T7 amplification oligomer (SEQ ID NO: 15) are shown. The sequences shown in FIG. 2A are: T7 oligomer 376-397(+) (SEQ ID NO:14); T7 oligomer 376-402(+) (SEQ ID NO:15); a portion of Probe oligomer 408-435(–) (SEQ ID NO:190); HBV A calibrator insert(+) strand (SEQ ID NO:167); HBV B Clone digest(+)strand (SEQ ID NO:168); HBV C Clone digest(+)strand (SEQ ID NO:169); HBV C2 Clone digest (+) strand (SEQ ID NO:170); HBV D Clone digest (+) strand (SEQ ID NO:171); HBV E Clone digest (+) strand (SEQ ID NO:172); HBV F Clone digest (+) strand (SEQ ID NO:173); HBV G Clone digest (+) strand (SEQ ID NO:174); HBV H Clone digest (+) strand (SEQ ID NO:175); and GQ183467 GAP* (SEQ ID NO:176). Notably, SEQ ID NO:190 (represents a portion of SEQ ID NO:29) is presented in the 3' to 5' orientation.

FIG. 2B (cont.) is a continuation of the alignment from the right end of FIG. 2B. The sequences shown in FIG. 2B are: Probe oligomer 408-435(–) (SEQ ID NO:29); NT7 oligomer 455-474(+) (SEQ ID NO:191); T7 oligomer 376-397(+) (SEQ ID NO: 14); T7 oligomer 376-402(+) (SEQ ID NO: 15); HBV Subtype A adw WHO Std (SEQ ID NO:177); and H.B AB674430 (SEQ ID NO:178). Notably, SEQ ID NOs:191 and 29 are presented in the 3' to 5' orientation. SEQ ID NO:191 is a single nucleotide longer at the 3' end compared to SEQ ID NO:2.

FIG. 3 shows an alignment of exemplary oligomers with sequences of different HBV clones in a region encompassing HBV positions 640-720. FIG. 3 (cont.) is a continuation of the alignment from the right end of FIG. 3. The sequences shown in FIG. 3 are: Oligomer A00(−) (SEQ ID NO:179); Probe oligomer 668A(−) (SEQ ID NO:40); T7 oligomer A02(+) (SEQ ID NO:30); T7 oligomer A35(+) (SEQ ID NO:31); Capture oligomer 0707b(+) (SEQ ID NO:45); Capture oligomer 733(+) (SEQ ID NO:91); HBV Subtype A adw WHO Std 2 (SEQ ID NO:180); HBV A calibrator insert(+)strand (SEQ ID NO:181); HBV B Clone digest (+) strand (SEQ ID NO:182); HBV C Clone digest (+) strand (SEQ ID NO:183); HBV C2 Clone digest (+) strand (SEQ ID NO:184); HBV D Clone digest (+) strand (SEQ ID NO:185); HBV E Clone digest (+) strand (SEQ ID NO:186); HBV F Clone digest (+) strand (SEQ ID NO:187); HBV G Clone digest (+) strand (SEQ ID NO:188); and HBV H Clone digest (+) strand (SEQ ID NO:189). Notably, SEQ ID NO:40 is presented in the 3' to 5' orientation.

FIGS. 4A and 4C show detection of the amplicon detected by the 408-435 probe oligomer. FIGS. 4B and 4D show detection of the amplicon detected by the 668A probe oligomer. Arrows indicate traces for 2,000 IU/ml samples and brackets indicate traces for lower-concentration samples. Traces for the lowest concentration (2 IU/ml) are in gray and traces for the intermediate concentration (10 IU/ml) are in black.

DETAILED DESCRIPTION

A. Definitions

Figure 2B:
FIG. 2B shows an alignment of exemplary oligomers, a representative HBV genotype A sequence, and the HBV sequence of GenBank Accession No. AB674430, which contains a 108 nucleotide deletion.
Figure 2B:
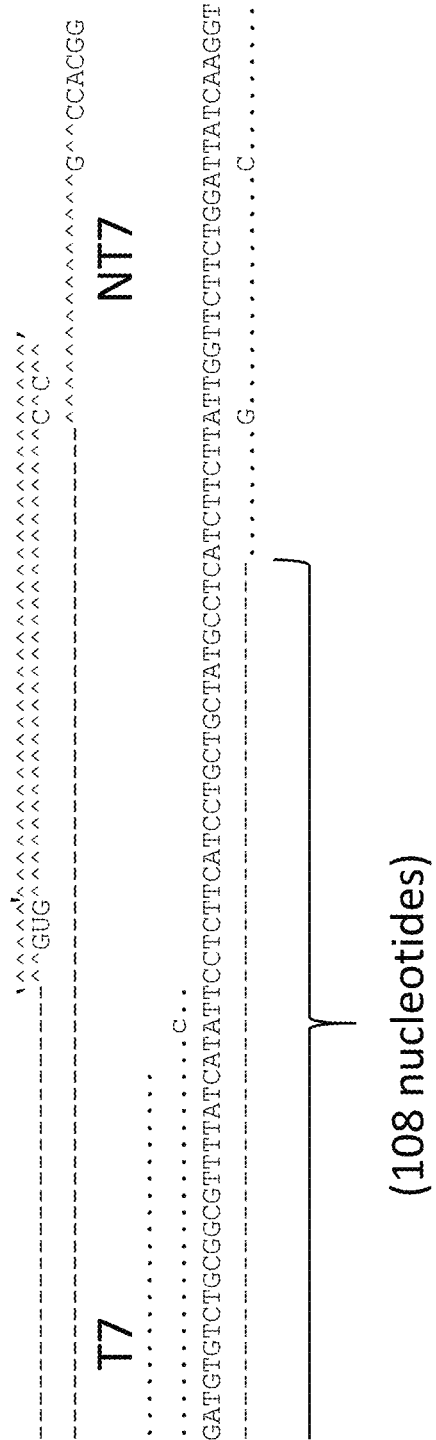

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "an oligomer" includes a plurality of oligomers and the like.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

"Sample" includes any specimen that may contain hepatitis B virus (HBV) or components thereof such as nucleic acids or fragments of nucleic acids. Samples include "biological samples" which include any tissue or material derived from a living or dead human that may contain HBV or target nucleic acid derived therefrom, including e.g., peripheral blood, plasma, serum, lymph node, gastrointestinal tissue (e.g., liver), or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., The Biochemistry of the Nucleic Acids 5-36, Adams et al., ed., 11th ed., 1992; Abraham et al., 2007, BioTechniques 43: 617-24), which include derivatives of purine or pyrimidine bases (e.g., $N^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see. e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., Biochemistry 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

A sequence is a "Hepatitis B virus sequence" if it or its complement occurs in, is at least about 90% or at least about 95% identical to, or contains no more than one mismatch relative to any genotype, subtype, or isolate of HBV, thereto, such that, for example, "14 contiguous nucleotides of Hepatitis B virus sequence" refers to a 14-mer that matches at least 13 out of 14 positions of a genotype, subtype, or isolate of HBV, or the complement thereof. The presence of a U is considered equivalent to a T and vice versa for purposes of determining whether a sequence qualifies as a Hepatitis B virus sequence. The target-hybridizing regions of exemplary oligomers disclosed herein, the HBV-derived sequence of in vitro transcripts disclosed herein, and subsequences thereof are also considered Hepatitis B virus sequence. Thus, examples of Hepatitis B virus sequence include SEQ ID NOs: 1-7, 20-28, 34-39, 49-64, 69-76, 82-84, and 96-125, along with the full HBV genomic sequences referred to by accession number in the Table of Sequences. In some embodiments, the genotype, subtype, or isolate of HBV referred to above is a known genotype, subtype, or isolate of HBV, e.g., which is present in a sequence database or publication available at the date of this disclosure. When numeric positions in an HBV nucleic acid are referred to, such positions are with reference to SEQ ID NO: 1, which is an HBV genotype A1 sequence. It is understood that positions may vary in other genotypes; for example, position 700 in SEQ ID NO: 1 aligns to position 703 of the HBV genotype F1a sequence of SEQ ID NO: 101. Corresponding positions can be determined using an appropriate alignment algorithm such as the Needleman-Wunsch algorithm with standard parameters.

When an oligomer comprises, e.g., "at least 10 contiguous nucleotides of" a specified SEQ ID NO and "at least about 14 contiguous nucleotides of Hepatitis B virus sequence," the same nucleotides can be counted toward both (i) and (ii), e.g., the at least 14 contiguous nucleotides of Hepatitis B virus sequence can comprise any or all of the at least 10 contiguous nucleotides of the specified SEQ ID NO, to the extent consistent with the foregoing definition of Hepatitis B virus sequence. Similarly, an "oligomer comprises a target-hybridizing sequence comprising at least two" (or more) of a plurality of specified SEQ ID NOs if each of the sequence of the SEQ ID NOs is present, regardless of whether they overlap. Thus, as a simplified example, CAT comprises both CA and AT.

For two molecules to "anneal to at least N common position(s)" means that the molecules have hybridization sites that overlap by N or more nucleotides on the same or opposite strands of a target nucleic acid, e.g., an HBV nucleic acid. For example, a first oligomer that is configured to specifically hybridize to positions 655-681 and a second oligomer that is configured to specifically hybridize to positions 679-699 anneal to three common positions (679, 680, and 681) regardless of whether (i) they are both configured to specifically hybridize to the same strand or (ii) one is configured to specifically hybridize to the sense or (+) strand and the other is configured to specifically hybridize to the antisense or (−) strand.

The term "polynucleotide" as used herein denotes a nucleic acid chain. Throughout this application, nucleic acids are designated by the 5'-terminus to the 3'-terminus. Synthetic nucleic acids, e.g., DNA, RNA, DNA/RNA chimerics, (including when non-natural nucleotides or analogues are included therein), are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar, and a nitrogenous base (also referred to herein as "nucleobase"). The 5-carbon sugar found in RNA is ribose. In DNA, the 5-carbon sugar is 2'-deoxyribose. The term also includes analogs of such subunits, such as a methoxy group at the 2' position of the ribose (also referred to herein as "2'-O-Me" or "2'-methoxy"). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units do not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. The (+) strand corresponds to the viral mRNA sequence and the (−) is the complement thereof. The exemplary genotype A sequence of SEQ ID NO: 1 represents a (+) strand.

"Target-hybridizing sequence" is used herein to refer to the portion of an oligomer that is configured to hybridize with a target nucleic acid sequence. In some embodiments, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to various genotypes of HBV. It is understood that other reasons exist for configuring a target-hybridizing sequence to have less than 100% complementarity to a target nucleic acid.

The term "targets a sequence" as used herein in reference to a region of HBV nucleic acid refers to a process whereby an oligonucleotide hybridizes to the target sequence in a manner that allows for amplification and detection as described herein. In one preferred embodiment, the oligonucleotide is complementary with the targeted HBV nucleic acid sequence and contains no mismatches. In another preferred embodiment, the oligonucleotide is complementary but contains 1, 2, 3, 4, or 5 mismatches with the targeted HBV nucleic acid sequence. In some embodiments, the oligonucleotide that hybridizes to the HBV nucleic acid sequence includes at least 10 to as many as 50 nucleotides complementary to the target sequence. It is understood that at least 10 and as many as 50 is an inclusive range such that 10, 50 and each whole number there between are included. In some embodiments, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced HBV target region. Such an oligonucleotide is not limited to targeting that sequence only, but is rather useful as a composition, in a kit, or in a method for targeting a HBV target nucleic acid. The oligonucleotide is designed to function as a component of an assay for amplification and detection of HBV from a sample, and therefore is designed to target HBV in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. "Upstream" refers to a location closer to the 5' end of the (+) strand (or the 3' end of the (−) strand) than a given position. "Downstream" refers to a location closer to the 3' end of the (+) strand (or the 5' end of the (−) strand) than a given position.

The term "fragment," as used herein in reference to the targeted HBV nucleic acid, refers to a piece of contiguous nucleic acid. In certain embodiments, the fragment includes contiguous nucleotides from an HBV RNA corresponding to SEQ ID NO: 1, wherein the number of contiguous nucleotides in the fragment are less than that for the entire sequence corresponding to SEQ ID NO:1.

The term "region," as used herein, refers to a portion of a nucleic acid wherein said portion is smaller than the entire nucleic acid. For example, when the nucleic acid in reference is an oligonucleotide promoter primer, the term "region" may be used to refer to the smaller promoter portion of the entire oligonucleotide. Similarly, and also as example only, when the nucleic acid is an HBV nucleic acid, the term "region" may be used to refer to a smaller area of the nucleic acid, wherein the smaller area is targeted by one or more oligonucleotides of the disclosure. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., a fluorophore).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA or DNA equivalent thereof as well as DNA/RNA chimerics thereof and includes the complements thereof unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In some embodiments, the percentage is from 100% to about 85%. In some embodiments, this percentage is from 100% to about 90%, e.g., from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3' OH to prevent enzyme-mediated extension of the oligomer in an amplification reaction. For example, blocked amplification oligomers and/or detection probes present during amplification may not have functional 3' OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. In some embodiments, the 5' region of an amplification oligonucleotide may include a promoter sequence that is non-complementary to the target nucleic acid (which may be referred to as a "promoter primer"). Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence that hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, In some embodiments comprising a blocking moiety at its 3'-terminus as described above. As referred to herein, a "T7 Provider" is a blocked promoter provider oligonucleotide that provides an oligonucleotide sequence that is recognized by T7 RNA polymerase.

A "terminating oligonucleotide" is an oligonucleotide comprising a base sequence that is substantially complementary to a sequence within the target nucleic acid in the vicinity of the 5'-end of the target region, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-ME ribonucleotides. These modified nucleotides have demonstrated higher thermal stability of complementary duplexes. The 2'-O-ME ribonucleotides also function to increase the resistance of oligonucleotides to exonucleases, thereby increasing the half-life of the modified oligonucleotides. (See, e.g., Majlessi et al., Nucleic Acids Res. 26:2224-9, 1988, incorporated by reference herein.) Other modifications as described elsewhere herein may be utilized in addition to or in place of 2'-O-Me ribonucleotides. For example, a terminating oligonucleotide may comprise PNA or an LNA. (See. e.g., Petersen et al., J. Mol. Recognit. 13:44-53, 2000, incorporated by reference herein.) A terminating oligonucleotide of the present disclosure typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present disclosure is typically at least 10 bases in length, and may extend up to 15, 20, 25, 30, 35, 40, 50 or more nucleotides in length. While a terminating oligonucleotide typically or necessarily includes a 3'-blocking moiety, "3'-blocked" oligonucleotides are not necessarily terminating oligonucleotides.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see. e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see. e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see. e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see. e.g., U.S. Pat. Nos. 5,422,252; 5,547,861; and 5,648,211; each incorporated by reference herein).

As used herein, the term "linear amplification" refers to an amplification mechanism that is designed to produce an increase in the target nucleic acid linearly proportional to the amount of target nucleic acid in the reaction. For instance, multiple RNA copies can be made from a DNA target using a transcription-associated reaction, where the increase in the number of copies can be described by a linear factor (e.g., starting copies of template×100). In some embodiments, a first phase linear amplification in a multiphase amplification procedure increases the starting number of target nucleic acid strands or the complements thereof by at least 10 fold, e.g., by at least 100 fold, or by 10 to 1,000 fold before the second phase amplification reaction is begun. An example of a linear amplification system is "T7-based Linear Amplification of DNA" (TLAD; see Liu et al., BMC Genomics, 4: Art. No. 19, May 9, 2003). Other methods are known, e.g., from U.S. Pat. No. 9,139,870, or disclosed herein. Accordingly, the term "linear amplification" refers to an amplification reaction which does not result in the exponential amplification of a target nucleic acid sequence. The term "linear amplification" does not refer to a method that simply makes a single copy of a nucleic acid strand, such as the transcription of an RNA molecule into a single cDNA molecule as in the case of reverse transcription (RT)-PCR.

As used herein, the term "exponential amplification" refers to nucleic acid amplification that is designed to produce an increase in the target nucleic acid geometrically proportional to the amount of target nucleic acid in the reaction. For example, PCR produces one DNA strand for every original target strand and for every synthesized strand present. Similarly, transcription-associated amplification produces multiple RNA transcripts for every original target strand and for every subsequently synthesized strand. The amplification is exponential because the synthesized strands are used as templates in subsequent rounds of amplification. An amplification reaction need not actually produce exponentially increasing amounts of nucleic acid to be considered exponential amplification, so long as the amplification reaction is designed to produce such increases.

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, e.g., a T7 promoter, and optionally may include one or more other oligonucleotides. When a T7 promoter-containing oligomer is used, it may be referred to as a "T7 primer" or "T7 oligomer"; other primers/oligomers may be referred to as "non-T7" or "NT7" primers/oligomers. TMA methods and single-primer transcription-associated amplification methods are embodiments of amplification methods used for detection of HBV target sequences as described herein. Variations of transcription-associated amplification are well-known in the art as previously disclosed in detail (see. e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored through real-time detection.

The term "amplicon" or "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current disclosure may comprise non-target specific sequences. Amplicons can be double-stranded or single-stranded and can include DNA, RNA, or both. For example, DNA-dependent RNA polymerase transcribes single-stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current disclosure. Such representation is not meant to limit the amplicon to the representation shown. Skilled artisans in possession of the instant disclosure will use amplification oligomers and polymerase enzymes to generate any of the numerous types of amplicons, all within the spirit and scope of the current disclosure.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," "probe oligomer," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof (e.g., DNA/RNA chimerics) and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see. e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see. e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see. e.g., U.S. Pat. Nos. 5,656,207; 5,658,737; and 5,639,604; each incorporated by reference herein). Synthesis and methods of attaching labels to nucleic acids and detecting labels are well known. (See. e.g., Sambrook et al. Molecular Cloning. A Laboratory Manual, 2nd ed. (Cold Spring Harbor Laboratory Press, Cold Spring Harbor, N.Y., 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see. e.g., U.S. Pat. Nos. 6,180,340 and 6,350,579, each incorporated by reference herein).

"Capture probe," "capture oligonucleotide," "capture oligomer," "target capture oligomer," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," "immobilized binding partner," "immobilized oligomer," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size+ 5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or two different regions of the same single-stranded nucleic acid, have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T, or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" or "Watson-Crick" hydrogen-bonded base pairs with an analogous sequence of nucleotides of the other single-stranded region, such that A is paired with U or T and C is paired with G, the nucleotides sequences are "completely" complementary (see. e.g., Sambrook et al., Molecular Cloning. A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687, etc.). Reference to "the complement" of a particular sequence generally indicates a completely complementary sequence unless the context indicates otherwise.

"Wobble" base pairs refer to a pairing of a G to either a U or a T.

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately detect or quantitate RNA replicates or complementary DNA (cDNA) of the target sequence formed during the amplification. Appropriate hybridization conditions are well-known in the art, may be predicted based on sequence composition, or can be determined by using routine testing methods (see. e.g., Sambrook et al., Molecular Cloning. A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of HBV nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from $E.$ $coli$, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required for a reverse transcriptase to initiate synthesis with both RNA and DNA templates.

"Thermophilic" indicates that an enzyme, e.g., a polymerase, exhibits optimal activity at a temperature greater than about 45° C., e.g., at a temperature in the range from about 50° C. to 99° C. In some embodiments, a thermophilic enzyme does not lose more than 50% of its activity upon incubation for 20 minutes at 60° C. In some embodiments, a thermophilic enzyme is obtained or derived from a thermophilic organism, e.g., an organism whose optimal growth temperature is greater than or equal to about 45° C., e.g., greater than or equal to about 50° C.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present disclosure will be readily apparent to those of ordinary skill in the art.

As used herein, a "standard curve" is a representation that relates (1) a pre-amplification amount of a polynucleotide, and (2) some time-dependent indicia of a post-amplification amount of a corresponding amplicon. For example, a standard curve can be a graph having known numbers of input template molecules plotted on the x-axis, and a time value required for the amplification reaction to achieve some level of detectable amplicon production plotted on the y-axis. Standard curves typically are produced using control polynucleotide standards containing known numbers of polynucleotide templates. Standard curves can be stored in electronic form or can be represented graphically. The pre-amplification amount of an analyte polynucleotide in a test sample can be determined by comparing a measured time-dependent value obtained for the test sample with a standard curve, as will be familiar to those having an ordinary level of skill in the art.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the terms "relative light unit" ("RLU") and "relative fluorescence unit" ("RFU") represent arbitrary units of measurement indicating the relative number of photons emitted by the sample at a given wavelength or band of wavelengths. A measurement of RLU or RFU varies with the characteristics of the detector used for the measurement.

As used herein, the terms "TTime," "emergence time," and "time of emergence" are interchangeable and represent the threshold time or time of emergence of signal in a real-time plot of the assay data. TTime values estimate the time at which a particular threshold indicating amplicon production is passed in a real-time amplification reaction. TTime and an algorithm for calculating and using TTime values are described in Light et al., U.S. Pub. No. 2006/0276972, paragraphs [0517] through [0538], the disclosure of which is incorporated by reference herein. A curve fitting procedure is applied to normalized and background-adjusted data. The curve fit is performed for only a portion of the data between a predetermined low bound and high bound. The goal, after finding the curve that fits the data, is to estimate the time corresponding to the point at which the curve or a projection thereof intersects a predefined threshold value. In one embodiment, the threshold for normalized data is 0.11. The high and low bounds are determined empirically as that range over which curves fit to a variety of control data sets exhibit the least variability in the time associated with the given threshold value. For example, in one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined as follows:

$$TTime=(Threshold-b)/m.$$

Unless otherwise indicated, a concentration of 1 IU/ml HBV corresponds to 5 copies/ml of HBV nucleic acid. 1 log copy/ml of HBV nucleic acid corresponds to 10 copies/ml; 2 log copies/ml of HBV nucleic acid corresponds to 100 copies/ml; and so on, i.e., n log copies/ml equals $10^n$ copies/ml.

Unless otherwise indicated, oligomer sequences appearing in tables below follow the conventions that lower case letters indicate 2'-O-methyl RNA, and upper case letters indicate DNA. "(c9)" indicates a —$(CH_2)_9$— linker. In vitro transcript (IVT) sequences are RNA unless otherwise indicated.

References, particularly in the claims, to "the sequence of SEQ ID NO: X" refer to the base sequence of the corresponding sequence listing entry and do not require identity of the backbone (e.g., RNA, 2'-O-Me RNA, or DNA) unless otherwise indicated. Furthermore, T and U residues are to be considered interchangeable for purposes of sequence listing entries unless otherwise indicated, e.g., a sequence can be considered identical to SEQ ID NO: 2 regardless of whether the residue at the sixth position is a T or a U.

B. Oligomers, Compositions, and Kits

The present disclosure provides oligomers, compositions, and kits, useful for amplifying, detecting, or quantifying HBV from a sample.

In some embodiments, amplification oligomers are provided. Amplification oligomers generally comprise a target-hybridizing region, e.g., configured to hybridize specifically to an HBV nucleic acid. While oligomers of different lengths and base composition may be used for amplifying HBV nucleic acids, in some embodiments oligomers in this disclosure have target-hybridizing regions from 10 to 60 bases in length, between 14 and 50 bases in length, or between 15 and 40 bases in length. In some embodiments, an initial amplification oligomer is used having a relatively long target hybridizing region such as about 30-50 nucleotides, e.g., 35-45, and at a later stage amplification oligomers with shorter target-hybridizing regions are used, e.g., about 14-35 nucleotides, such as about 15-30 nt.

In certain embodiments, an amplification oligomer as described herein is a promoter primer further comprising a promoter sequence located 5' to the target-hybridizing sequence and which is non-complementary to the HBV target nucleic acid. For example, in some embodiments of an oligomer combination as described herein for amplification of an HBV target region, an amplification oligomer as described above is a promoter primer further comprising a promoter sequence 5' to the target-hybridizing sequence. Alternatively, an amplification oligomer can be a promoter provider comprising a promoter sequence. In particular embodiments, the promoter sequence is a T7 RNA polymerase promoter sequence such as, for example, a T7 promoter sequence having the sequence shown in SEQ ID NO:8. In specific variations, a promoter primer comprises the non-HBV sequence including a T7 promoter shown in one of SEQ ID NOs:9, 10, 11, 12, or 13. In some embodiments, at least one, e.g., two, three, or four promoter primers are provided comprising a target-hybridizing sequence that contains (+)-strand HBV sequence.

In some embodiments, an amplification oligomer is not a promoter primer or does not comprise a promoter sequence. For example, in PCR-based approaches the primers are generally not promoter primers, and in TMA-based approaches at least one primer that is not a promoter primer is typically used (while at least one promoter primer is also used). In some embodiments, at least one, e.g., two, three, or four amplification oligomers that are not promoter primers are provided comprising a target-hybridizing sequence that contains (−)-strand HBV sequence.

In some embodiments, a first amplification oligomer is provided which is a reverse amplification oligomer, i.e., it is configured to hybridize specifically to (+) strand HBV nucleic acid; put another way, its target-hybridizing sequence corresponds to the "antisense" sequence of HBV.

In some embodiments, the target sequence of the first amplification oligomer comprises position 449 of an HBV genomic nucleic acid such as SEQ ID NO: 1, e.g., positions 448-450, 447-451, 446-452, 445-453, 444-454, 443-455, 442-456, 441-457, 440-458, or 439-459. In some embodiments, the first amplification oligomer comprises a sequence having up to 1 or 2 mismatches relative to SEQ ID NO: 2. In some embodiments, the first amplification oligomer comprises a sequence having up to 1 or 2 mismatches relative to SEQ ID NO: 3. Various embodiments of the first amplification oligomer, including with respect to its sequence, are disclosed in the summary above, any of which can be combined to the extent feasible with the features discussed above in this section.

In some embodiments in which the first amplification oligomer is provided, an additional reverse amplification oligomer different from the first amplification oligomer is also provided which is also configured to hybridize specifically to (+) strand HBV nucleic acid. Such an additional amplification oligomer can anneal to common positions with the first amplification oligomer, e.g., at least 1, 2, 3, 4, 5, 6, 7, 8, 9, 10, 11, 12, 13, 14, 15, 16, 17, 18, 19, or 20 common positions with the first amplification oligomer. In some embodiments, the target sequence of the additional amplification oligomer comprises position 449 of an HBV genomic nucleic acid such as SEQ ID NO: 1, e.g., positions 448-450, 447-451, 446-452, 445-453, 444-454, 443-455, 442-456, 441-457, 440-458, or 439-459. In some embodiments, the additional amplification oligomer comprises a sequence having up to 1 or 2 mismatches relative to SEQ ID NO: 2. In some embodiments, the additional amplification oligomer comprises a sequence having up to 1 or 2 mismatches relative to SEQ ID NO: 3. As described in the examples, using such an additional amplification oligomer can improve the relative accuracy of quantification of HBV nucleic acid despite sequence variation between genotypes. In some embodiments, the first amplification oligomer comprises at least 10 contiguous nucleotides of SEQ ID NO: 2 and the additional amplification oligomer comprises at least 10 contiguous nucleotides of SEQ ID NO: 3. Various embodiments of the additional amplification oligomer, including with respect to its sequence, are disclosed in the summary above, any of which can be combined to the extent feasible with the features discussed above in this section.

In some embodiments, a second amplification oligomer is provided which is a forward amplification oligomer, i.e., it is configured to hybridize specifically to (−) strand HBV nucleic acid; put another way, its target-hybridizing sequence corresponds to the "antisense" sequence of HBV.

In some embodiments, the target sequence of the second amplification oligomer comprises position 386 or 387 of an HBV genomic nucleic acid such as SEQ ID NO: 1, e.g., positions 386-387, 385-388, 384-389, 383-390, 382-391, 381-392, 380-393, 379-394, 378-395, 377-396, or 376-397. In some embodiments, the second amplification oligomer comprises a sequence having up to 1 or 2 mismatches relative to SEQ ID NO: 18. In some embodiments, the second amplification oligomer comprises a sequence of SEQ ID NO: 19, 20, 21, 22, or a sequence having up to 1 or 2 mismatches relative thereto. In some embodiments, the second amplification oligomer comprises a target-hybridizing sequence comprising positions N to 397 of SEQ ID NO: 1, where N is 376, 377, 378, 379, 380, 381, 382, 383, or 384, or a sequence having up to 1 or 2 mismatches relative thereto. In some embodiments, the second amplification oligomer comprises a target-hybridizing sequence comprising positions N to 402 of SEQ ID NO: 1, where N is 376, 377, 378, 379, 380, 381, 382, 383, 384, 385, 386, 387, 388, or 389, or a sequence having up to 1 or 2 mismatches relative thereto. Various embodiments of the second amplification oligomer, including with respect to its sequence, are disclosed in the summary above, any of which can be combined to the extent feasible with the features discussed above in this section.

In some embodiments in which the second amplification oligomer is provided, an additional forward amplification oligomer different from the second amplification oligomer is also provided which is also configured to hybridize specifically to (−) strand HBV nucleic acid. Such an additional amplification oligomer can anneal to common positions with the second amplification oligomer, e.g., at least 1, 2, 3, 4, 5, 6, 7, 8, 9, 10, 11, 12, 13, 14, 15, 16, 17, 18, 19, or 20 common positions with the second amplification oligomer. In some embodiments, the target sequence of the additional amplification oligomer comprises position 389 of an HBV genomic nucleic acid such as SEQ ID NO: 1, e.g., positions 388-390, 387-391, 386-392, 385-393, 384-394, 383-395, 382-396, 381-397, 380-398, 379-399, 378-400, 377-401, or 376-402. In some embodiments, the additional amplification oligomer comprises a sequence having up to 1 or 2 mismatches relative to SEQ ID NO: 19. In some embodiments, the additional amplification oligomer comprises a sequence having up to 1 or 2 mismatches relative to SEQ ID NO: 18, 20, 21, or 22. Using such an additional amplification oligomer can improve the relative accuracy of quantification of HBV nucleic acid despite sequence variation between genotypes. In some embodiments, the second amplification oligomer comprises at least 10 contiguous nucleotides of SEQ ID NO: 18 and the additional amplification oligomer comprises at least 10 contiguous nucleotides of SEQ ID NO: 19. The target-hybridizing region of the additional amplification oligomer can be longer than the target-hybridizing region of the second amplification oligomer, e.g., by 1, 2, 3, 4, 5, 6, 7, 8, 9, or 10 nucleotides, such as about 4-6 nucleotides, e.g., 5 nucleotides. Various embodiments of such an additional amplification oligomer, including with respect to its sequence, are disclosed in the summary above, any of which can be combined to the extent feasible with the features discussed above in this section.

The first, second, and optionally additional amplification oligomers discussed above can be used in an amplification reaction to produce a first amplicon, e.g., comprising positions such as 425, e.g., 420-430, 416-434, 406-444, 396-454, 386-464, or 376-474 of an HBV nucleic acid such as SEQ ID NO: 1.

In some embodiments, a third amplification oligomer is provided which is a reverse amplification oligomer, i.e., it is configured to hybridize specifically to (+) strand HBV nucleic acid; put another way, its target-hybridizing sequence corresponds to the "antisense" sequence of HBV.

In some embodiments, the target sequence of the third amplification oligomer comprises position 698 or 699 of an HBV genomic nucleic acid such as SEQ ID NO: 1, e.g., positions 698-699, 697-700, 696-701, 695-702, 694-703, 693-704, 692-705, 691-706, 690-707, or 689-708. In some embodiments, the third amplification oligomer comprises a sequence having up to 1 or 2 mismatches relative to SEQ ID NO: 41. Various embodiments of the third amplification oligomer, including with respect to its sequence, are disclosed in the summary above, any of which can be combined to the extent feasible with the features discussed above in this section.

In some embodiments, a fourth amplification oligomer is provided which is a forward amplification oligomer, i.e., it is configured to hybridize specifically to (−) strand HBV nucleic acid; put another way, its target-hybridizing sequence corresponds to the "antisense" sequence of HBV.

In some embodiments, the target sequence of the fourth amplification oligomer comprises position 656 of an HBV genomic nucleic acid such as SEQ ID NO: 1, e.g., positions or 655-657, 654-658, 653-659, 652-660, 651-661, 650-662, 649-663, 648-664, 647-665, or 646-666. In some embodiments, the fourth amplification oligomer comprises a sequence having up to 1 or 2 mismatches relative to SEQ ID NO: 40. In some embodiments, the fourth amplification oligomer comprises a target-hybridizing sequence comprising positions N to 666 of an HBV nucleic acid sequence such as SEQ ID NO: 1, where N is 646, 647, 648, 649, 650, 651, 652, or 653, or a sequence having up to 1 or 2 mismatches relative thereto. Various embodiments of the fourth amplification oligomer, including with respect to its sequence, are disclosed in the summary above, any of which can be combined to the extent feasible with the features discussed above in this section.

The third and fourth amplification oligomers discussed above can be used in an amplification reaction to produce a second amplicon, e.g., comprising positions such as 677 or 678, e.g., 673-682, 668-687, 658-697, 648-707, or 646-708 of an HBV nucleic acid sequence such as SEQ ID NO: 1.

In some embodiments, a fifth amplification oligomer is provided which is a forward amplification oligomer, i.e., it is configured to hybridize specifically to (−) strand HBV nucleic acid; put another way, its target-hybridizing sequence corresponds to the "antisense" sequence of HBV.

In some embodiments, the target sequence of the fifth amplification oligomer comprises position 264 or 265 of an HBV genomic nucleic acid such as SEQ ID NO: 1, e.g., positions 263-266, 258-271, 255-274, or 250-279. In some embodiments, the fifth amplification oligomer comprises a sequence having up to 1 or 2 mismatches relative to SEQ ID NO: 69. In some embodiments, the fifth amplification oligomer comprises a target-hybridizing sequence comprising positions N to 279 of an HBV nucleic acid sequence such as SEQ ID NO: 1, where N is 250, 251, 252, 253, 254, 255, 256, 257, 258, 259, 260, 261, 262, 263, 264, 265, or 266, or a sequence having up to 1 or 2 mismatches relative thereto. Various embodiments of the fifth amplification oligomer, including with respect to its sequence, are disclosed in the summary above, any of which can be combined to the extent feasible with the features discussed above in this section.

In some embodiments, a sixth amplification oligomer is provided which is a forward amplification oligomer, i.e., it is configured to hybridize specifically to (−) strand HBV nucleic acid; put another way, its target-hybridizing sequence corresponds to the "sense" sequence of HBV.

In some embodiments, the target sequence of the sixth amplification oligomer comprises position 461 or 462 of an HBV genomic nucleic acid such as SEQ ID NO: 1, e.g., positions 461-462, 457-466, 455-468, or 452-471. In some embodiments, the sixth amplification oligomer comprises a sequence having up to 1 or 2 mismatches relative to SEQ ID NO: 73. Various embodiments of the sixth amplification oligomer, including with respect to its sequence, are disclosed in the summary above, any of which can be combined to the extent feasible with the features discussed above in this section.

The fifth and sixth amplification oligomers discussed above can be used as displacers, e.g., they can facilitate amplicon production by other oligomers through extension from their 3' termini and concomitant strand displacement, making single-stranded template available for binding by other oligomers. The fifth and sixth amplification oligomers can reduce or avoid a need for a denaturation step and can enhance sensitivity.

It should be noted that the presence of, e.g., a sixth amplification oligomer does not necessarily imply the presence of all of the first, second, third, fourth, and fifth amplification oligomers. For example, it is possible to perform an exponential amplification in the presence only of first and second amplification oligomers, and either or both of the fifth and sixth amplification oligomers can be used as displacers. Additionally, a linear amplification can be performed in the presence of e.g., a promoter primer without any oppositely oriented oligomer. This note applies mutatis mutandis to other instances where ordinal numerals are used, e.g., the presence of a second capture oligomer does not necessarily imply the presence of a first capture oligomer. In some embodiments, the second, fourth, and fifth amplification oligomers are promoter primers, such that they may have any of the features of promoter primers discussed above.

In some embodiments, at least one initial amplification oligomer is provided which is different from other amplification oligomers to the extent that they are present or used, such as the second, fourth, and any additional amplification oligomers. In some embodiments, an initial amplification oligomer is provided that anneals to one or more common positions with the second amplification oligomer and has a longer target-hybridizing region than at least one or two other amplification oligomers, such as the second amplification oligomer and optionally the additional forward amplification oligomer. In some embodiments, an initial amplification oligomer is provided that anneals to one or more common positions with the fourth amplification oligomer and has a longer target-hybridizing region than the fourth amplification oligomer. As described in the examples, it was found that using an initial amplification oligomer comprising a long target-hybridizing region can improve subsequent amplification and quantification of certain HBV genotypes and thereby improve overall detection and quantification performance. The initial amplification oligomer that anneals to one or more common positions with the second amplification oligomer and the initial amplification oligomer that anneals to one or more common positions with the fourth amplification oligomer can be provided together. In some embodiments, the initial amplification oligomer(s) are in a composition with one or more target capture oligomers such as those described below or in the summary above.

In some embodiments, the target sequence of the initial amplification oligomer that anneals to one or more common positions with the second amplification oligomer comprises position 390 or 391 of an HBV genomic nucleic acid such as SEQ ID NO: 1, e.g., positions 390-391, 389-392, 388-393, 387-394, 386-395, 385-396, 384-397, 383-398, 382-399, 381-400, 380-401, 379-402, 378-403, 377-404, or 376-405. In some embodiments, the initial amplification oligomer comprises a sequence having up to 1 or 2 mismatches relative to SEQ ID NO: 20. In some embodiments, the initial amplification oligomer comprises a sequence of SEQ ID NO: 16 or 17, or a sequence having up to 1 or 2 mismatches relative thereto. In some embodiments, the initial amplification oligomer comprises a target-hybridizing sequence comprising positions N-405 of an HBV genomic sequence such as SEQ ID NO: 1, where N is 376, 377, 378, 379, 380, 381, 382, 383, 384, 385, 386, 387, 388, 389, 390, 391, or 392, or a sequence having up to 1 or 2 mismatches relative thereto. Various embodiments of the initial amplification oligomer, including with respect to its sequence, are disclosed in the summary above, any of which can be combined to the extent feasible with the features discussed above in this section. The initial amplification oligomer can also have features recited in the summary above with respect to the second amplification oligomer. For example, the initial amplification oligomer can comprise at least 11, 12, 13, 14, 15, 16, 17, 18, 19, 20, 21, 22, 23, 24, 25, 26, 27, or 28 contiguous nucleotides of SEQ ID NO: 20, or the sequence of SEQ ID NO: 20. In some embodiments, the initial amplification oligomer is a promoter-primer.

In some embodiments, the target sequence of the initial amplification oligomer that anneals to one or more common positions with the fourth amplification oligomer comprises position 659 of an HBV genomic nucleic acid such as SEQ ID NO: 1, e.g., positions 658-660, 657-661, 656-662, 655-663, 654-664, 653-665, 652-666, 651-667, 650-668, 649-670, 648-671, or 646-672. In some embodiments, the initial amplification oligomer comprises a sequence having up to 1 or 2 mismatches relative to SEQ ID NO: 35, optionally wherein the inosine at the sixth nucleotide from the 3' end of SEQ ID NO: 35 is not mismatched. In some embodiments, the initial amplification oligomer comprises a sequence of SEQ ID NO: 33 or 31, or a sequence having up to 1 or 2 mismatches relative thereto, optionally wherein the inosine at the sixth nucleotide from the 3' end of SEQ ID NO: 33 or 31 is not mismatched. In some embodiments, the initial amplification oligomer comprises a target-hybridizing sequence comprising positions N-672 of an HBV genomic sequence such as SEQ ID NO: 1, where N is 646, 647, 648, 649, 650, 651, 652, 653, 654, 655, 656, 657, 658, or 659, or a sequence having up to 1 or 2 mismatches relative thereto, optionally wherein the nucleotide corresponding to position 667 is inosine. Various embodiments of the initial amplification oligomer, including with respect to its sequence, are disclosed in the summary above, any of which can be combined to the extent feasible with the features discussed above in this section. The initial amplification oligomer can also have features recited in the summary above with respect to the fourth amplification oligomer or any amplification oligomer comprising a target-hybridizing region comprising at least 10 contiguous nucleotides of SEQ ID NO: 35. For example, the initial amplification oligomer can comprise at least 11, 12, 13, 14, 15, 16, 17, 18, 19, 20, 21, 22, 23, 24, 25, 26, 27, 28, 29, 30, 31, 32, 33, or 34 contiguous nucleotides of SEQ ID NO: 35 (optionally including the inosine at position 30 of SEQ ID NO: 35), or the sequence of SEQ ID NO: 35. In some embodiments, the initial amplification oligomer is a promoter-primer.

In some embodiments, at least one probe oligomer is provided. Some embodiments of detection probes that hybridize to complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified HBV sequences may be unlabeled and detected indirectly (e.g., by binding of another binding partner to a moiety on the probe) or may be labeled with a variety of detectable labels. A detection probe oligomer may contain a 2'-methoxy backbone at one or more linkages in the nucleic acid backbone.

In some embodiments, a detection probe oligomer in accordance with the present disclosure further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see. e.g., U.S. Pat. Nos. 6,180,340 and 6,350,579, each incorporated by reference herein). Labels may be attached to a probe by various means including covalent linkages, chelation, and ionic interactions, but in some embodiments the label is covalently attached. For example, in some embodiments, a detection probe has an attached chemiluminescent label such as, e.g., an acridinium ester (AE) compound (see. e.g., U.S. Pat. Nos. 5,185,439; 5,639,604; 5,585,481; and 5,656,744; each incorporated by reference herein), which in typical variations is attached to the probe by a non-nucleotide linker (see. e.g., U.S. Pat. Nos. 5,585,481; 5,656,744; and 5,639,604, each incorporated by reference herein).

A detection probe oligomer in accordance with the present disclosure may further include a non-target-hybridizing sequence. In some applications, probes exhibiting at least some degree of self-complementarity are desirable to facilitate detection of probe:target duplexes in a test sample without first requiring the removal of unhybridized probe prior to detection. Specific embodiments of such detection probes include, for example, probes that form conformations held by intramolecular hybridization, such as conformations generally referred to as hairpins. Particularly suitable hairpin probes include a "molecular torch" (see. e.g., U.S. Pat. Nos. 6,849,412; 6,835,542; 6,534,274; and 6,361,945, each incorporated by reference herein) and a "molecular beacon" (see. e.g., Tyagi et al., supra; U.S. Pat. Nos. 5,118,801 and 5,312,728, supra). In yet other embodiments, a detection probe is a linear oligomers that does not substantially form conformations held by intramolecular bonds.

By way of example, structures referred to as "molecular beacons" comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference. Molecular beacons useful for detecting HBV specific nucleic acid sequences may be created by appending to either end of one of the probe (e.g., target-hybridizing) sequences disclosed herein, a first nucleic acid arm comprising a fluorophore and a second nucleic acid arm comprising a quencher moiety. In this configuration, the HBV specific probe sequence disclosed herein serves as the target-complementary "loop" portion of the resulting molecular beacon, while the self-complementary "arms" of the probe represent the "stem" portion of the probe.

Another example of a self-complementary hybridization assay probe that may be used in conjunction with the disclosure is a structure commonly referred to as a "molecular torch" (sometimes referred to simply as a torch). These self-reporting probes are designed to include distinct regions of self-complementarity (coined "the target binding domain" and "the target closing domain") which are connected by a joining region (e.g., a —$(CH_2)_9$— linker) and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference.

Molecular torches and molecular beacons in some embodiments are labeled with an interactive pair of detectable labels. Examples of detectable labels that are members of an interactive pair of labels include those that interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Exemplary label moieties for the disclosed molecular torches and molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are In some embodiments due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the disclosure, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL and the BLACK HOLE QUENCHER moieties which are available from Biosearch Technologies, Inc., (Novato, Calif.).

Oligomers that are not intended to be extended by a nucleic acid polymerase, e.g., probe oligomers and capture oligomers, can include a blocker group that replaces the 3' OH to prevent enzyme-mediated extension of the oligomer in an amplification reaction. For example, blocked amplification oligomers and/or detection probes present during amplification in some embodiments do not have a functional 3' OH and instead include one or more blocking groups located at or near the 3' end. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

While oligonucleotide probes of different lengths and base composition may be used for detecting HBV nucleic acids, some embodiments of probes in this disclosure are from 10 to 60 bases in length, or between 14 and 50 bases in length, or between 15 and 30 bases in length. A first probe oligomer can be provided that is configured to specifically hybridize to the first amplicon discussed above. Alternatively or in addition, a second probe oligomer can be provided that is configured to specifically hybridize to the first amplicon discussed above.

In some embodiments, the target sequence of the first probe oligomer comprises position 424 of an HBV genomic nucleic acid such as SEQ ID NO: 1, e.g., positions 423-425, 421-427, 419-429, 417-431, 415-433, 413-435, 411-437, 410-438, 409-439, or 408-440. In some embodiments, the probe oligomer comprises a sequence having up to 1 or 2 mismatches relative to SEQ ID NO: 82. In some embodiments, the probe oligomer comprises a sequence of SEQ ID NO: 29, or a sequence having up to 1 or 2 mismatches relative thereto. Various embodiments of the probe oligomer, including with respect to its sequence, are disclosed in the summary above, any of which can be combined to the extent feasible with the features discussed above in this section.

In some embodiments, the target sequence of the second probe oligomer comprises position 675 or 676 of an HBV genomic nucleic acid such as SEQ ID NO: 1, e.g., positions 675-676, 674-677, 673-678, 672-679, 671-680, 670-681, 669-682, or 668-683. In some embodiments, the probe oligomer comprises a sequence having up to 1 or 2 mismatches relative to SEQ ID NO: 83. In some embodiments, the probe oligomer comprises a sequence of SEQ ID NO: 84, 85, 40, or a sequence having up to 1 or 2 mismatches relative thereto. Various embodiments of the probe oligomer, including with respect to its sequence, are disclosed in the summary above, any of which can be combined to the extent feasible with the features discussed above in this section.

In some embodiments, at least one capture oligomer is provided, e.g., two, three, or four capture oligomers. It is understood that when two or more capture oligomers are present, their target-hybridizing sequences are different from each other. The one or more capture oligomers comprise a target-hybridizing sequence configured to specifically hybridize to HBV nucleic acid, e.g., from 10 to 60 bases in length, or between 14 and 50 bases in length, or between 15 and 30 bases in length. For example, in specific embodiments of capture probes, the one, two, three, or four capture probes have target-hybridizing sequences selected from SEQ ID NO: 49, 53, 57, 61, and 96-104. The target-hybridizing sequence is covalently attached to a sequence or moiety that binds to an immobilized probe, e.g., an oligomer attached to a solid substrate, such as a bead.

In more specific embodiments, the capture oligomer includes a tail portion (e.g., a 3' tail) that is not complementary to the HBV target sequence but that specifically hybridizes to a sequence of the immobilized binding partner (e.g., immobilized probe), thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and certain embodiments include a substantially homopolymeric tail ("poly-N sequence") of at least about 10 nt, e.g., about 10 to 40 nt (e.g., $A_{10}$ to $A_{40}$), such as about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. For example, in specific embodiments of a capture probe comprising a 3' tail, the one, two, three, or four capture probes have sequences selected from SEQ ID NO: 45, 46, 47, and 48.

In some embodiments, a first capture oligomer is provided. In some embodiments, the target sequence of the first capture oligomer comprises position 719 of an HBV genomic nucleic acid such as SEQ ID NO: 1, e.g., positions 718-720, 716-722, 714-724, 712-726, 710-728, 709-729, 708-730, or 707-731. In some embodiments, the first capture oligomer comprises a sequence having up to 1 or 2 mismatches relative to SEQ ID NO: 49. In some embodiments, the first capture oligomer comprises a sequence having up to 1 or 2 mismatches relative to SEQ ID NO: 99. In some embodiments, the first capture oligomer comprises a sequence having up to 1 or 2 mismatches relative to SEQ ID NO: 45. Various embodiments of the first capture oligomer, including with respect to its sequence, are disclosed in the summary above, any of which can be combined to the extent feasible with the features discussed above in this section.

In some embodiments, a second capture oligomer is provided. In some embodiments, the target sequence of the second capture oligomer comprises position 745 of an HBV genomic nucleic acid such as SEQ ID NO: 1, e.g., positions 744-746, 742-748, 740-750, 738-752, 736-754, 735-755, 734-756, or 733-757. In some embodiments, the second capture oligomer comprises a sequence having up to 1 or 2 mismatches relative to SEQ ID NO: 53. In some embodiments, the second capture oligomer comprises a sequence having up to 1 or 2 mismatches relative to SEQ ID NO: 100, 101, or 104. In some embodiments, the second capture oligomer comprises a sequence having up to 1 or 2 mismatches relative to SEQ ID NO: 46. Various embodiments of the second capture oligomer, including with respect to its sequence, are disclosed in the summary above, any of which can be combined to the extent feasible with the features discussed above in this section.

In some embodiments, a third capture oligomer is provided. In some embodiments, the target sequence of the third capture oligomer comprises position 1180 or 1181 of an HBV genomic nucleic acid such as SEQ ID NO: 1, e.g., positions 1180-1181, 1178-1183, 1176-1185, 1174-1187, 1172-1189, 1170-1191, 1169-1192, or 1168-1193. In some embodiments, the third capture oligomer comprises a sequence having up to 1 or 2 mismatches relative to SEQ ID NO: 57. In some embodiments, the third capture oligomer comprises a sequence having up to 1 or 2 mismatches relative to SEQ ID NO: 96. In some embodiments, the third capture oligomer comprises a sequence having up to 1 or 2 mismatches relative to SEQ ID NO: 102 In some embodiments, the third capture oligomer comprises a sequence having up to 1 or 2 mismatches relative to SEQ ID NO: 47. Various embodiments of the third capture oligomer, including with respect to its sequence, are disclosed in the summary above, any of which can be combined to the extent feasible with the features discussed above in this section.

In some embodiments, a fourth capture oligomer is provided. In some embodiments, the target sequence of the fourth capture oligomer comprises position 1303 of an HBV genomic nucleic acid such as SEQ ID NO: 1, e.g., positions 1302-1304, 1300-1306, 1298-1308, 1296-1310, 1294-1312, 1292-1314, 1291-1315, or 1290-1316. In some embodiments, the fourth capture oligomer comprises a sequence having up to 1 or 2 mismatches relative to SEQ ID NO: 61. In some embodiments, the fourth capture oligomer comprises a sequence having up to 1 or 2 mismatches relative to SEQ ID NO: 97, 98, or 103. In some embodiments, the fourth capture oligomer comprises a sequence having up to 1 or 2 mismatches relative to SEQ ID NO: 48. Various embodiments of the fourth capture oligomer, including with respect to its sequence, are disclosed in the summary above, any of which can be combined to the extent feasible with the features discussed above in this section.

Internal control oligomers can be provided, e.g., for confirming that a negative result is valid by establishing that conditions were suitable for amplification. An exemplary control target capture oligomer is SEQ ID NO: 80. Exemplary control amplification oligomers are SEQ ID NOs: 77 and 78. An exemplary control probe oligomer is SEQ ID NO:79. A control template that can be amplified by the control amplification oligomers can also be provided. Control templates may be prepared according to known protocols. See, e.g., U.S. Pat. No. 7,785,844, which is incorporated herein by reference, and which describes an internal control consisting of an in vitro synthesized transcript containing a portion of HIV-1 sequence and a unique sequence targeted by the internal control probe.

In certain aspects of the disclosure, a combination of at least two oligomers is provided for determining the presence or absence of HBV or quantifying HBV in a sample. In some embodiments, the oligomer combination includes at least two amplification oligomers suitable for amplifying a target region of an HBV target nucleic acid, e.g., having the sequence of SEQ ID NO: 1 or 105-125, or any HBV isolate or construct referred to in the examples or for which an accession number is provided herein. In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS are each configured to specifically hybridize to a target sequence within an HBV sequence. It is understood that the target-hybridizing sequences are selected such that the HBV sequence targeted by antisense THS is situated downstream of the HBV sequence targeted by the sense THS (i.e., the at least two amplification oligomers are situated such that they flank the target region to be amplified).

The oligomers can be provided in various combinations (e.g., kits or compositions), e.g., comprising 2, 3, 4, 5, 6, 7, 8, 9, 10, 11, 12, 13, 14, 15, or 16 of a first amplification oligomer, additional reverse amplification oligomer, second amplification oligomer, additional forward amplification oligomer, third amplification oligomer, fourth amplification oligomer, fifth amplification oligomer, sixth amplification oligomer, initial amplification oligomer that anneals to one or more common positions with the second amplification oligomer, initial amplification oligomer that anneals to one or more common positions with the fourth amplification oligomer, first probe oligomer, second probe oligomer, first capture oligomer, second capture oligomer, third capture oligomer, and fourth capture oligomer, such as at least one initial amplification oligomer and at least one capture oligomer, a first capture oligomer and second capture oligomer, optionally further comprising at least one initial amplification oligomer, a first capture oligomer and third capture oligomer, optionally further comprising at least one initial amplification oligomer; a first capture oligomer and fourth capture oligomer, optionally further comprising at least one initial amplification oligomer, a second capture oligomer and third capture oligomer, optionally further comprising at least one initial amplification oligomer, a second capture oligomer and fourth capture oligomer, optionally further comprising at least one initial amplification oligomer, a third capture oligomer and fourth capture oligomer, optionally further comprising at least one initial amplification oligomer, a first amplification oligomer and a second amplification oligomer, optionally further comprising a first probe oligomer, a first, second, and additional reverse amplification oligomer, optionally further comprising a first probe oligomer, a first, second, and additional forward amplification oligomer, optionally further comprising a first probe oligomer, a first, second, additional forward, and additional reverse amplification oligomer, optionally further comprising a first probe oligomer, an initial amplification oligomer that anneals to one or more common positions with the second amplification oligomer, at least one capture oligomer, a first amplification oligomer, and a second amplification oligomer, optionally further comprising a first probe oligomer, an initial amplification oligomer that anneals to one or more common positions with the second amplification oligomer, at least two capture oligomers, a first amplification oligomer, and a second amplification oligomer, optionally further comprising a first probe oligomer, a third amplification oligomer and a fourth amplification oligomer, optionally further comprising a second probe oligomer, a third amplification oligomer, fourth amplification oligomer, and an initial amplification oligomer that anneals to one or more common positions with the fourth amplification oligomer, optionally further comprising a second probe oligomer, a third amplification oligomer, fourth amplification oligomer, an initial amplification oligomer that anneals to one or more common positions with the fourth amplification oligomer, and at least one capture oligomer, optionally further comprising a second probe oligomer, an initial amplification oligomer that anneals to one or more common positions with the second amplification oligomer, at least two capture oligomers, a first amplification oligomer, and a second amplification oligomer, optionally further comprising a first probe oligomer, an initial amplification oligomer that anneals to one or more common positions with the second amplification oligomer, at least one capture oligomer, a first amplification oligomer, a second amplification oligomer, a third amplification oligomer, and a fourth amplification oligomer, optionally further comprising a third and/or fourth capture oligomer, or an initial amplification oligomer that anneals to one or more common positions with the second amplification oligomer, an initial amplification oligomer that anneals to one or more common positions with the fourth amplification oligomer, at least one capture oligomer, a first amplification oligomer, a second amplification oligomer, a third amplification oligomer, and a fourth amplification oligomer, optionally further comprising first and second probe oligomers. Combinations can further comprise a control oligomer or combination thereof e.g., two control amplification oligomers, a control target capture oligomer, and/or a control probe oligomer. In some embodiments, both first and second amplification oligomers are present. In some embodiments, both initial and third amplification oligomers are present.

In some embodiments, a combination does not comprise more than 17, 16, 15, 14, 13, 12, 11, 10, or 9 distinct oligomers, not including control oligomers. In such embodiments, variants present in trace amounts (e.g., about 15 mol % or less or about 10 mol % or less relative to a major species of oligomer, such as the oligomer with the most similar sequence to the variant), such as may result from misincorporation, double incorporation, omission, or other errors during oligomer synthesis, are not considered a distinct oligomer.

In some embodiments, a combination of oligomers is provided as described below in any of the examples or individual reactions described in the examples.

In some embodiments, a combination of oligomers, e.g., in a kit or composition, is configured to specifically hybridize to nucleic acid of at least three, four, five, six, seven, eight, or nine HBV genotypes (e.g., types A, B, C, C2, D, E, F, G, or H)), optionally with minimal cross-reactivity to other, non-HBV nucleic acids suspected of being in a sample (e.g., other bloodborne pathogens, such one or more, or all, of the microorganisms and/or bloodborne viruses listed in Table 8). In some embodiments, a combination of oligomers can be used to quantify such strains within 1 log of HBV A. In some embodiments, a combination of oligomers can be used to quantify such strains within 0.5 log of HBV A. In some aspects, the compositions of the instant disclosure are configured to specifically hybridize to HBV nucleic acid with minimal cross-reactivity to one or more, or all, of Hepatitis A, Rubella, Hepatitis C, Herpes simplex 1, Herpes simplex 2, HIV2, Parvovirus, Dengue, CMV, HTLV, Epstein-Barr, and West Nile viruses. In some embodiments, the compositions of the instant disclosure are configured to specifically hybridize to HBV nucleic acid with minimal cross-reactivity to one or more, or all, of *C. albicans, P. acnes, S. aureus, S. epidermis*, or *N. gonorrhoeae*. In one aspect, the compositions of the instant disclosure are part of a multiplex system that further includes components and methods for detecting one of more of these organisms.

Also provided by the disclosure is a reaction mixture for determining the presence or absence of an HBV target nucleic acid or quantifying the amount thereof in a sample. A reaction mixture in accordance with the present disclosure comprises at least one or more of the following: an oligomer combination as described herein for amplification of an HBV target nucleic acid; a capture probe oligomer as described herein for purifying the HBV target nucleic acid; and a detection probe oligomer as described herein for determining the presence or absence of an HBV amplification product. In some embodiments, any oligomer combination described above is present in the reaction mixture. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which an HBV target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject disclosure are kits for practicing the methods as described herein. A kit in accordance with the present disclosure comprises at least one or more of the following: an amplification oligomer combination as described herein for amplification of an HBV target nucleic acid; at least one capture probe oligomer as described herein for purifying the HBV target nucleic acid; and at least one detection probe oligomer as described herein for determining the presence or absence of an HBV amplification product. In some embodiments, any oligomer combination described above is present in the kit. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the disclosure embraces many different kit configurations. For example, a kit may include amplification oligomers for only one target region of an HBV genome, or it may include amplification oligomers for multiple HBV target regions, such as for producing first and second amplicons as described above. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods

C. Methods and Uses

Any method disclosed herein is also to be understood as a disclosure of corresponding uses of materials involved in the method directed to the purpose of the method. Any of the oligomers comprising HBV sequence and any combinations (e.g., kits and compositions) comprising such an oligomer are to be understood as also disclosed for use in detecting or quantifying HBV, and for use in the preparation of a composition for detecting or quantifying HBV.

Broadly speaking methods can comprise one or more of the following components: target capture, in which HBV nucleic acid is annealed to a capture oligomer and optionally to an initial amplification oligomer, isolation, e.g., washing, to remove material not associated with a capture oligomer, linear amplification; exponential amplification; and amplicon detection, e.g., amplicon quantification, which may be performed in real time with exponential amplification. Certain embodiments involve each of the foregoing steps. Certain embodiments involve exponential amplification without linear amplification. Certain embodiments involve washing, isolation, and linear amplification. Certain embodiments involve exponential amplification and amplicon detection. Certain embodiments involve any two of the components listed above. Certain embodiments involve any two components listed adjacently above, e.g., washing and linear amplification, or linear amplification and exponential amplification.

In some embodiments, amplification comprises contacting the sample with at least two oligomers for amplifying an HBV nucleic acid target region corresponding to an HBV target nucleic acid, where the oligomers include at least two amplification oligomers as described above (e.g., one or more oriented in the sense direction and one or more oriented in the antisense direction for exponential amplification); (2) performing an in vitro nucleic acid amplification reaction, where any HBV target nucleic acid present in the sample is used as a template for generating an amplification product; and (3) detecting the presence or absence of the amplification product, thereby determining the presence or absence of HBV in the sample, or quantifying the amount of HBV nucleic acid in the sample.

In some embodiments, amplification comprises contacting the sample with at least four oligomers for amplifying an HBV nucleic acid target region corresponding to an HBV target nucleic acid, where the oligomers include at least two amplification oligomers for producing a first amplicon as described above (e.g., one or more oriented in the sense direction and one or more oriented in the antisense direction for exponential amplification) and at least two amplification oligomers for producing a second amplicon as described above (e.g., one or more oriented in the sense direction and one or more oriented in the antisense direction for exponential amplification); (2) performing an in vitro nucleic acid amplification reaction, where any HBV target nucleic acid present in the sample is used as a template for generating an amplification product; and (3) detecting the presence or absence of the first or second amplicons, thereby determining the presence or absence of HBV in the sample, or quantifying the amount of HBV nucleic acid in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the HBV target nucleic acid from other components in the sample, e.g., before an amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains HBV nucleic acid and other sample components.

Target capture typically occurs in a solution phase mixture that contains one or more capture probe oligomers that hybridize specifically to the HBV target sequence under hybridizing conditions, usually at a temperature higher than the $T_m$ of the tail-sequence:immobilized-probe-sequence duplex. For embodiments comprising a capture probe tail, the HBV-target:capture-probe complex is captured by adjusting the hybridization conditions so that the capture probe tail hybridizes to the immobilized probe. Certain embodiments use a particulate solid support, such as paramagnetic beads.

Isolation can follow capture, wherein the complex on the solid support is separated from other sample components. Isolation can be accomplished by any appropriate technique, e.g., washing a support associated with the HBV-target-sequence one or more times (e.g., 2 or 3 times) to remove other sample components and/or unbound oligomer. In embodiments using a particulate solid support, such as paramagnetic beads, particles associated with the HBV-target may be suspended in a washing solution and retrieved from the washing solution, In some embodiments by using magnetic attraction. To limit the number of handling steps, the HBV target nucleic acid may be amplified by simply mixing the HBV target sequence in the complex on the support with amplification oligomers and proceeding with amplification steps.

Linear amplification can be performed, e.g., by contacting the target nucleic acid sequence with a first phase amplification reaction mixture that supports linear amplification of the target nucleic acid sequence and lacks at least one component that is required for its exponential amplification. In some embodiments, the first phase amplification reaction mixture includes an amplification enzyme selected from a reverse transcriptase, a polymerase, and a combination thereof. The polymerase is typically selected from an RNA-dependent DNA polymerase, a DNA-dependent DNA polymerase, a DNA-dependent RNA polymerase, and a combination thereof. In some embodiments, the first phase amplification reaction mixture further includes a ribonuclease (RNase), such as an RNase H or a reverse transcriptase with an RNase H activity. In some embodiments, the first phase amplification mixture includes a reverse transcriptase with an RNase H activity and an RNA polymerase.

In some embodiments, the first phase amplification mixture may also include an amplification oligonucleotide. The amplification oligonucleotide can include a 5' promoter sequence for an RNA polymerase, such as T7 RNA polymerase, and/or a blocked 3' terminus that prevents its enzymatic extension. In addition, the first phase amplification mixture may sometimes include a blocker oligonucleotide to prevent enzymatic extension of the target nucleic sequence beyond a desired end-point.

As noted above, the key feature of the first phase amplification reaction is its inability to support an exponential amplification reaction because one or more components required for exponential amplification are lacking, and/or an agent is present which inhibits exponential amplification, and/or the temperature of the reaction mixture is not conducive to exponential amplification, etc. Without limitation, the lacking component required for exponential amplification and/or inhibitor and/or reaction condition may be selected from the following group: an amplification oligonucleotide (e.g., an amplification oligonucleotide comprising a 5' promoter sequence for an RNA polymerase, a non-promoter amplification oligonucleotide, or a combination thereof), an enzyme (e.g., a polymerase, such as an RNA polymerase), a nuclease (e.g., an exonuclease, an endonuclease, a cleavase, an RNase, a phosphorylase, a glycosylase, etc), an enzyme co-factor, a chelator (e.g., EDTA or EGTA), ribonucleotide triphosphates (rNTPs), deoxyribonucleotide triphosphates (dNTPs), $Mg^{2+}$, a salt, a buffer, an enzyme inhibitor, a blocking oligonucleotide, pH, temperature, salt concentration and a combination thereof. In some cases, the lacking component may be involved indirectly, such as an agent that reverses the effects of an inhibitor of exponential amplification which is present in the first phase reaction.

Exponentially amplifying an HBV target sequence utilizes an in vitro amplification reaction using at least two amplification oligomers that flank a target region to be amplified.

In some embodiments, at least first and second amplification oligomers as described above are provided. In particular embodiments, the target region to be amplified substantially corresponds to a region of SEQ ID NO: 1 including nucleotide position 417 or 418, e.g., about positions 415-420, 410-425, 405-430, 400-435, 395-440, 390-445, 385-450, 380-455, or 376-459 (including oligomer sequences incorporated into the amplification product).

In some embodiments, at least third and fourth amplification oligomers as described above are provided. In particular embodiments, the target region to be amplified substantially corresponds to a region of SEQ ID NO: 1 including nucleotide position 677, e.g., about positions 675-679, 670-684, 665-689, 660-694, 655-699, 650-704, or 646-708 (including oligomer sequences incorporated into the amplification product).

Particularly suitable amplification oligomer combinations for amplification of these target regions are described above. In some embodiments, the target regions flanked by the first and second amplification oligomers and by the third and fourth amplification oligomers are amplified in the same reaction mixture. Suitable amplification methods include, for example, replicase-mediated amplification, polymerase chain reaction (PCR), ligase chain reaction (LCR), strand-displacement amplification (SDA), and transcription-mediated or transcription-associated amplification (TMA).

For example, some amplification methods that use TMA amplification include the following steps. Briefly, the target nucleic acid that contains the sequence to be amplified is provided as single-stranded nucleic acid (e.g., ssRNA such as HBV RNA). Those skilled in the art will appreciate that, alternatively, DNA can be used in TMA; conventional melting of double stranded nucleic acid (e.g., dsDNA) may be used to provide single-stranded target nucleic acids. A promoter primer (e.g., a third amplification oligomer comprising a promoter as described above) binds specifically to the target nucleic acid at its target sequence and a reverse transcriptase (RT) extends the 3' end of the promoter primer using the target strand as a template to create a cDNA extension product, resulting in an RNA:DNA duplex if ssRNA was the original template. An RNase digests the RNA strand of the RNA:DNA duplex and a second primer binds specifically to its target sequence, which is located on the cDNA strand downstream from the promoter primer end. RT synthesizes a new DNA strand by extending the 3' end of the other primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the other primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The other or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above in the preceding paragraph for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see. e.g., U.S. Pat. Nos. 5,639,604 and 5,283,174, each incorporated by reference herein). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the HBV genomic RNA, and a probe will bind directly or indirectly to a sequence contained in the amplified product to indicate the presence of HBV nucleic acid in the tested sample.

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

In some embodiments, a molecular torch (sometimes referred to simply as a torch) is used for detection. In some embodiments, the torch is a probe oligomer as disclosed above.

In general, the disclosed methods can involve the step of consulting a standard curve that relates pre-amplification amounts of analyte polynucleotide and post-amplification amounts of analyte amplicon.

Since real-time amplification reactions advantageously feature quantitative relationships between the number of analyte polynucleotides input into the reaction and the number of analyte amplicons synthesized as a function of time, the number of analyte polynucleotides present in a test sample can be determined using a standard curve. For example, a plurality of amplification reactions containing known amounts of a polynucleotide standard can be run in parallel with an amplification reaction prepared using a test sample containing an unknown number of analyte polynucleotides. Alternatively, a standard curve can be prepared in advance so that it is unnecessary to prepare a curve each time an analytical procedure is carried out. Such a curve prepared in advance can even be stored electronically in a memory device of a testing instrument. A standard curve having pre-amplification amounts of the polynucleotide standard on a first axis and some indicia of the time required to effect a certain level of nucleic acid amplification (such as a time-of-emergence above a background signal) on a second axis is then prepared. The post-amplification amount of analyte amplicon measured for the test reaction is then located on the post-amplification axis of the standard curve. The corresponding value on the other axis of the curve represents the pre-amplification amount of analyte polynucleotide that was present in the test reaction. Thus, determining the number of molecules of analyte polynucleotide present in the test sample is accomplished by consulting the standard curve, or more particularly by comparing the quantitative results obtained for the test sample with the standard curve, a procedure that will be familiar to those having an ordinary level of skill in the art.

The procedures described herein can easily be used to quantify analyte polynucleotides (e.g., HBV nucleic acid) present in a test sample. Indeed, if a plurality of standard control amplification reactions are initiated using known numbers of an analyte polynucleotide standard, and if a test reaction that includes an unknown number of analyte polynucleotide molecules is carried out, then it becomes possible after measuring the time required to effect a certain level of amplification in each reaction to determine the number of analyte polynucleotide molecules that must have been present in the test sample. The relationship between the number of analyte polynucleotide molecules input into standard amplification reaction and the time required to effect a certain level of amplification is conveniently established using a graph. Determining the number of analyte polynucleotide molecules present in a test sample is simply a matter of determining from the standard graph the number of analyte polynucleotide molecules that correspond to a measured analyte amplicon signal strength. This illustrates how analyte polynucleotide standards can be used in connection with polynucleotide amplification reactions to quantify pre-amplification amounts of analyte polynucleotide contained in test samples.

In some embodiments, quantification is performed based on one or both of first and second amplicons such as those discussed above. In some embodiments, levels of the first and second amplicons are determined, e.g., based on signals from first and second probe oligomers (e.g., labeled probe oligomers) configured to specifically hybridize to the first and second amplicons, respectively. The levels can be compared to a predetermined threshold to determine how to proceed with determining a level of HBV nucleic acid in the sample. For example, if one or both of the levels is about equal to or above the predetermined threshold, then the higher of the levels can be used to determine the level of HBV nucleic acid in the sample. On the other hand, if one or both of the levels is below the predetermined threshold, then the average of the levels can be used to determine the level of HBV nucleic acid in the sample. In some embodiments, the average is an arithmetic mean (e.g., 20 copies/ml based on first and second levels of 10 and 30 copies/ml). In some embodiments, the average is a geometric mean (e.g., 1.2 log copies/ml based on first and second levels of 1.1 and 1.3 log copies/ml).

Levels can be expressed in various ways, e.g., as concentrations, absolute numbers of copies, mass, emergence time, or RLU or RFU. Levels can be logarithmic or arithmetic. Levels can be converted between different forms of expression. For example, RFU versus time can be converted to an emergence time, and emergence time can be converted to a logarithmic value using a calibration curve. As a further example, the logarithmic value can be converted to an arithmetic value. In some embodiments, a calibration curve or other appropriate standard is used to aid in comparing a level to a predetermined threshold.

In some embodiments, the predetermined threshold is at a value where expected instrument error is greater than or about equal to expected error due to a point mutation, or at a value where expected error due to a point mutation is greater than or about equal to expected random error. Random error represents the variation that occurs between replicate measurements due to sources of error such as variability in biochemical processes, sample and reagent handling, and instrument performance. In some embodiments, the predetermined threshold is within about 50 IU/ml, 40 IU/ml, 30 IU/ml, 20 IU/ml, or 10 IU/ml of the value where expected instrument error is equal to expected error due to a point mutation. In some embodiments, the predetermined threshold is within about 1, 0.5, or 0.25 log IU/ml of the value where expected instrument error is equal to expected error due to a point mutation. The expected errors can be determined using control experiments, e.g., replicates for instrument error and a comparison of point mutants to HBV nucleic acid without the mutation for expected error due to a point mutation.

Using a predetermined threshold near the value where expected random error is about equal to expected error due to a point mutation can be beneficial in that when amplicon levels are both below the value, it is likely that random error is the primary source of variability and averaging is likely to reduce total error. On the other hand, when at least one amplicon level is above the value, mutations are more likely to be the primary source of variability such that using the higher measured level is likely to reduce total error.

Exemplary predetermined thresholds are provided in the summary above in terms of IU/ml values, which are understood to be convertible to other forms as discussed above, including copies/ml, log copies/ml, emergence time, etc. Additionally, depending on the instrument used, alternative values for the predetermined threshold may be desirable.

In some embodiments, a method or use can provide substantially equivalent quantification (e.g., within 1, 0.5, or 0.25 logs) of at least three, four, five, six, seven, eight, or nine HBV genotypes (e.g., genotypes A, B, C, C2, D, E, F, G, or H), optionally with minimal cross-reactivity to other, non-HBV nucleic acids suspected of being in a sample (e.g., other bloodborne pathogens). In some aspects, the methods Hepatitis A, Rubella, Hepatitis C, Herpes simplex 1, Herpes simplex 2, HIV2, Parvovirus, Dengue, CMV, HTLV, Epstein-Barr, and West Nile viruses. In some embodiments, the the methods and uses of the instant disclosure show minimal cross-reactivity to one or more, or all, of *C. albicans, P. acnes, S. aureus, S. epidermis,* or *N. gonorrhoeae*. In one aspect, the methods and uses of the instant disclosure are multiplexed with methods for detecting one of more of the foregoing viruses or microbes. In general, minimal cross-reactivity is understood as showing at least about 95% specificity, e.g., at least about 96%, 97%, 98%, or 99%.

EXAMPLES

The following examples are provided to illustrate certain disclosed embodiments and are not to be construed as limiting the scope of this disclosure in any way.

General Reagents and Methods.

Unless otherwise indicated, amplifications were performed isothermally using transcription-mediated amplification with T7 RNA polymerase and reverse transcriptase. Biphasic TMA was carried out essentially as described in U.S. Pat. No. 9,139,870, which is incorporated herein by reference. In general, the last primer added in the biphasic procedures was the T7 primer for each amplicon to be produced, or the shorter T7 primer(s) for each amplicon to be produced where a combination of two or more different T7 primer sequences were used. Exemplary amplification oligomers include those having the sequences of SEQ ID NOs: 2, 3, 14, 15, 30, and 41.

Amplification reactions were conducted for various primer combinations using about 5 to 10 pmoles per reaction of T7 primer and nonT7 primer.

Detection used molecular torches as probe oligomers which contained a 5'-fluorophore (e.g., FAM or ROX) and a 3'-quencher (e.g., DABCYL) ("5F3D" for FAM and DABCYL or "5R3D" for ROX and DABCYL). Torches are discussed in detail in U.S. Pat. No. 6,849,412, which is incorporated by reference. Torches generally contained a —$(CH_2)_9$— linker near the 3'-end (e.g., between the $5^{th}$ and $6^{th}$ or between the $4^{th}$ and $5^{th}$ nucleotides from the 3'-end). Exemplary probe oligomers include those having the sequences of SEQ ID NOs: 29 and 40. Target capture was performed essentially as described in U.S. Pat. No. 8,034,554, which is incorporated herein by reference. Exemplary target capture oligomers include those having the sequences of SEQ ID NOs: 45-48 and 87-95.

Exemplary internal control oligomers and template are discussed in U.S. Pat. No. 7,785,844, which is incorporated herein by reference.

Unless otherwise indicated, "HBV database" sequences are from a database of approximately 4300 HBV isolate sequences obtained from human donors.

Example 1—Target Capture

Target capture was performed with various exemplary target capture oligomers (TCOs) selected from TCOs having a sequence of SEQ ID NO: 45-48 or 87-95 singly and in combination in the presence of initial amplification oligomers (see Example 2), followed by washing linear amplification, exponential amplification, and detection. A copy-to-IU conversion factor of 5 copies/IU was used. Without any addition of TCO, the sensitivity was about 4% or less when 2 IU/mL of WHO standard HBV virus was tested in serum, compared to the sensitivity of up to about 89% when a combination of multiple TCOs was used. Use of various single TCOs gave a sensitivity in the range of about 30-60%. This shows a benefit that can be provided by using multiple exemplary TCOs.

Example 2—Initial Amplification Oligomers

Figures 4A, 4B:
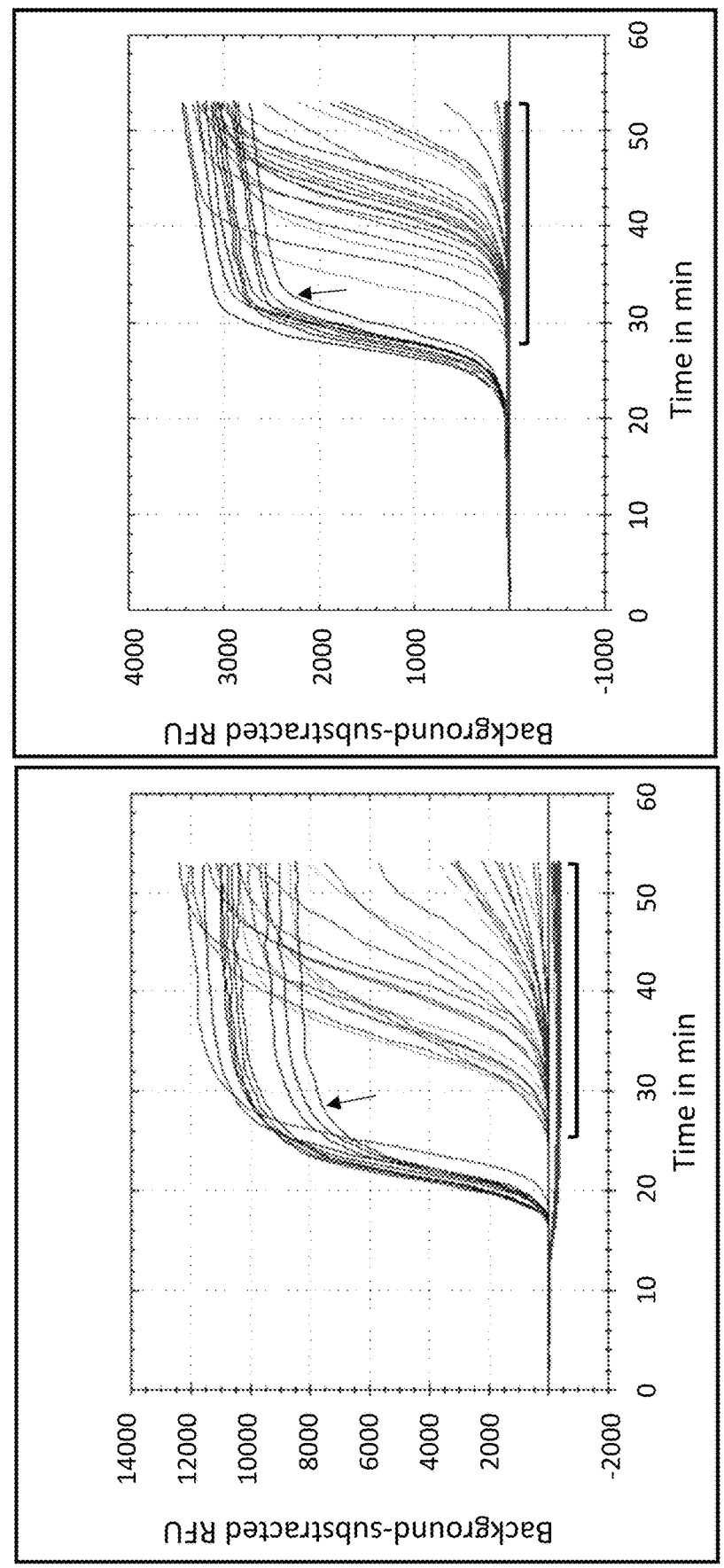
FIGS. 4A-D show emergence curves for experiments in the absence (A-B) and presence (C-D) of initial amplification oligomers A376 and A35.
Figure 4C:
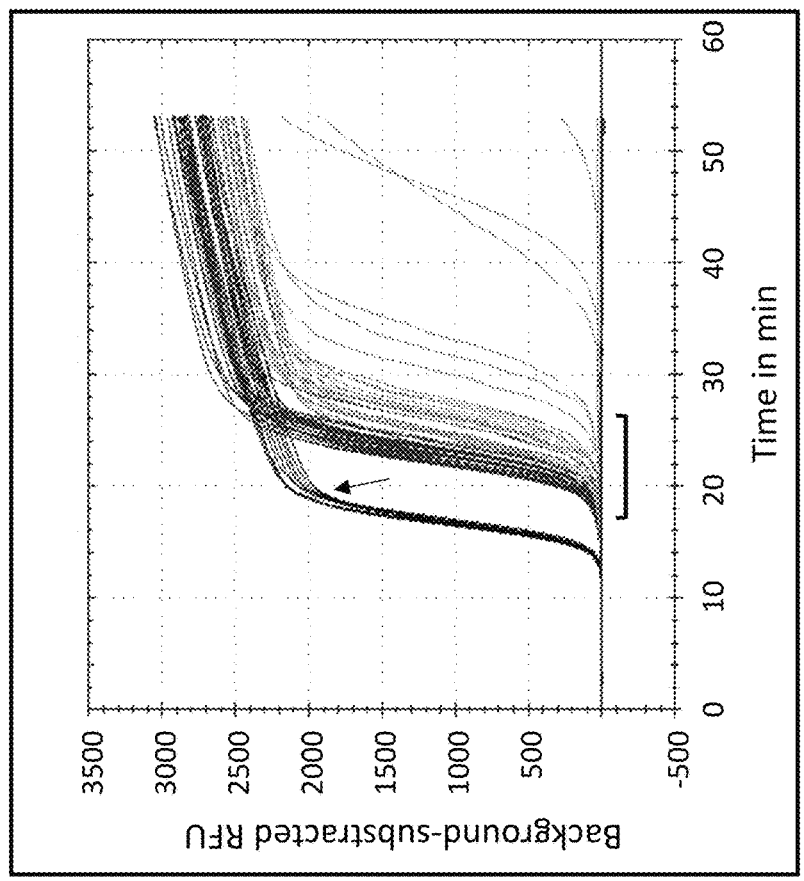
Figure 4D:
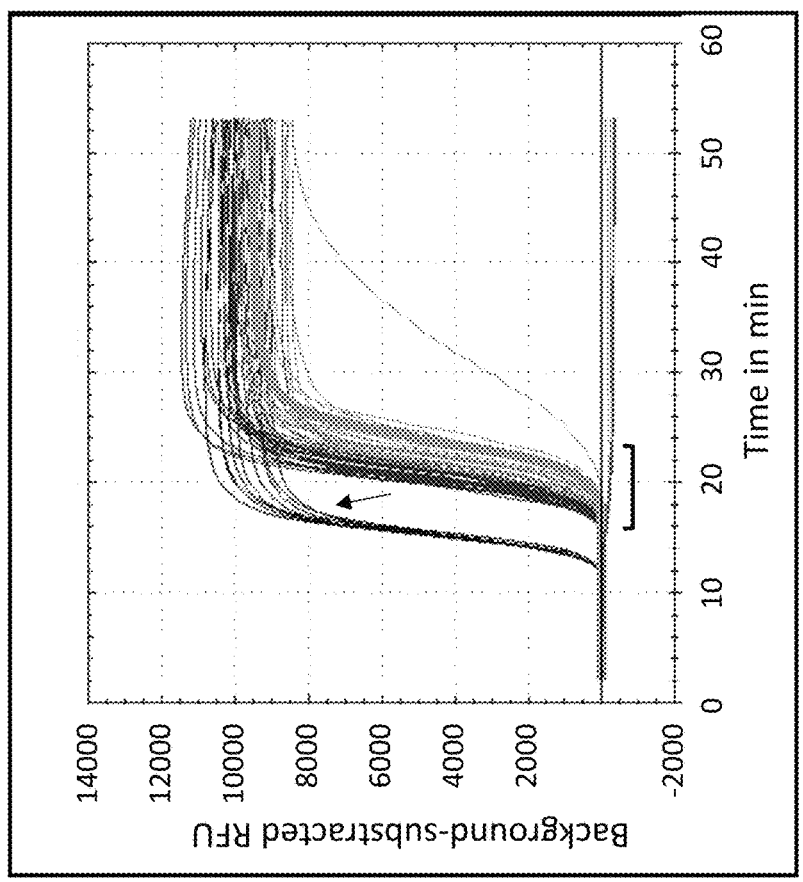

The functionality of T7 initial amplification oligomers was demonstrated as follows. HBV nucleic acid concentrations of 2 IU/ml, 10 IU/ml, and 2000 IU/ml were used as starting material in capture-amplification reactions. Target capture was performed with a combination of TCOs selected from TCOs having a sequence of SEQ ID NO: 45-48 or 87-95, followed by washing, linear amplification, exponential amplification, and detection. Initial amplification oligomers were omitted in the experiments whose results appear in FIGS. 4A-B. Accordingly, linear amplification is not believed to have occurred in the experiments represented in FIGS. 4A-B, as no amplification oligomers were added until the commencement of the exponential amplification phase. The A376 and A35 initial amplification oligomers (SEQ ID NO: 16 and 31) were present at the capture stage in the experiments whose whose results appear in FIGS. 4C-D.

At 2000 IU/ml, HBV nucleic acid was detected with reproducible emergence times in each experiment (indicated with arrows in FIGS. 4A-D). At the lower concentrations of HBV nucleic acid of 2 IU/ml and 10 IU/ml (indicated with brackets in FIGS. 4A-D; 2 IU/ml traces in gray and 10 IU/ml traces in black), the emergence times without T7 initial amplification oligomers (FIGS. 4A-B) were spread over a range of times higher than about 27 minutes for each of the amplicons detected by the 408-435 probe oligomer and the 668A probe oligomer. With the T7 initial amplification oligomers, the emergence times were generally at about 16-22 minutes for the amplicon detected by the 408-435 probe oligomer and at about 18-26 minutes for the amplicon detected by the 668A probe oligomer, although in isolated instances 2 IU/ml samples showed later emergence times. The 2 IU/ml and 10 IU/ml emergence time data were improved when the initial amplification oligomers were used in that the traces for these experiments showed earlier, more consistent emergence times that had less overlap than in the absence of the initial amplification oligomers (FIG. 4C vs. FIG. 4A; and FIG. 4D vs. FIG. 4B), consistent with the initial amplification oligomers facilitating a lower limit of quantification.

Example 3—NT7 Amplification Oligomer (−)02

Amplifications were performed on a range of HBV clone sequences corresponding to sequences from the HBV database using a set of oligomers at a concentration of 2000 IU/ml (3.3 log IU/ml), in which the NT7 (−)02 oligomer (SEQ ID NO: 3) was lacking and procedures were otherwise as in Example 2 with the two initial amplification oligomers being present. Most sequences were quantified to within about 0.25 logs of the target value, but clone 4G (in which there is a A to G mutation at the NT7 binding site of the corresponding region) was under-quantified by about 2 logs (not shown). Reactions with the (−)02 oligomer included at 0.2, 0.3, and 0.4 pmol/µl showed quantification in line with other clones and within about 0.25 logs of target, and the effect of adding the (−)02 oligomer on quantification of other clones was minimal.

Example 4—Displacer Oligomers

HBV DNA is partially double-stranded. Displacer oligos such as the 259-290 oligomer (SEQ ID NO: 67) or the 452B oligomer (SEQ ID NO: 73) can improve assay performance by generating single stranded template through extension of the displacer oligo and concomitant strand displacement.

The effect of using displacer oligos is shown below, in Table 1. Procedures were as in Example 2 with the two initial amplification oligomers present except that the displacer oligomers used were as indicated in Table 1.

TABLE 1

Sensitivity of detection of HBV with different displacer oligomers.

| Probe | N | Both Displacers Present | 259-290 only | 452B only | No Displacers Present |
|---|---|---|---|---|---|
| 408-435 (SEQ ID NO: 29) | 27 | 89% | 63% | 33% | 33% |
| 668A (SEQ ID NO: 40) | 27 | 89% | 74% | 74% | 82% |

Example 5—Exemplary Internal Control Oligomers

Oligomers according to SEQ ID NO: 77 (NT7 amplification oligomer), 78 (T7 amplification oligomer), 79 (probe), and 80 (capture) were evaluated for use as an internal control (a.k.a. general internal control [GIC], IC). Including the appropriate IC oligomers in the target capture and amplification reagents along with IC template in the target capture reagent did not significantly affect assay performance (not shown). Modest slowing based on resource competition (e.g., about 1 to 3 minute difference in emergence time at lower target concentrations) is not considered a significant effect.

Example 6—HBV Subtype Detection and Clinical Comparison

Figure 5:
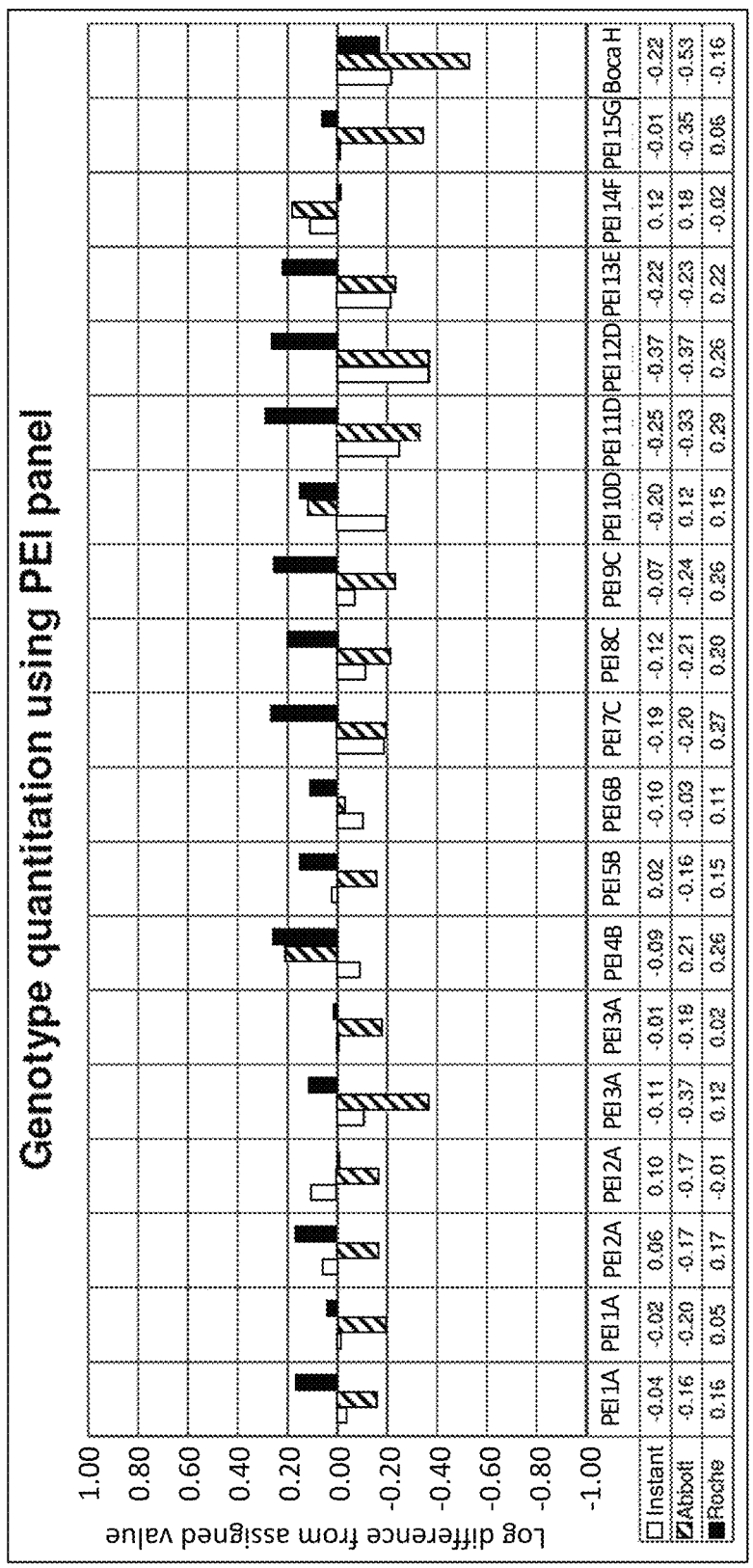
FIG. 5 shows log difference of observed relative to expected quantification for an exemplary quantification method (white bars) compared to commercially available assays from Abbott (striped bars) and Roche (black bars) performed on the PEI Genotype Panel.

Paul-Ehrlich-Institut (PEI) HBV genotype reference panels and an additional genotype H clinical sample (Boca Biolistics) were tested in replicates of 5. Procedures were as in Example 2 with the two initial amplification oligomers being present. FIG. 5 shows the quantitation results compared to results obtained from commercially available Abbott and Roche assays (single replicates). The PEI panel samples were generally quantified within 0.3 log copies of the target, comparing favorably to the individual measurements from the Abbott and Roche assays.

Example 7—Reproducibility, Linearity, and Data Analysis

Reproducibility.

A set of 796 individual donor samples with representation of Genotypes A-H and a range of viral loads was tested for reproducibility. The assay was as described in Example 2 including the two initial amplification oligomers. Quantification was reproducible over a wide range of concentrations of HBV nucleic acid as demonstrated in FIG. 6A.

Linearity.

Figure 6A:
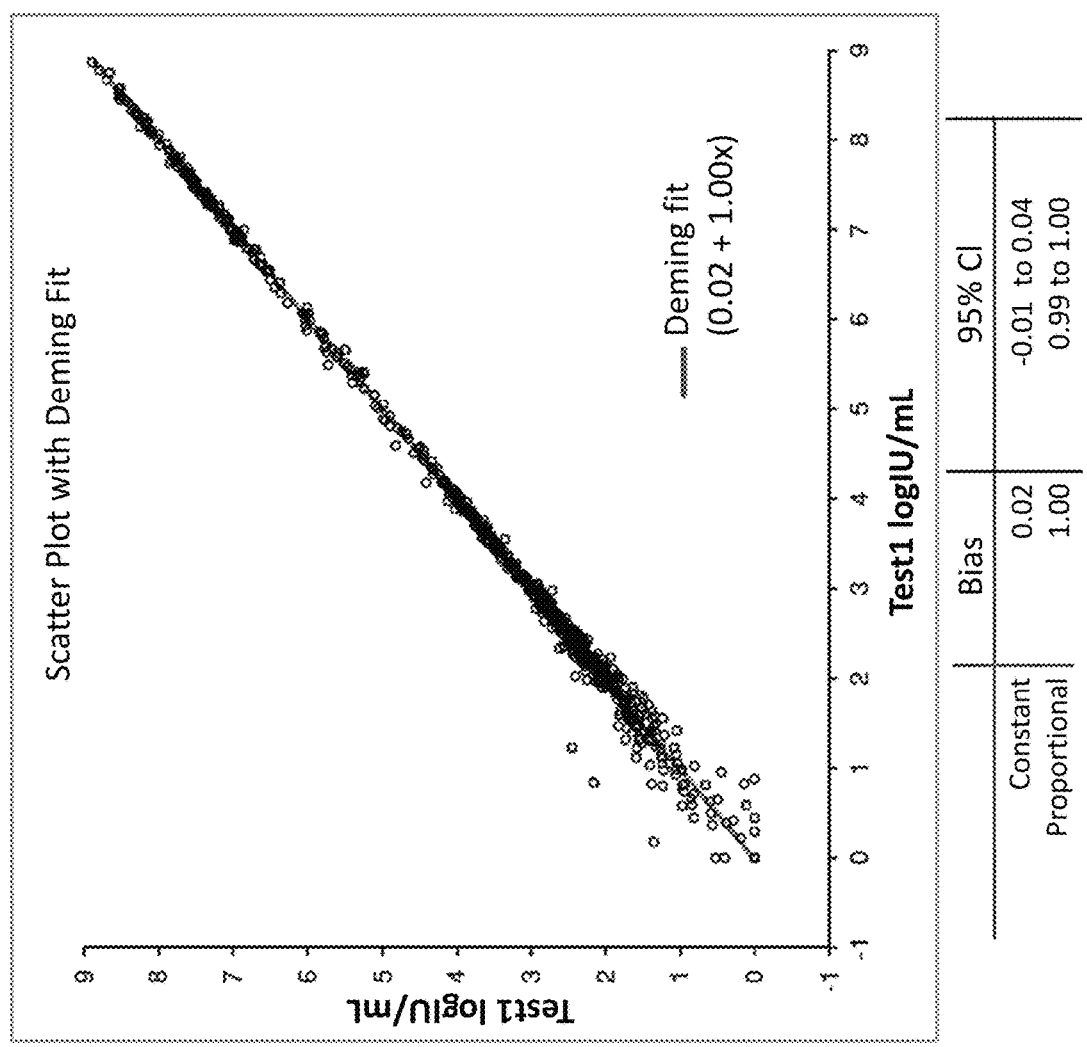
FIG. 6A shows a scatter plot demonstrating reproducibility of HBV quantification.
Figure 6B:
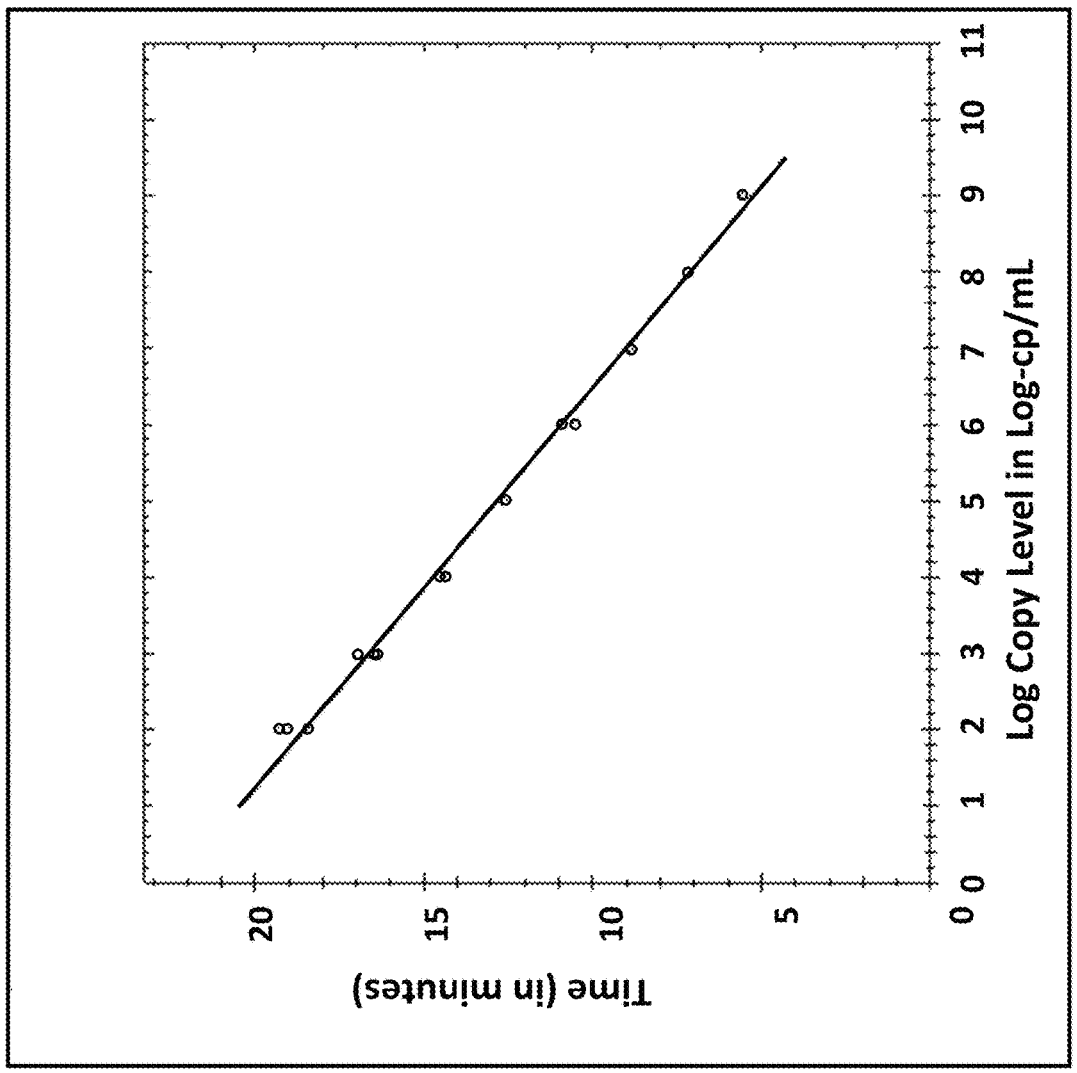
FIGS. 6B-C show calibration curves for converting emergence time to log copies/ml for amplicons 1 and 2, respectively.
Figure 6C:
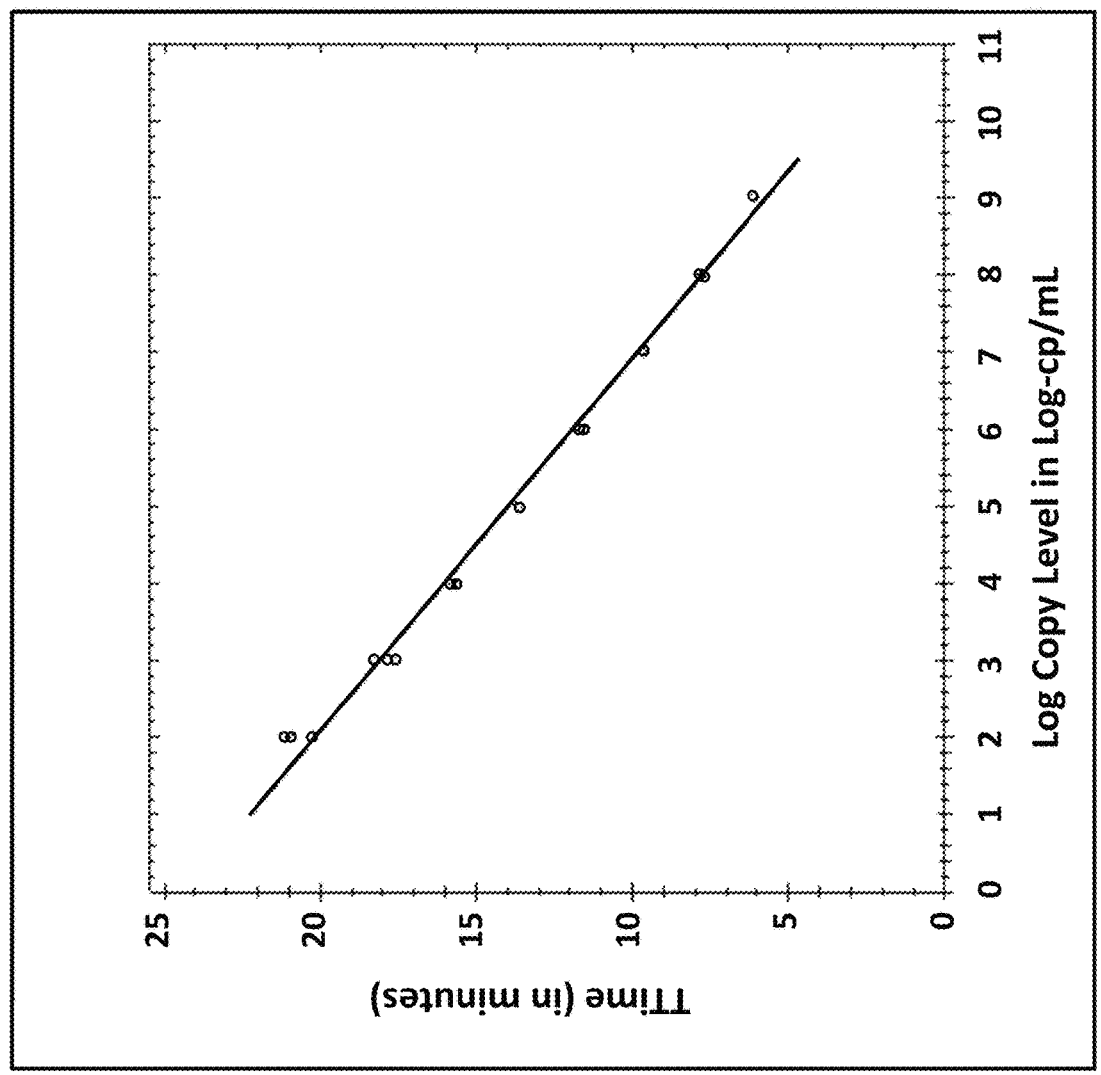

Quantification was also linear with emergence time for detection of both amplicons over a range encompassing from 2 to 9 log copies/ml of double-stranded HBV DNA (FIG. 6B, amplicon detected by 408-435 probe oligomer, FIG. 6C, amplicon detected by 668A probe oligomer).

Data Analysis.

It was observed that precision was lower at the low end of concentrations, e.g., below about 50 IU/ml (about 1.7 log IU/ml) (FIG. 6A). It was also found that divergent measurements of amplicon 1 and amplicon 2 (e.g., where amplicon 1 indicated a concentration below about 50 IU/ml and amplicon 2 indicated a concentration above about 50 IU/ml, or vice versa) sometimes resulted from the presence of a mutation in the HBV sequence that delayed amplification and suppressed the observed concentration accordingly (data not shown).

In light of this phenomenon and the comparatively higher accuracy and precision of single amplicon quantification above about 50 IU/ml, a piecewise analytical process was developed in which the assay result was reported as the maximum of the amplicon 1 and 2 observations if either or both were greater than or equal to 50 IU/ml, and otherwise the arithmetic mean of the amplicon 1 and 2 observations was reported. This piecewise process was found to improve overall accuracy (e.g., expressed as the frequency of errors exceeding a threshold such as 0.25 log copies/ml relative to target over a panel of different genotypes and concentrations) relative to each of (i) always reporting the mean and (ii) always reporting the maximum. It is understood that the transition being at 50 IU/ml is not critical to obtain a benefit with respect to overall accuracy; for example, transition values such as about 25 IU/ml or 100 IU/ml are also expected to be effective.

Example 8—Effect of Quantifying for Amplicons 1+2 on Accuracy and Reactivity in Low Concentration Assays The effect of including reagents for amplification and detection of amplicon 2 in addition to amplicon 1 was evaluated. Procedures were as in Example 2 with the two initial amplification oligomers being present, except that for the Amplicon 1 only data, the A35, A02, A08, and 668A oligomers were not present. Accuracy was evaluated at 10 IU/ml. Sensitivity was evaluated at 5 IU/ml.

Quantification of the Amplicon 1+2 results was as described in Example 7, using a 50 IU/ml transition value for the piecewise analytical process. Relative to amplicon 1 only, including amplification and analysis of amplicon 2 reduced total error for Genotypes B-F (Table 2). Reactivity improved or stayed about the same for all genotypes, including genotypes B, D, and E in which reactivity improved to 100% (Table 3).

TABLE 2

Accuracy of Amplicon 1 vs. Amplicon 1 + 2 Quantification

| Genotype (10 IU/ml) | Amplicon 1 | | Amplicon 1 + 2 | |
|---|---|---|---|---|
| | N | Total Error (log IU/ml) | N | Total Error (log IU/ml) |
| A | 54 | 1.08 | 10 | 1.11 |
| B | 53 | 1.03 | 10 | 0.81 |
| C | 54 | 1.13 | 10 | 0.75 |
| D | 53 | 1.06 | 10 | 0.81 |
| E | 54 | 1.34 | 10 | 0.97 |
| F | 54 | 0.9 | 10 | 0.45 |

Total error = bias + 2 × (Standard Deviation)

TABLE 3

Reactivity of Amplicon 1 vs. Amplicon 1 + 2 Detection

| Genotype (5 IU/ml) | Amplicon 1 | | Amplicon 1 + 2 | |
|---|---|---|---|---|
| | N | % Reactive | N | % Reactive |
| A | 54 | 98.1 | 10 | 100 |
| B | 54 | 92.6 | 10 | 100 |
| C | 54 | 87 | 10 | 90 |
| D | 54 | 87 | 10 | 100 |
| E | 54 | 96.3 | 10 | 100 |
| F | 54 | 100 | 10 | 100 |

Example 9—Additional Characterization of Assay Performance

The assay as described in Example 2 including the two initial amplification oligomers was further characterized as follows.

Quantification Across Genotypes.

Genotypes B-H and C2 were all quantified within about 0.15 logs of genotype A by the amplicons individually or in combination as shown in Table 4. Each of genotypes B, C, C2, and E-H were quantified within 0.1 logs of genotype A when data from both amplicons were used, demonstrating improved consistency of quantification.

TABLE 4

Quantification Across Genotypes.

| Sample | Target Log Copies/mL | Positivity (%) | Amplicons 1 + 2 Log Copies/mL | Amplicon 1 Log Copies/mL | Amplicon 2 Log Copies/mL | Amplicons 1 + 2 Diff. from Genotype A | Amplicon 1 Diff. from Genotype A | Amplicon 2 Diff. from Genotype A |
|---|---|---|---|---|---|---|---|---|
| Genotype A | 4 | 100.00% | 3.97 | 3.99 | 3.95 | 0 | 0 | 0 |
| Genotype B | 4 | 100.00% | 3.93 | 3.87 | 3.97 | 0.04 | 0.12 | −0.02 |
| Genotype C | 4 | 100.00% | 3.88 | 3.87 | 3.9 | 0.09 | 0.12 | 0.05 |
| Genotype C2 | 4 | 100.00% | 3.91 | 3.92 | 3.91 | 0.06 | 0.07 | 0.04 |
| Genotype D | 4 | 100.00% | 3.82 | 3.84 | 3.81 | 0.15 | 0.15 | 0.14 |
| Genotype E | 4 | 100.00% | 3.9 | 3.9 | 3.9 | 0.07 | 0.09 | 0.05 |

TABLE 4-continued

Quantification Across Genotypes.

| Sample | Target Log Copies/mL | Positivity (%) | Amplicons 1 + 2 Log Copies/mL | Amplicon 1 Log Copies/mL | Amplicon 2 Log Copies/mL | Amplicons 1 + 2 Diff. from Genotype A | Amplicon 1 Diff. from Genotype A | Amplicon 2 Diff. from Genotype A |
|---|---|---|---|---|---|---|---|---|
| Genotype F | 4 | 100.00% | 3.95 | 3.84 | 4.04 | 0.02 | 0.15 | −0.09 |
| Genotype G | 4 | 100.00% | 3.91 | 3.85 | 3.97 | 0.06 | 0.14 | −0.02 |
| Genotype H | 4 | 100.00% | 3.96 | 3.88 | 4.03 | 0.01 | 0.11 | −0.08 |

Clinical Specificity.

Clinical specificity was assessed by testing 292 fresh and 747 frozen HBV negative clinical specimens. A total of 521 plasma and 581 serum specimens were tested. Specificity was calculated as the percentage of HBV negative samples for which HBV DNA was not detected. HBV DNA was not detected in 1038/1039 total samples (99.9% specificity, 95% confidence interval: 99.5-100%). The single false positive occurred with a frozen serum sample (Table 5).

TABLE 5

Clinical Specificity results.

| | Valid Replicates (n) | Not Detected | Specificity |
|---|---|---|---|
| Fresh Plasma | 145 | 145 | 100% |
| Frozen Plasma | 376 | 376 | 100% |

TABLE 5-continued

Clinical Specificity results.

| | Valid Replicates (n) | Not Detected | Specificity |
|---|---|---|---|
| Fresh Serum | 147 | 147 | 100% |
| Frozen Serum | 371 | 370 | 99.7% |
| Total | 1039 | 1038 | 99.9% (95% CI: 99.5-100%) |

Cross-Reactivity.

To assess whether the assay would cross react with microorganisms or viruses that could be present in clinical samples, resulting in false positive results or bias to quantification accuracy, 5 microorganisms and 15 blood borne viruses (BBV) were spiked into HBV negative normal donors (Table 6). None of the microorganisms contributed to false positive results in the absence of HBV virus. In the presence of HBV Virus at 2000 IU/mL (i.e., 10000 copies/ml or 4 log copies/ml), none of the microorganisms interfered with detection. The HBV-positive samples with an additional microorganism or blood borne virus all showed 100% reactivity and were quantified within an average of 0.21 log copies. The maximum difference observed was 0.38 log copies for HIV-2 in detection of amplicon 2 and HTLV in detection of both amplicons.

TABLE 6

Analysis of Cross-Reactivity.

| Condition | Microorganism | N | # of Positive | % Reactive |
|---|---|---|---|---|
| Microorganism Specificity | Neg Control | 5 | 0 | 0.0% |
| | Neisseria gonorrboeae | 5 | 0 | 0.0% |
| | Propionibacterium acnes | 5 | 0 | 0.0% |
| | Candida albicans | 5 | 0 | 0.0% |
| | Staphylococcus epidermis | 5 | 0 | 0.0% |
| | Staphylococcus aureus | 5 | 0 | 0.0% |

| Condition | Microorganism/BBV | N | # of Positive | % Reactive | Amplicon 1 Mean LogCopy | Amplicon 2 Mean LogCopy | Amplicon 1 + 2 Mean LogCopy |
|---|---|---|---|---|---|---|---|
| Microorganism Analytical Sensitivity | HBV Pos Control | 5 | 5 | 100.0% | 4.15 | 4.06 | 4.10 |
| | Neisseria gonorrboeae | 5 | 5 | 100.0% | 4.12 | 3.99 | 4.06 |
| | Propionibacterium acnes | 5 | 5 | 100.0% | 4.13 | 4.08 | 4.11 |
| | Candida albicans | 5 | 5 | 100.0% | 4.14 | 4.04 | 4.09 |
| | Staphylococcus epidermis | 5 | 5 | 100.0% | 4.12 | 3.97 | 4.05 |
| | Staphylococcus aureus | 5 | 5 | 100.0% | 4.13 | 4.02 | 4.07 |
| Bloodborne Virus Analytical Sensitivity | HBV Pos Control | 5 | 5 | 100.0% | 4.14 | 4.04 | 4.09 |
| | Rubella | 5 | 5 | 100.0% | 3.89 | 3.72 | 3.81 |
| | HSV1 | 5 | 5 | 100.0% | 3.94 | 3.80 | 3.87 |
| | HSV2 | 5 | 5 | 100.0% | 3.98 | 3.79 | 3.89 |
| | Flu Vaccinated | 5 | 5 | 100.0% | 4.02 | 3.82 | 3.93 |
| | EBV | 5 | 5 | 100.0% | 3.90 | 3.73 | 3.82 |
| | HIV2 | 5 | 5 | 100.0% | 3.86 | 3.66 | 3.77 |

TABLE 6-continued

Analysis of Cross-Reactivity.

| | | | | | | |
|---|---|---|---|---|---|---|
| Parvo | 5 | 5 | 100.0% | 4.00 | 3.84 | 3.93 |
| CMV | 5 | 5 | 100.0% | 3.97 | 3.83 | 3.90 |
| HBV Vaccinated | 5 | 5 | 100.0% | 3.95 | 3.87 | 3.91 |
| HAV | 5 | 5 | 100.0% | 3.95 | 3.85 | 3.90 |
| HTLV | 4 | 4 | 100.0% | 3.76 | 3.66 | 3.71 |
| WNV (3,000 c/mL) | 5 | 5 | 100.0% | 4.00 | 3.97 | 3.98 |
| HCV (3,000 c/mL) | 5 | 5 | 100.0% | 4.05 | 3.98 | 4.02 |
| Dengue (3,000 c/mL) | 5 | 5 | 100.0% | 4.12 | 4.06 | 4.09 |

Abbreviations: HSV, herpes simplex virus; EBV, Epstein Barr virus; HIV, human immunodeficiency virus; CMV, cytomegalovirus; HAV, hepatitis A virus; HTLV, human T-lymphotropic virus; WNV, West Nile virus.

TABLE OF SEQUENCES
In the following table, lower case letters indicate 2'Ome RNA and upper case letter indicate DNA.

| SEQ ID NO | Description | Sequence | |
|---|---|---|---|
| 1 | Representative HBV A1 sequence, GenBank Acc. No. AB116092 | 1 | TTCCACAGCT TTCCACCAAG CTCTGCAAGA TCCCAGAGTC AGGGGCCTGT ATTTTCCTGC |
| | | 61 | TGGTGGCTCC AGTTCAGGAA CACTCAACCC TGTTCCAACT ATTGCCTCTC ACATCTCGTC |
| | | 121 | AATCTCCTCG AGGATTGGGG ACCCTGCACC GAACATGGAG AACATCACAT CAGGATTCCT |
| | | 181 | AGGACCCCTG CTCGTGTTAC AGGCGGGGTT TTTCTTGTTG ACAAGAATCC TCACAATACC |
| | | 241 | GCAGAGTCTA GACTCGTGGT GGACTTCTCT CAATTTTCTA GGGGGAGCAC CCGTGTGTCT |
| | | 301 | TGGCCAAAAT TCGCAGTCCC CAACCTCCAA TCACTCACCA ACCTCCTGTC CTCCAATTTG |
| | | 361 | TCCTGGTTAT CGCTGGATGT GTCTGCGGCG TTTTATCATA TTCCTCTTCA TCCTGCTGCT |
| | | 421 | ATGCCTCATC TTCTTATTGG TTCTTCTGGA TTATCAAGGT ATGTTGCCCG TTTGTCCTCT |
| | | 481 | AATTCCAGGA TCAACAACAA CCAGCACGGG ACCCTGCAAA ACCTGCACGA CTCCTGCTCA |
| | | 541 | AGGGAACTCT ATGTTTCCCT CATGTTGCTG TACAAAACCT ACGGATGGAA ATTGCACCTG |
| | | 601 | TATTCCCATC CATCATCTT GGGGTTTCGC AAAATTCCTA TGGGAGTGGG CCTCAGTCCG |
| | | 661 | TTTCTCTTGT CTCAGTTTAC TAGTGCCATT TGTTCAGTGG TTCGTAGGGC TTTCCCCCAC |
| | | 721 | TGTTTGGCTT TTAGCTATAT GGATGATGTG GTACTGGGGG CCAAGTCTGT ACAACATCTT |
| | | 781 | GAGTCCCTTT ACACCGCTGT TACCAATTTT CTTTTGTCTT TGGGTATACA TTTAAACCCT |
| | | 841 | AACAAAACAA AGAGATGGGG TTATTCCCTG AATTTCATGG GTTATGTAAT TGGAAGTTGG |
| | | 901 | GGTACATTGC CACAGGATCA TATTGTACAA AAAATCAAAC ACTGTTTTAG AAAACTTCCT |
| | | 961 | GTAAATCGAC CTATTGATTG GAAAGTATGT CAGAGAATTG TGGGTCTTTT GGGCTTTGCA |
| | | 1021 | GCTCCATTTA CACAATGTGG TTACCCTGCA TTAATGCCTT TGTATGCATG TATACAGGCG |
| | | 1081 | AAACAGGCTT TTACTTTCTC GCCAACTTAC AAGGCCTTTC TAAGTAAACA GTATATGAAC |
| | | 1141 | CTTTACCCCG TTGCCCGGCA ACGGCCTGGT CTGTGCCAAG TGTTTGCTGA CGCAACCCCC |
| | | 1201 | ACTGGCTGGG GCTTGGCCAT CGGCCATCAG CGCATGCGTG GAACCTTTGT GGCTCCTCTG |
| | | 1261 | CCGATCCATA CTGCGGAACT CCTAGCCGCT TGTTTTGCTC GCAGCAGGTC TGGAGCAAAA |
| | | 1321 | CTCATCGGAA CTGATAATTC TGTCGTCCTT TCTCGGAAGT ATACATCCTT TCCATGGCTG |
| | | 1381 | CTAGGTTGTA CTGCCAACTG GATTCTTCGC GGGACGTCCT TTGTCTACGT CCCGTCGGCG |
| | | 1441 | CTGAATCCCG CGGACGACCC TTCGCGAGGC CGCTTGGGGC TGTATCGTCC CCTTCTCCGT |
| | | 1501 | CTGCCGTACC GTCCGACCAC GGGGCGCACC TCTCTTTACG CGGTCTCCCC GTCTGTGCCT |
| | | 1561 | TCTCATCTGC CGGTCCGTGT GCACTTCGCT TCACCTCTGC ACGTTGCATG GAGACCACCG |
| | | 1621 | TGAACGCCCA TCAGGTCCTG CCCAAGGTCT TATATAAGAG GACTCTTGGA CTCTCAGCAA |
| | | 1681 | TGTCAACGAC CGACCTTGAG GCCTACTTCA AAGACTGTGT GTTTAAAGAC TGGGAGGAGT |
| | | 1741 | TGGGGGAGGA GATTAGGTTA ATGATCTTTG TATTAGGAGG CTGTAGGCAT AAATTGGTCT |
| | | 1801 | GCGCACCATC ATCATGCAAC TTTTTCACCT CTGCCTAATC ATCTCTTGTA CATGTCCCAC |
| | | 1861 | TTTTCAAGCC TCCAAGCTGT GCCTTGGATG GCTTTGGGGC ATGGACATTG ACCCTTATAA |
| | | 1921 | AGAATTTGGA GCTACTGTGG AGTTACTTTC ATTTTTGCCT TCTGACTTCT TTCCTTCCGT |
| | | 1981 | CCGGGATCTA CTAGATACAG TCGCAGCTCT ATTTCGGGAT GCCTTAGAGT CTCCTGAGCA |
| | | 2041 | TTGCTCAGCT CACCACACAG CACTAAGGCA AGTCATTCTC TGCTGGGGGG AATTAATGAC |
| | | 2101 | TCTAGCTACC TGGGTGGGTA CTAATTTGCA AGATCCAGCA TCCAGGGATC TAGTAGTCAG |
| | | 2161 | TTATGTTAAT GATAACATGG GCCTAAAGAT CAGGCAATTA TTATGTTTC ATACTTCTTG |
| | | 2221 | CATTACTTTT GGAAGAGAAA CTGTCCTTGA GTATTTGGTC TCTTTCGGAG TGTGGATTCG |
| | | 2281 | CACTCCTCCA GCCTATAGAC CACCAAATGC CCCTATCTTA TCAACACTTC CGGAAACTAC |
| | | 2341 | TGTTGTTAGA CGACGAGACC GAGGCAGGTC CCCTAGAAGA AGAACTCCCT CGCCTCGCAG |
| | | 2401 | ACGAAGATCT CAATCGCCGC GTCGCAGAAG ATCTCAATCT CGGGAACCTC AATGTTAGTA |
| | | 2461 | TTCCTTGGAC TCATAAGGTG GGAAATTTTA CTGGACTTTA TTCTTCTACT GTCCCTATCT |
| | | 2521 | TTAATCCTGA ATGGCAAACA CCGTCTTTTC CTAAAATTCA TTTACATGAA GACATTGCTA |
| | | 2581 | ATAGGTGTCA GCAATTTGTA GGCCCTCTCA CTGTAAATGA AAAAGAAGA CTGAAATTAA |
| | | 2641 | TTATGCCTGC TAGGTTTTAT CCTAACAGCA CAAAATATTT GCCTTTAGAC AAAGGGATTA |
| | | 2701 | AAACTTATTA TCCTGATCAG GTAGTTAATC ATTACTTTCA AACCCGACAT TATTTACATA |
| | | 2761 | CTCTTTGGAA GGCTGGGATT CTATATAAGA GGGAAACTAC ACGTAGCGCC TCATATTGCG |
| | | 2821 | GGTCACCATA TTCTTGGGAA CAAGAGCTAC ATCATGGGAG GTTGGTCATC AAAACCTCGC |
| | | 2881 | AAAGGCATGG GGACGAACCT TTCTGTTCCC AACCCGCTGG GATTCTTTCC CGATCATCAG |
| | | 2941 | TTGGACCCTG CATTCGGAGC CAATGCAAAC AATCCAGATT GGGACCTCAA CCCCATCAAG |
| | | 3001 | GACCACTGGC CACAAGCCAA CCAGGTAGGA GTGGGAGCAT TTGGACCAGG CTCACTCCC |
| | | 3061 | CCACACGGAG GTGTTTTGGG GTGGAGCCCT CAGGCTCAAG GCATATTGGC CACCGTGCCA |
| | | 3121 | ACAGTGCCTC CTCCTGCCTC CACCAATCGG CAGTCGGAA GGCAGCCTAC TCCCATTTCT |
| | | 3181 | CCACCTCTAA GAGACAGTCA TCCTCAGGCC ATGCAGTGGA A |

-continued

TABLE OF SEQUENCES
In the following table, lower case letters indicate 2'Ome RNA and upper case letter indicate DNA.

| SEQ ID NO | Description | Sequence |
|---|---|---|
| 2 | NT7 amplification oligomer 474-455 | GGCACCTAGTCCAGAAGAACCAA |
| 3 | NT7 amplification oligomer (-)02 | GGCACCTAGTCCAGAAGAACC |
| 4 | amplification oligomer subsequence | CAGAAGAACC |
| 5 | amplification oligomer subsequence | TAGTCCAGAA |
| 6 | amplification oligomer subsequence | GCACCTAGTC |
| 7 | amplification oligomer subsequence | GAAGAACCAA |
| 8 | Exemplary T7 promoter | TAATACGACTCACTATAG |
| 9 | Sequence comprising T7 promoter | TAATACGACTCACTATAGGGAGA |
| 10 | Sequence comprising T7 promoter | TAATACGACTCACTATAGGGAGACCACAACG |
| 11 | Sequence comprising T7 promoter | AATTTAATACGACTCACTATAG |
| 12 | Sequence comprising T7 promoter | AATTTAATACGACTCACTATAGGGAGA |
| 13 | Sequence comprising T7 promoter | AATTTAATACGACTCACTATAGGGAGACCACAACG |
| 14 | T7 amplification oligomer 376-397 | AATTTAATACGACTCACTATAGGGAGAGATGTGTCTGCGGCGTTTTATC |
| 15 | T7 amplification oligomer 376-402 | AATTTAATACGACTCACTATAGGGAGAGATGTGTCTGCGGCGTTTTATCATCTT |
| 16 | T7 amplification oligomer A376 | AATTTAATACGACTCACTATAGGGAGAGATGTGTCTGCGGCGTTTTATCATCTTCCT |
| 17 | amplification oligomer A376 subsequence | GGAGAGATGTGTCTGCGGCGTTTTATCATCTTCCT |
| 18 | amplification oligomer 376-397 subsequence | GGAGAGATGTGTCTGCGGCGTTTTATC |
| 19 | amplification oligomer 376-402 subsequence | GGAGAGATGTGTCTGCGGCGTTTTATCATCTT |
| 20 | amplification oligomer A376 subsequence | GATGTGTCTGCGGCGTTTTATCATCTTCCT |
| 21 | amplification oligomer 376-397 subsequence | GATGTGTCTGCGGCGTTTTATC |
| 22 | amplification oligomer 376-402 subsequence | GATGTGTCTGCGGCGTTTTATCATCTT |

TABLE OF SEQUENCES
In the following table, lower case letters indicate 2'Ome RNA and upper case letter indicate DNA.

| SEQ ID NO | Description | Sequence |
|---|---|---|
| 23 | amplification oligomer subsequence | GCGTTTTATC |
| 24 | amplification oligomer subsequence | CTGCGGCGTT |
| 25 | amplification oligomer subsequence | TGTGTCTGCG |
| 26 | amplification oligomer subsequence | TTATCATCTT |
| 27 | amplification oligomer subsequence | TCATCTTCCT |
| 28 | amplification oligomer subsequence | GGAGAGATGT |
| 29 | probe oligomer 408-435 | cccacaagaagaugaggcauagcagcaggauga(C9)guggg |
| 30 | amplification oligomer A02 | AATTTAATACGACTCACTATAGGGAGACCACAACGGTGGGCCTCAGTCCGTTTCTC |
| 31 | amplification oligomer A35 | AATTTAATACGACTCACTATAGGGAGACCACAACGGTGGGCCTCAGTCCGTTTCTCITGGCT |
| 32 | amplification oligomerA02 subsequence | GGAGACCACAACGGTGGGCCTCAGTCCGTTTCTC |
| 33 | amplification oligomerA35 subsequence | GGAGACCACAACGGTGGGCCTCAGTCCGTTTCTCITGGCT |
| 34 | amplification oligomer A02 subsequence | CCACAACGGTGGGCCTCAGTCCGTTTCTC |
| 35 | amplification oligomer A35 subsequence | CCACAACGGTGGGCCTCAGTCCGTTTCTCITGGCT |
| 36 | amplification oligomer subsequence | TCCGTTTCTC |
| 37 | amplification oligomer subsequence | CTCAGTCCGT |
| 38 | amplification oligomer subsequence | TGGGCCTCAG |
| 39 | amplification oligomer subsequence | TCTCITGGCT |
| 40 | probe oligomer 668A | ugcgcuaguaaacugagccag(C9)gcgca |
| 41 | NT7 amplification oligomer A08 | CCTGCGAACCACTGAACAAA |
| 42 | amplification oligomer subsequence | CACTGAACAAA |
| 43 | amplification oligomer subsequence | GAACCACTGA |
| 44 | amplification oligomer subsequence | CCTGCGAACC |

TABLE OF SEQUENCES
In the following table, lower case letters indicate 2'Ome RNA and upper case letter indicate DNA.

| SEQ ID NO | Description | Sequence |
|---|---|---|
| 45 | Capture oligomer 0707b | GGGCTTTCCCCCACTGTTTGGCTTTTTAAAAAAAAAAAAAAAAAAAAAAAAAAAAAA |
| 46 | Capture oligomer 733 | AGTTATATGGATGATGTGGTATTGGTTTAAAAAAAAAAAAAAAAAAAAAAAAAAAAAA |
| 47 | Capture oligomer 1168 | GGTCTGTGCCAAGTGTTTGCTGACGCTTTAAAAAAAAAAAAAAAAAAAAAAAAAAAAAA |
| 48 | Capture oligomer 1290 | TTGTTTTGCTCGCAGCCGGTCTGGAGCGAAAAAAAAAAAAAAAAAAAAAAAAAAAAAA |
| 49 | Capture oligomer 0707b target hybridizing sequence | GGGCTTTCCCCCACTGTTTGGC |
| 50 | Capture oligomer subsequence | ACTGTTTGGC |
| 51 | Capture oligomer subsequence | CCCCCACTGT |
| 52 | Capture oligomer subsequence | GGGCTTTCCC |
| 53 | Capture oligomer 733 target hybridizing sequence | AGTTATATGGATGATGTGGTATTGG |
| 54 | Capture oligomer subsequence | GTGGTATTGG |
| 55 | Capture oligomer subsequence | ATGATGTGGT |
| 56 | Capture oligomer subsequence | TATGGATGAT |
| 57 | Capture oligomer 1168 target hybridizing sequence | GGTCTGTGCCAAGTGTTTGCTGACGC |
| 58 | Capture oligomer subsequence | TTGCTGACGC |
| 59 | Capture oligomer subsequence | AGTGTTTGCT |
| 60 | Capture oligomer subsequence | TGCCAAGTGT |
| 61 | Capture oligomer 1290 target hybridizing sequence | TTGTTTTGCTCGCAGCCGGTCTGGAGCG |
| 62 | Capture oligomer subsequence | GTCTGGAGCG |
| 63 | Capture oligomer subsequence | AGCCGGTCTG |
| 64 | Capture oligomer subsequence | CTCGCAGCCG |
| 65 | $T_3A_{30}$ | TTTAAAAAAAAAAAAAAAAAAAAAAAAAAAAAA |
| 66 | $A_{30}$ | AAAAAAAAAAAAAAAAAAAAAAAAAAAAAA |
| 67 | Amplification oligomer 259-290 (T7 displacer) | AATTTAATACGACTCACTATAGGGAGAAGACTCGTGGTGGACTTCTCTCAATTTTCT |

TABLE OF SEQUENCES
In the following table, lower case letters indicate 2'Ome RNA and upper case letter indicate DNA.

| SEQ ID NO | Description | Sequence |
|---|---|---|
| 68 | Amplification oligomer 259-290 subsequence | GGAGAAGACTCGTGGTGGACTTCTCTCAATTTTCT |
| 69 | Amplification oligomer 259-290 subsequence | AGACTCGTGGTGGACTTCTCTCAATTTTCT |
| 70 | Amplification oligomer 259-290 subsequence | TCAATTTTCT |
| 71 | Amplification oligomer 259-290 subsequence | TTCTCTCAAT |
| 72 | Amplification oligomer 259-290 subsequence | TGGACTTCTC |
| 73 | Amplification oligomer 452B (NT7 displacer) | TATCAAGGTATGTTGCCCGT |
| 74 | Amplification oligomer 452B subsequence | TGTTGCCCGT |
| 75 | Amplification oligomer 452B subsequence | AGGTATGTTG |
| 76 | Amplification oligomer 452B subsequence | TATCAAGGTA |
| 77 | Control NT7 amplification oligomer 4102 | GATTATATAGGACGACAAG |
| 78 | Control T7 amplification oligomer 4203 | AATTTAATACGACTCACTATAGGGAGAGATGATTGACTTGTGATTCCGC |
| 79 | Control Probe oligomer 4180-4197 C9(5-6) | gcaug(c9)gugcgaauugggacaugc |
| 80 | Control capture oligomer 4277 | ucguucacuauuggucucugcauucTTTAAAAAAAAAAAAAAAAAAAAAAAAAAAA |
| 81 | Control capture oligomer target hybridizing sequence | cguucacuauuggucucugcauuc |
| 82 | Probe oligomer 408-435 subsequence | aagaagaugaggcauagcagcaggauga |
| 83 | Probe oligomer 668A subsequence | gcuaguaaac |
| 84 | Probe oligomer 668A subsequence | uaguaaacugagccag |
| 85 | Probe oligomer 668A subsequence | gcuaguaaacugagccag(C9)gc |
| 86 | Control amplification oligomer 4203 subsequence | GATGATTGACTTGTGATTCCGC |

TABLE OF SEQUENCES

In the following table, lower case letters indicate 2'Ome RNA and upper case letter indicate DNA.

| SEQ ID NO | Description | Sequence |
|---|---|---|
| 87 | Capture oligomer 1168 | GGTCTGTGCCAAGTGTTTGCTGACGCTTTAAAAAAAAAAAAAAAAAAAAAAAAAAAAAA |
| 88 | Capture oligomer 1254 | TCCTCTGCCGATCCATACTGCGGAACTCCTAAAAAAAAAAAAAAAAAAAAAAAAAAAAAA |
| 89 | Capture oligomer 1290 | TTGTTTTGCTCGCAGCCGGTCTGGAGCGAAAAAAAAAAAAAAAAAAAAAAAAAAAAAA |
| 90 | Capture oligomer 707 | GGGCTTTCCCCCACTGTTTGGCTTTTAAAAAAAAAAAAAAAAAAAAAAAAAAAAAA |
| 91 | Capture oligomer 733 | AGTTATATGGATGATGTGGTATTGGTTTAAAAAAAAAAAAAAAAAAAAAAAAAAAAAA |
| 92 | Capture oligomer 794 | CCGCTGTTACCAATTTTCTTTTGTCTTTAAAAAAAAAAAAAAAAAAAAAAAAAAAAAA |
| 93 | Capture oligomer 1168MR | GGUCUGUGCCAAGUGUUUGCUGACGCUUUAAAAAAAAAAAAAAAAAAAAAAAAAAAAAA |
| 94 | Capture oligomer 1290MR | GUCUGUGCCAAGUGUUUGCUGACGCUUUAAAAAAAAAAAAAAAAAAAAAAAAAAAAAA |
| 95 | Capture oligomer 733MR | AGUUAUAUGGAUGAUGUGGUACUGGUUUAAAAAAAAAAAAAAAAAAAAAAAAAAAAAA |
| 96 | Capture oligomer 1168 target hybridizing sequence | GGTCTGTGCCAAGTGTTTGCTGACGC |
| 97 | Capture oligomer 1254 target hybridizing sequence | TCCTCTGCCGATCCATACTGCGGAACTCC |
| 98 | Capture oligomer 1290 target hybridizing sequence | TTGTTTTGCTCGCAGCCGGTCTGGAGCG |
| 99 | Capture oligomer 707 target hybridizing sequence | GGGCTTTCCCCCACTGTTTGGCTTTT |
| 100 | Capture oligomer 733 target hybridizing sequence | AGTTATATGGATGATGTGGTATTGG |
| 101 | Capture oligomer 794 target hybridizing sequence | CCGCTGTTACCAATTTTCTTTTGTC |
| 102 | Capture oligomer 1168MR target hybridizing sequence | GGUCUGUGCCAAGUGUUUGCUGACGC |
| 103 | Capture oligomer 1290MR target hybridizing sequence | GUCUGUGCCAAGUGUUUGCUGACGC |
| 104 | Capture oligomer 733MR target hybridizing sequence | AGUUAUAUGGAUGAUGUGGUAUUGG |
| 105 | Representative HBV A2 sequence, GenBank Acc. No. AY707087, positions 1-900 | 1 AATTCCACTG CCTTCCACCA AGCTCTGCAG GATCCCAAAG TCAGGGGTCT GTATTTTCCT<br>61 GCTGGTGGCT CCAGTTCAGG AACAGTAAAC CCTGCTCCGA ATATTGCCTC TCACATCTCG<br>121 TCAATCTCCG CGAGGACTGG GGACCCTGTG ACGAATATGG AGAACATCAC ATCAGGATTC<br>181 CTAGGACCCC TGCTCGTGTT ACAGGCGGGG TTTTTCTTGT TGACAAGAAT CCTCACAATA<br>241 CCGCAGAGTC TAGACTCGTG GTGGACTTCT CTCAATTTTC TAGGGGGATC ACCCGTGTGT<br>301 CTTGGCCAAA ATTCGCAGTC CCCAACCTCC AATCACTCAC CAACCTCCTG TCCTCCAATT<br>361 TGTCCTGGTT ATCGCTGGAT GTGTCTGCGG CGTTTTATCA TATTCCTCTT CATCCTGCTG<br>421 CTATGCCTCA TCTTCTTGTT GGTTCTTCTG GATTATCAAG GTATGTTGCC CGTTTGTCCT<br>481 CTAATTCCAG GAACAACAAC AACCAGTACG GGACCATGCA AAACCTGCAC GACTCCTGCT<br>541 CAAGGCAACT CTATGTTTCC CTCATGTTGC TGTACAAAAC CTTCGGATGG AAATTGCACC<br>601 TGTATTCCCA TCCCATCGTC TTGGGCTTTC GCAAAATACC TATGGGAGTG GGCCTCAGTC<br>661 CGTTTCTCTT GGCTCAGTTT ACTAGTGCCA TTTGTTCAGT GGTTCGTAGG CTTTCCCCC<br>721 ACTGTTTGGC TTTCAGCTAT ATGGATGATG TGGTATTGGG GGCCAAGTCT GTACAGCATC<br>781 GTGAGTCCCT TTATACCGCT GTTACCAATT TTCTTTTGTC TCTGGGTATA CATTTAAACC |

TABLE OF SEQUENCES
In the following table, lower case letters indicate 2'Ome RNA and upper case letter indicate DNA.

| SEQ ID NO | Description | Sequence |
|---|---|---|
| | | 841 CTAACAAAAC AAAAAGATGG GGTTATTCCC TAAACTTCAT GGGTTACATA ATTGGAAGTT |
| | | 901 GGGGAACGTT GCCACAGGAT CATATTGTAC AAAAGATCAA ACACTGTTTT AGAAAACTTC |
| 106 | Representative HBV A3 sequence, GenBank Acc. No. AB194951, positions 1-900 | 1 TTCCACAAAT TCCACCAAG CTCTGCAAGA TCCCAGAGTC AGGGGCCTGT ATCTTCCTGC<br>61 TGGTGGCTCC AGTTCAGGAA CAGTCAACCC TGCTCCGAAT ATTGCCTCTC ACATCTCGTC<br>121 AATCTCCTCG AGGATTGGGG ACCCTGCGCC GAACATGGAG AACATCACAT CAGGATTCCT<br>181 AGGACCCCTG CTCGTGTTAC AGGCGGGGTT TTTCTCGTTG ACAAAAATCC TCACAATACC<br>241 GCAGAGTCTA GACTCGTGGT GGACTTCTCT CAATTTTCTA GGGGGAGCAC CCGTGTGTCT<br>301 TGGCCAAAAT TCGCAGTCCC CAACCTCCAA TCACTCACCA ACCTCCTGTC CTCCAATTTG<br>361 TCCTGGTTAT CGCTGGATGT GTCTGCGGCG TTTTATCATA TTCCTCTTCA TCCTGCTGCT<br>421 ATGCCTCATC TTCTTATTGG TTCTTCTGGA TTGTCAAGGT ATGTTGCCCG TTTGTCCTCT<br>481 AATTCCAGGA TCCACAACCA CCAGTACGGG ACCCTGCAGA ACCTGCACGA CTCCTGCTCA<br>541 AGGCAACTCT ATGTTTCCCT CATGTTGCTG TACAAAACCT ACGGACGGAA ATTGCACCTG<br>601 TATTCCCATC CCATCATCCT GGGCTTTCGC AAAATACCTA TGGGGGTGGG CCTCAGTCCG<br>661 TTTCTCCTGG CTCAGTTTAC TAGTGCCATT TGTTCAGTGG TTCGTAGGGC TTTCCCCCAT<br>721 TGTTTGGCTT TCAGCTATAT GGATGATGTG GTATTGGGGG CCAAGTCTGT ACAACATCTT<br>781 GAGTCCCTTT ATACCGCTGT TACCAATTTT CTTTTGGCTT TGGGCATACA TTTAAACCCT<br>841 AACAAAACAA AAAGATGGGG TTATTCCCTT AACTTCATGG GATACATAAT TGGAAGTTGG |
| 107 | Representative HBV B1 sequence, GenBank Acc. No. AB014366, positions 1-900 | 1 TTCCACCACT TTCCACCAAA CTCTTCAAGA TCCCAGAGTC AGGGCTCTGT ACCTTCCTGC<br>61 TGGTGGCTCC AGTTCAGGAA TAGTAAGCCC TGCTCAGAAT ACTGTCTCTG CCATATCGTC<br>121 AATCTTATCG ACGACTGGGG ACCCTGTGCC GAACATGGAG AACATCGCAT CAGGACTCCT<br>181 AGGACCCCTG CTCGTGTTAC AGGCGGGGTT TTTCTCGTTG ACAAAAATCC TCACAATACC<br>241 ACAGAGTCTA GACTCGTGGT GGACTTCTCT CAGTTTTCTA GGGGGAACAC CCGTGTGTCT<br>301 TGGCCAAAAT TCGCAGTCCC AAATCTCCAG TCACTCACCA ACCTGTTGTC CTCCAATTTG<br>361 TCCTGGTTAT CGCTGGATGT ATCTGCGGCG TTTTATCTC TGCCTCTGCA TCCTGCTGCT<br>421 ATGCCTCATC TTCTTGTTGG TTCTTCTGGA CTATCAAGGT ATGTTGCCCG TTTGTCCTCT<br>481 AATTCCAGGA TCATCAACCA CCAGCACGGG ACCATGCAAG ACCTGCACAA CTCCTGCTCA<br>541 AGGAACCTCT ATGTTTCCCT CATGTTGCTG TACAAAACCT ACGGACGGAA ACTGCACCTG<br>601 TATTCCCATC CCATCATCTT GGGCTTTCGC AAAATTCCTA TGGGAGTGGG CCTCAGTCCG<br>661 TTTCTCTTGG CTCAGTTTAC TAGTGCCATT TGTTCAGTGG TTCGTAGGGC TTTCCCCCAC<br>721 TGTCTGGCTT TCAGTTATAT GGATGATGTG GTATTGGGGG CCAAGTCTGT ACAACATCTT<br>781 GAGTCCCTTT ATGCCGCTGT TACCAATTTT CTTTTGTCTT TGGGTATACA TTTAAACCCT<br>841 CACAAAACAA AAAGATGGGG ATATTCCCTT AATTTCATGG GATATGTAAT TGGGAGTTGG |
| 108 | Representative HBV B2 sequence, GenBank Acc. No. AY596111, positions 1-900 | 1 CTCCACCACT TTCCACCAAA CTCTTCAAGA TCCCAGAGTC AGGGCCCTGT ACTTTCCTGC<br>61 TGGTGGCTCC AGTTCAGGAA CAGTGAGCCC TGCTCAGAAT ACTGTCTCTG CCATATCGTC<br>121 AATCTTATCG AAGACTGGGG ACCCTGTACC GAACATGGAG AACATCGCAT CAGGACTCCT<br>181 AGGACCCCTG CTCGTGTTAC AGGCGGGGTT TTTCTCGTTG ACAAAAATCC TCACAATACC<br>241 ACAGAGTCTA GACTCGTGGT GGACTTCTCT CAGTTTTCTA GGGGAAACAC CCGTGTGTCT<br>301 TGGCCAAAAT TCGCAGTCCC AAATCTCCAG TCACTCACCA ACCTGTTGTC CTCCAATTTG<br>361 TCCTGGTTAT CGCTGGATGT GTCTGCGGCG TTTTATCATC TTCCTCTGCA TCCTGCTGCT<br>421 ATGCCTCATC TTCTTGTTGG TTCTTCTGGA CTATCAAGGT ATGTTGCCCG TTTGTCCTCT<br>481 AATTCCAGGA TCATCAACAA CCAGCACCGG ACCATGCAAA ACCTGCACAA CTTCTGCTCA<br>541 AGGAACCTCT ATGTTTCCCT CATGTTGCTG TACAAAACCT ACGGACGGAA ACTGCACCTG<br>601 TATTCCCATC CCATCATCTT GGGCTTTCGC AAAATACCTA TGGGAGTGGG CCTCAGTCCG<br>661 TTTCTCTTGG CTCAGTTTAC TAGTGCCATT TGTTCAGTGG TTCGTAGGGC TTTCCCCCAC<br>721 TGTCTGGCTT TCAGTTATAT GGATGATGTG GTTTGGGGG CCAAGACTGT ACAGCATCTT<br>781 GAGTCCCTTT ATGCCGCTGT TACCAATTTT CTTTTGTCTT TGGGCATACA TTTAAACCCT<br>841 CACAAAACAA AAAGATGGGG ATATTCCCTT AACTTCATGG GATATGTAAT TGGGAGTTGG |
| 109 | Representative HBV B3 sequence, GenBank Acc. No. M54923, positions 1-900 | 1 CTCCACCACG TTCCACCAAA CTCTTCAAGA TCCCAGAGTC AGGGCTCTGT ACTTTCCTGC<br>61 TGGTGGCTCC AGTTCAGGAA CAGTAAACCC TGTTCAGAAC ACTGTCTCTT CCATATCGTC<br>121 AATCTTATCG AAGACTGGGG ACCCTGTGCC GAACATGGAG AACATCGCAT CAGGACTCCT<br>181 AGGACCCCTG CTCGTGTTAC AGGCGGGGTT TTTCTTGTTG ACAAAAATCC TCACAATACC<br>241 ACAGAGTCTA GACTCGTGGT GGACTTCTCT CAATTTTCTA GGGGGAACAC CCGTGTGTCT<br>301 TGGCCAAAAT TCGCAGTCCC AAATCTCCAG TCACTCACCA ACTTGTTGTC CTCCGATTTG<br>361 TCCTGGTTAT CGCTGGATGT GTCTGCGGCG TTTTATCATC TTCCTCTGCA TCCTGCTGCT<br>421 ATGCCTCATC TTCTTGTTGG TTCTTCTGGA CTATCAAGGT ATGTTGCCCG TTTGTCCTCT<br>481 AATTCCAGGA TCATCAACCA CCAGCACCGG ACCATGCAAA ACCTGCACGA CTCCTGCTCA<br>541 AGGAACCTCT ATGTTTCCCT CATGTTGCTG TACAAAACCT ACGGACGGAA ACTGCACCTG<br>601 TATTCCCATC CCATCATCTT GGGCTTTCGC AAAATACCTA TGGGAGTGGG CCTCAGTCCG<br>661 TTTCTCTTGG CTCAGTTTAC TAGTGCCATT TGTTCAGTGG TTCGTAGGGC TTTCCCCCAC<br>721 TGTCTGGCTT TCAGTTATAT GGATGATGTG GTTTGGGGG CCAAGTCTGT ACAACATCTT<br>781 GAGTCCCTTT ATGCCGCTGT TACCAATTTT CTTTTGTCTT TGGGTATACA TTTAAACCCT<br>841 CAGAAAACAA AAAGATGGGG CTACTCCCTC AACTTCATGG GGTATGTAAT TGGAAGTTGG |
| 110 | Representative HBV B4 sequence, GenBank Acc. No. AB073835, positions | 1 CTCCACCACT TTCCATCAAA CTCTTCAAGA TCCCAGAGTC AGGGCTCTGT ACTTTCCTGC<br>61 TGGTGGCTCC AGTTCAGGAA TAGTAAACCC TGCTCAGAAT ACTGCCTCTG CCATATCATC<br>121 AACCTTCTCG AAGACTGGGG ACCCTGTACC GAACATGGAG AACATCGCAT CAGGACTCCT<br>181 AGGACCCCTG CTCGTGTTAC AGGCGGGGTT TTTCTCGTTG ACAAAAATCC TCACAATACC |

TABLE OF SEQUENCES

In the following table, lower case letters indicate 2'Ome RNA and upper case letter indicate DNA.

| SEQ ID NO | Description | Sequence |
|---|---|---|
| | 1-900 (continued) | 241 ACAGAGTCTA GACTCGTGGT GGACTTCTCT CAATTTTCTA GGGGGAACAC CCGTGTGTCT<br>301 TGGCCAAAAT TCGCAGTCCC AAATCTCCAG TCACTCACCA ACTTGTTGTC CTCCAACTTG<br>361 TCCTGGTTAT CGCTGGATGT ATCTGCGGCG TTTTATCATA TTCCTCTGCA TCCTGCTGCT<br>421 ATGCCTCATC TTCTTGTTGG TTCTTCTGGA CTATCAAGGT ATGTTGCCCG TTTGTCCTCT<br>481 AATTCCAGGA TCATCAACCA CCAGCACCGG ACCCTGCAGA ACCTGCACGA CTCCTGCTCA<br>541 AGGAACCTCT ATGTTTCCCT CATGTTGCTG TACAAAACCT ACGGACGGAA ACTGCACCTG<br>601 TATTCCCATC CCATCATCTT GGGCTTTCGC AAAATTCCTA TGGGAGTGGG CCTCAGTCCG<br>661 TTTCTCTTGG CTCAGTTTAC TAGTGCCGTT TGTTCAGTGG TTCGTAGGGC TTTCCCCCAC<br>721 TGTCTGGCTT TCAGTTATAT GGATGATGTG GTATTGGGGG CCAAATCTGT ACAACATCTT<br>781 GAGTCCCTTT ATGCCGCTGT TACCAATTTT CTTTTGTCTT TGGGTATACA TTTAAACCCT<br>841 CACAAAACAA AAAGATGGGG ATATTCCCTT AATTTCATGG GATATGTAAT TGGTAGTTGG |
| 111 | Representative HBV C1 sequence, GenBank Acc. No. AY123424, positions 1-900 | 1 AACTCCACAA CATTCCACCA AGCTCTGCTA GACCCCAGAG TGAGGGGCCT ATACTTTCCT<br>61 GCTGGTGGCT CCAGTTCCGG AACAGTAAAC CCTGTTCCGA CTACTGCCTC ACCCATATCG<br>121 TCAATCTTCT CGAGGACTGG GGACCCTGCA CCGAACATGG AGAGCACAAC ATCAGGATTC<br>181 CTAGGACCCC TGCTCGTGTT ACAGGCGGGG TTTTTCTTGT TGACAAGAAT CCTCACAATA<br>241 CCACAGAGTC TAGACTCGTG GTGGACTTCT CTCAATTTTC TAGGGGGAGC ACCCACGTGT<br>301 CTTGGCCAAA ATTCGCAGTC CCCAACCTCC AATCACTCAC CAACCTCTTG TCCTCCAATT<br>361 TGTCCTGGTT ATCGTTGGAT GTGTCTGCGG CGTTTTATCA TATTCCTCTT CATCCTGCTG<br>421 CTATGCCTCA TCTTCTTGTT GGTTCTTCTG GACTACCAAG GTATGTTGCC CGTTTGTCCT<br>481 CTACTTCCAA GAACATCAAC TACCAGCACG GGACCATGCA AGACCTGCAC GATTCCTGCT<br>541 CAAGGAACCT CTATGTTTCC CTCTTGTTGC TGTACAAAAC CTTCGGACGG AAACTGCACT<br>601 TGTATTCCCA TCCCATCATC TTGGGCTTTC GCAAGATTCC TATGGGAGTG GGCCTCAGTC<br>661 CGTTTCTCCT GGCTCAGTTT ACTAGTGCCA TTTGTTCAGT GGTTCGTAGG CTTTCCCCC<br>721 ACTGTTTGGC TTTCAGTTAT ATGGATGATG TGGTATTGGG GGCCAAGTCT GTACAACATC<br>781 TTGAGTCCCT TTTTACCTCT ATTACCAATT TTCTATTTGTC TTTGGGTATA CATTTGAACC<br>841 CCAATAAAAC CAAACGTTGG GGCTATTCCC TTAATTTCAT GGGATATGTA ATTGGATGTT |
| 112 | Representative HBV C2 sequence, GenBank Acc. No. AF223955, positions 1-900 | 1 CTCCAGCACA TTCCACCAAG CTCTGCTAGA TCCCAGAGTG AGGGGCCTAT ACTTTCCTGC<br>61 TGGTGGCTCC AGTTCCGGAA CAGTAAACCC TGTTCCGACT ACTGCCTCTC CCATATCGTC<br>121 AATCTTCTCG AGGACTGGGG ACCCTGCACC GAATATGGAG AGCACCACAT CAGGATTCCT<br>181 AGGACCCCTG CTCGTGTTAC AGGCGGGGTT TTTCTTGTTG ACAAGAATCC TCACAATACC<br>241 ACAGAGTCTA GACTCGTGGT GGACTTCTCT CAATTTTCTA GGGGGAGCAC CCACGTGTCC<br>301 TGGCCAAAAT TTGCAGTCCC CAACCTCCAA TCACTCACCA ACCTCTTGTC CTCCAATTTG<br>361 TCCTGGTTAT CGCTGGATGT GTCTGCGGCG TTTTATCATC TTCCTCTTCA TCCTGCTGCT<br>421 ATGCCTCATC TTCTTGTTGG TTCTTCTGGA CTACCAAGGT ATGTTGCCCG TTTGTCCTCT<br>481 ACTTCCAGGA ACATCAACTA CCAGCACGGG ACCATGCAGG ACCTGCACGA TTCCTGCTCA<br>541 AGGAACCTCT ATGTTTCCCT CTTGTTGCTG TACAAAACCT TCGGACGGAA ATTGCACTTG<br>601 TATTCCCATC CCATCATCTT GGGCTTTCGC AAGATTCCTA TGGGAGTGGG CCTCAGTCCG<br>661 TTTCTCCTGG CTCAGTTTAC TAGTGCCATT TGTTCAGTGG TTCGTAGGGC TTTCCCCCAC<br>721 TGTTTGGCTT TCAGTTATAT GGATGATGTG GTATTGGGGG CCAAGTCTGT ACAACATCTT<br>781 GAATCCCTTT TACCGCTAT TACCAATTTT CTTTTGTCTT TGGGTATACA TTTAAACCCT<br>841 AATAAAACCA AACGTTGGGG CTACTCCCTT AACTTTATGG GATATGTCAT TGGAAGTTGG |
| 113 | Representative HBV C3 sequence, GenBank Acc. No. X75665, positions 1-900 | 1 CTCCACAACA TTCCAACAAG CTCTGCAGGA TCCCAGAGTC AGGGTCCTTT ATTTTCCTGC<br>61 TGGTGGCTCC AGTTCCGGAA CAGTAAACCC TGTTCCGACT ACTGCCTCTC TCATTTCGTC<br>121 AATCTTCTCG AGGACTGGGA ACCCTGTAAC GAACATGGAG AACACAACAT CAGGATTCCT<br>181 AGGACCCCTG CTCGTGTTAC AGGCGGGGTT TTTCTTGTTG ACAAAAATCC TCACAATACC<br>241 ACAGAGTCTA GACTCGTGGT GGACTTCTCT CAATTTTCTA GGGGGAGCAC CCGTGTGTCC<br>301 TGGCCAAAAT TCGCAGTCCC CAACCTCCAA TCACTCACCA ACCTCTTGTC CTCCAATTTG<br>361 TCCTGGCTAT CGCTGGATGT GTCTGCGGCG TTTTATCATC TTCCTCTTCA TCCTGCTGCT<br>421 ATGCCTCATC TTCTTGTTGG TTCTTCTGGA CTACCAAGGT ATGTTGCCCG TTTGTCCTCT<br>481 ACTTCCAGGA ACATCAACTA CCAGCACGGG ACCATGCAAG ACCTGCACGA TTCCTGCTCA<br>541 AGGAACCTCT ATGTTTCCCT CATGTTGCTG TACAAAACCT TCGGACGGAA ACTGCACTTG<br>601 TATTCCCATC CCATCATCCT GGGCTTTCGG AAGATTCCTA TGGGAGTGGG CCTCAGTCCG<br>661 TTTCTCCTGG CTCAGTTTAC TAGCGCCATT TGTTCAGTGG TTCGTAGGGC TTTCCCCCAC<br>721 TGTTTGGCTT TCAGTTATAT GGATGATGTG GTATTGGGGG CCAAGTCTGT ACAACATCTT<br>781 GAGTCCCTTT ATACCTCTAT TACCAATTTT CTTTTGTCTT TGGGTATACA TTTAAACCCT<br>841 AATAAAACCA AAAGATGGGG CTATTCCCTT AACTTCATGG CTATGTAAT TGGAAGTTGG |
| 114 | Representative HBV D1 sequence, GenBank Acc. No. AB104712, positions 1-900 | 1 AACTCCACTA CCTTCCACCA AACTCTGCAA GATCCCAGAG TGAGAGGCCT GTATTTCCCT<br>61 GCTGGTGGCT CCAGTTCAGG AACAGTAAAC CCTGTTCCGA CTACTGTCTC TCACATATCG<br>121 TCAATCTTCT CGAGGATTGG GGACCCTGCG CTGAACATGG AGAACATCAC ATCAGGATTC<br>181 CTAGGACCCC TGCTCGTGTT ACAGGCGGGG TTTTTCTTGT TGACAAGAAT CCTCACAATA<br>241 CCGCAGAGTC TAGACTCGTG GTGGACTTCT CTCAATTTTC TAGGGGGAAC TACCGTGTGT<br>301 CTTGGCCAAA ATTCGCAGTC CCCAACCTCC AATCACTCAC CAACCTCCTG TCCTCCAACT<br>361 TGTCCTGGTT ATCGCTGGAT GTGTCTGCGG CGTTTTATCA TCTTCCTCTT CATCCTGCTG<br>421 CTATGCCTCA TCTTCTTGTT GGTTCTTCTG GACTATCAAG GTATGTTGCC CGTTTGTCCT<br>481 CTAATTCCAG GATCTTCAAC TACCAGCACG GGACCATGCA GAACCTGCAC GACTCCTGCT<br>541 CAAGGAACCT CTATGTATCC CTCCTGCTGC TGTACCAAAC CTTCGGACGG AAATTGCACC<br>601 TGTATTCCCA TCCCATCATC CTGGGCTTTC GGAAAATTCC TATGGGAGTG GGCCTCAGCC |

TABLE OF SEQUENCES

In the following table, lower case letters indicate 2'Ome RNA and upper case letter indicate DNA.

| SEQ ID NO | Description | Sequence |
|---|---|---|
| | | 661 CGTTTCTCCT GGCTCAGTTT ACTAGTGCCA TTTGTTCAGT GGTTCGTAGG GCTTTCCCCC<br>721 ACTGTTTGGC TTTCAGTTAT ATGGATGATG TGGTATTGGG GGCCAAGTCT GTACAGCATC<br>781 TTGAGTCCCT TTTTACCGCT GTTACCAATT TTCTTTTGTC TTTGGGTATA CATTTAAACC<br>841 CTAACAAAAC AAAAAGATGG GGTTACTCTT TACATTTCAT GGGTTATGTC ATTGGATGTT |
| 115 | Representative HBV D2 sequence, GenBank Acc. No. AB205126, positions 1-900 | 1 AACTCCACTA CCTTCCACCA AACTCTGCAA GATCCCAGAG TGAGAGGCCT GTATTTCCCT<br>61 GCTGGTGGCT CCAGTTCAGG AACAGTAAAC CCTGTTCCGA CTACTGTCTC TCACATATCG<br>121 TCAATCTTCT CGAGGATTGG GGACCCTGCG CTGAACATGG AGAACATCAC ATCAGGATTC<br>181 CTAGGACCCC TGCTCGTGTT ACAGGCGGGG TTTTTCTTGT TGACAAGAAT CCTCACAATA<br>241 CCGCAGAGTC TAGACTCGTG GTGGACTTCT CTCAATTTTC TAGGGGGAAC TACCGTGTGT<br>301 CTTGGCCAAA ATTCGCAGTC CCCAACCTCC AATCACTCAC CAACCTCCTG TCCTCCAACT<br>361 TGTCCTGGTT ATCGCTGGAT GTGTCTGCGG CGTTTTATCA TCTTCCTCTT CATCCTGCTG<br>421 CTATGCCTCA TCTTCTTGTT GGTTCTTCTG GACTATCAAG GTATGTTGCC CGTTTGTCCT<br>481 CTAATTCCAG GATCTTCAAC TACCAGCACG GGACCATGCA GAACCTGCAC GACTCCTGCT<br>541 CAAGGAACCT CTATGTATCC CTCCTGCTGC TGTACCAAAC CTTCGGACGG AAATTGCACC<br>601 TGTATTCCCA TCCCATCATC CTGGGCTTTC GGAAAATTCC TATGGGAGTG GGCCTCAGCC<br>661 CGTTTCTCCT GGCTCAGTTT ACTAGTGCCA TTTGTTCAGT GGTTCGTAGG GCTTTCCCCC<br>721 ACTGTTTGGC TTTCAGTTAT ATGGATGATG TGGTATTGGG GGCCAAGTCT GTACAGCATC<br>781 TTGAGTCCCT TTTTACCGCT GTTACCAATT TTCTTTTGTC TTTGGGTATA CATTTAAACC<br>841 CTAACAAAAC AAAAAGATGG GGTTACTCTT TACATTTCAT GGGTTATGTC ATTGGATGTT |
| 116 | Representative HBV D3 sequence, GenBank Acc. No. AY233291, positions 1-900 | 1 TTCCACAACC TTCCACCAAA CTCTGCAAGA TCCCAGAGTG AGAGGCCTGT ATTTCCCTGC<br>61 TGGTGGCTCC AGTTCAGGAA CAGTAAACCC TGTTCCGACT ACTGCCTCTC CCTTATCGTC<br>121 AATCTTCTCG AGGATTGGGA CCCTGCGCC GAACATGGAG AACATCACAT CAGGATTCCT<br>181 AGGACCCCTG CTCGTGTTAC AGGCGGGGTT TTTCTTGTTG ACAAGAATCC TCACAATACC<br>241 GCAGAGTCTA GACTCGTGGT GGACTTCTCT CAATTTTCTA GGGGGAACTA CCGTGTGTCT<br>301 TGGCCAAAAT TCGCAGTCCC CAACCTCCAA TCACTCACCA ACCTCCTGTC CTCCAACTTG<br>361 TCCTGGTTAT CGCTGGATGT GTCTGCGGCG TTTTATCATC TTCCTCTTCA TCCTGCTGCT<br>421 ATGCCTCATC TTCTTGTTGG TTCTTCTGGA CTATCAAGGT ATGTTGCCCG TGTGTCCTCT<br>481 AATTCCAGGA TCCTCAACCA CCAGCACGGG ACCATGCCGA ACCTGCACGA CTCCTGCTCA<br>541 AGGAACCTCT ATGTATCCCT CCTGTTGCTG TACCAAACCT TCGGACGGAA ATTGCACCTG<br>601 TATTCCCATC CCATCATCCT GGCCTTTCGG AAAATTCCTA TGGGAGTGGG CCTCAGCCCG<br>661 TTTCTCCTGG CTCAGTTTAC TAGTGCCATT TGTTCAGTGG TTCGTAGGGC TTTCCCCCAC<br>721 TGTTTGGCTT TCAGTTATAT GGATGATGTG GTATTGGGGG CCAAGTCTGT ACAGCATCTT<br>781 GAGTCCCTTT TACCGCTGT TACCAATTTT CTTTTGTCTT TGGGTATACA TTTAAACCCT<br>841 AACAAAACAA AGAGATGGGG TTACTCTCTA AATTTTATGG GGTATGTCAT TGGATGTTAT |
| 117 | Representative HBV D4 sequence, GenBank Acc. No. AB048702, positions 1-900 | 1 CTCCACAACC TTCCACCAAA CTCTGCAAGA TCCCAGAGTG AGAGGCCTGT ATCTCCCTGC<br>61 TGGTGGCTCC AGTTCAGGAA CAGTAAACCC TGTTCCGACT ACTGCCTCTC CCATATCGTC<br>121 AATCTTCTCG AGGATTGGGA CCTTGCGCT GAACATGGAG AACATCACAT CAGGATTCCT<br>181 AGGACCCCTG CTCGTGTTAC AGGCGGGGTT TTTCTTGTTG ACAAGAATCC TCACAATACC<br>241 GCAGAGTCTA GACTCGTGGT GGACTTCTCT CAATTTTCTA GGGGGAACTA CCGTGTGTCT<br>301 TGGCCAAAAT TCGCAGTCCC CAACCTCCAA TCACTCACCA ACCTCCTGTC CTCCAACTTG<br>361 TCCTGGTTAT CGCTGGATGT TCTGCGGCG TTTTATCATC TTCCTCTTCA TCCTGCTGCT<br>421 ATGCCTCATC TTCTTGTTGG TTCTTCTGGA TTATCAAGGT ATGTTGCCCG TTTGTCCTCT<br>481 AATTCCAGGA TCATCAACCA CCAGCACGGG ACCCTGCAGA ACCTGCACGA CTCCTGCTCA<br>541 AGGAACCTCT ATGTATCCCT CCTGTTGCTG TACAAAACCT TCGGATGGAA ACTGCACCTG<br>601 TATTCCCATC CCATCATCCT GGGCTTTCGG AAAATTCCTA TGGGAGTGGG CCTCAGCCCG<br>661 TTTCTCTTGG CTCAGTTTAC TAGTGCCATT TGTTCAGTGG TTCGTAGGGC TTTCCCCCAC<br>721 TGTTTGGCTT TCAGTTATAT GGATGATGTG GTATTGGGGG CCAAGTCTGT ACAGCACCTT<br>781 GAGTCCCTTT TTACCGCTGT TACCAATTTT CTTTTGTCTT TGGGTATACA TTTAAACCCT<br>841 AACAAAACAA AAAGATGGGG TTATTCTCTA AATTTCATGG CTATGTCAT TGGAAGTTGG |
| 118 | Representative HBV E sequence, GenBank Acc. No. AB205191, positions 1-900 | 1 TTCCACAACA TTCCACCAAG CTCTGCAGGA TCCCAGAGTA AGAGGCCTGT ATTTTCCTGC<br>61 TGGTGGCTCC AGTTCCGGAA CAGTAAACCC TGTTCCGACT TCATCTCGTC<br>121 AATCTTCTCG AGGATTGGGG ACCCTGCACC GAACATGGAA GGCATCACAT CAGGATTCCT<br>181 AGGACCCCTG CTCGTGTTAC AGGCGGGGTT TTTCTTGTTG ACAAAATCC TCACAATACC<br>241 GCAGAGTCTA GACTCGTGGT GGACTTCTCT CAATTTTCTA GGGGGAGCTC CCGTGTGTCT<br>301 TGGCCAAAAT TCGCAGTCCC CAACCTCCAA TCACTCACCA ACCTCTTGTC CTCCAATTTG<br>361 TCCTGGCTAT CGCTGGATGT GTCTGCGGCG TTTTATCATC TTCCTCTTCA TCCTGCTGCT<br>421 ATGCCTCATC TTCTTGTTGG TTCTTCTGGA CTATCAAGGT ATGTTGCCCG TTTGTCCTCT<br>481 AATTCCAGGA TCATCAACCA CCAGTACGGG ACCCTGCCGA ACCTGCACGA CTCTTGCTCA<br>541 AGGAACCTCT ATGTTTCCT CATGTTGCTG TTCAAAACCT TCGGACGGAA ATTGCACTTG<br>601 TATTCCCATC CCATCATCAT GGGCTTTCGG AAAATTCCTA TGGGAGTGGG CCTCAGCCCG<br>661 TTTCTCCTGG CTCAGTTTAC TAGTGCCATT TGTTCAGTGG TTCGCCGGGC TTTCCCCCAC<br>721 TGTCTGGCTT TCAGTTATAT GGATGATGTG GTATTGGGGG CCAAGTCTGT ACAACATCTT<br>781 GAGTCCCTTT ATACCGCTGT TACCAATTTT CTTTTGTCTT TGGGTATACA TTTAAATCCA<br>841 AACAAAACAA AAAGATGGGG ATATTCCCTA AATTTCATGG GTTATGTAAT TGGAAGTTGG |
| 119 | Representative HBV F1a sequence, | 1 GAACTCAACT CAGTTCCACC AGGCTCTGTT AGATCCGAGG GTAAGGGCTC TGTATTTTCC<br>61 TGCTGGTGGC TCCAGTTCAG AGACACAGAA CCCTGCTCCG ACTATTGCCT CTCTCACATC |

US 11,220,719 B2

73                                                                 74

-continued

TABLE OF SEQUENCES
In the following table, lower case letters indicate 2'Ome RNA and upper case letter indicate DNA.

| SEQ ID NO | Description | Sequence |
|---|---|---|
| | GenBank Acc. No. AY090459, positions 1-900 | 121 ATCAATCTTC TTGAAGACTG GGGGCCCTGC TATGAACATG GACAACATCA CATCAGGACT<br>181 CCTAGGACCC CTGCTCGTGT TACAGGCGGT GTGTTTCTTG TTGACAAAAA TCCTCACAAT<br>241 ACCACAGAGT CTAGACTCGT GGTGGACTTC TCTCAATTTT CTAGGGGGAA CACCAGGGTG<br>301 TCCTGGCCAA AATTCGCAGT CCCCAACCTC CAATCACTTA CCAACCTCCT GTCCTCCAAC<br>361 TTGTCCTGGT TATCGCTGGA TGTGTCTGCG GCGTTTTATC ATCTTCCTCT TCATCCTGCT<br>421 GCTATGCCTC ATCTTCTTGT TGGTTCTTCT GGACTATCAA GGTATGTTGC CCGTTTGTCC<br>481 TCTACTTCCA GGATCCACGA CCACCAGCAC GGGACCATGC AAAACCTGCA CAACTCTTGC<br>541 TCAAGGAACC TCTATGTTTC CCTCCTGCTG CTGTTCCAAA CCTTCGGACG GAAACTGCAC<br>601 TTGTATTCCC ATCCCATCAT CCTGGGCTTT AGGAAAATAC CTATGGGAGT GGGCCTCAGC<br>661 CCGTTTCTCC TGGCTCAGTT TACTAGTGCA ATTTGTTCAG TGGTGCGTAG GGCTTTCCCC<br>721 CACTGTTTGG CTTTTAGTTA TATGGATGAT CTGGTATTGG GGGCCAAATC TGTGCAGCAT<br>781 CTTGAGTCCC TTTATACCGC TGTTACCAAT TTTCTGTTAT CTGTGGGTAT CCATTTAAAT<br>841 ACCTCTAAAA CGAAAAGATG GGCTATACT TTAAATTTCA TGGGATATGT TATTGGCAGT |
| 120 | Representative HBV F1b sequence, GenBank Acc. No. AF223963, positions 1-900 | 1 CTCCACTCAG TTCCACCAGG CTCTGTTAGA TCCGAGGGTA AGGGCTCTGT ATTTTCCTGC<br>61 TGGTGGCTCC AGTTCAGAGA CACAGAACCC TGCTCCGACT ATTGCCTCTC TCACATCATC<br>121 AATCTTCTTG AAGACTGGGG GCCCTGCTAC GAACATGGAC AACATCACAT CAGGACTCCT<br>181 AGGACCCCTG CTCGTGTTAC AGGCGGTGTG TTTCTTGTTG ACAAAAATCC TCACAATACC<br>241 ACAGAGTCTA GACTCGTGGT GGACTTCTCT CAATTTTCTA GGGGGAACAC CCGGGTGTCC<br>301 TGGCCAAAAT TCGCAGTCCC CAACCTCCAA TCACTTACCA ACCTCCTGTC CTCCAACTTG<br>361 TCCTGGCTAT CGCTGGATGT GTCTGCGGCG TTTTATCATC TTCCTCTTCA TCCTGCTGCT<br>421 ATGCCTCATC TTCTTGTTGG TTCTTCTGGA CTATCAAGGT ATGTTGCCCG TTTGTCCTCT<br>481 ACTTCCAGGA TCCACGACCA CCAGCACGGG ACCATGCAAA ACCTGCACAA CTCTTGCTCA<br>541 AGGAACCTCT ATGTTTCCCT CTTGCTGCTG TTCCAAACCC TCGGACGGAA ACTGCACTTG<br>601 TATTCCCATC CCATCATCCT GGGCTTTAGG AAAATACCTA TGGGAGTGGG CCTCAGCCCG<br>661 TTTCTCCTGG CTCAGTTTAC TAGTGCAATT TGTTCAGTGG TGCGTAGGGC TTTCCCCCAC<br>721 TGTCTGGCTT TTAGTTATAT GGATGATCTG GTATTGGGGG CCAAATCTGT GCAGCATCTT<br>781 GAGTCCCTTT ATACCGCTGT TACCAATTTT CTGTTATCTG TGGGTATCCA TTTAAATACC<br>841 TCGAAAACAA AAAGATGGGG TTATACCCTA AATTTCATGG TTATGTTAT TGGCAGTTGG |
| 121 | Representative HBV F2 sequence, GenBank Acc. No. AY311369, positions 1-900 | 1 CTCAACCCAG TTCCACCAGG CTCTGTTGGA TCCCAGGGTA AGGGCTCTGT ACTTCCTGC<br>61 TGGTGGCTCC AGTTCAGGGA CACAGAACCC TGCTCCGACT ATTGCCTCTC TCACATCATC<br>121 AATCTTCTCG AAGACTGGGG GCCCTGCTAT GAACATGGAC AACATTACAT CAGGACTCCT<br>181 AGGACCCCTG CTCGTGTTAC AGGCGGTGTG TTTCTTGTTG ACAAAAATCC TCACAATACC<br>241 ACAGAGTCTA GACTCGTGGT GGACTTCTCT CAATTTTCTA GGGGGACTAC CCGGGTGTCC<br>301 TGGCCAAAAT TCGCAGTCCC CAACCTCCAA TCACTTACCA ACCTCCTGTC CTCCAACTTG<br>361 TCCTGGCTAT CGTTGGATGT GTCTGCGGCG TTTTATCATC TTCCTCTTCA TCCTGCTGCT<br>421 ATGCCTCATC TTCTTGTTGG TTCTTCTGGA CTATCAAGGT ATGTTGCCCG TTTGTCCTCT<br>481 ACTTCCAGGA TCCACGACCA CCAGCACGGG ACCCTGCAAA ACCTGCACAA CTCTTGCACA<br>541 AGGAACCTCT ATGTTTCCCT CCTGTTGCTG TTCCAAACCC TCGGACGGAA ACTGCACTTG<br>601 TATTCCCATC CCATCATCTT GGGCTTTAGG AAAATACCTA TGGGAGTGGG CCTCAGCCCG<br>661 TTTCTCCTGG CTCAGTTTAC TAGTGCAATT TGTTCAGTGG TGCGTCGGGC TTTCCCCCAC<br>721 TGTTTGGCTT TTAGTTATAT GGATGATCTG GTATTGGGGG CCAAATCTGT GCAGCATCTT<br>781 GAGTCCCTTT ATACCGCTGT TACCAATTTT CTGTTATCTG TGGGTATCCA TTTAAATACC<br>841 TCTAAAACAA AAAGATGGGG GTACTCCCTA CATTTTATGG CTATGTCAT TGGTAGTTGG |
| 122 | Representative HBV F3 sequence, GenBank Acc. No. AB036915, positions 1-900 | 1 CTCAACCCAG TTCCACCAGG CTCTGTTAGA TCCGAGGGTA AGGGCTCTGT ATTTTCCTGC<br>61 TGGTGGCTCC AGTTCAGGGA CACAGAACCC TGTTCCGACT ATTGCCTCTC TCACATCATC<br>121 AATCTTCTCG AAGACTGGGG GCCCTGCTAT GAACATGGAG AACATCACAT CAGGACTCCT<br>181 AGGACCCCTG CTCGTGTTAC AGGCGGTGTG TTTCTTGTTG ACAAAAATCC TCACAATACC<br>241 ACAGAGTCTA GACTCGTGGT GGACTTCTCT CAATTTTCTA GGGGGACTAC CCGGGTGTCC<br>301 TGGCCAAAAT TCGCAGTCCC CAACCTCCAA TCACTTACCA ACCTCCTGTC CTCCAACTTG<br>361 TCCTGGCTAT CGTTGGATGT GTCTGCGGCG TTTTATCATC TTCCTCTTCA TCCTGCTGCT<br>421 ATGCCTCATC TTCTTGTTGG TTCTTCTGGA CTATCAAGGT ATGTTGCCCG TTTGTCCTCT<br>481 ACTTCCAGGA TCCACAACCA CCAGCACGGG ACCATGCAAA ACCTGCACAA CTCTTGCTCA<br>541 AGGAACCTCT ATGTTTCCCT CCTGTTGCTG TTCCAAACCC TCGGACGGAA ACTGCACCTG<br>601 TATTCCCATC CCATCATCTT GGGCTTTAGG AAAATACCTA TGGGAGTGGG CCTCAGCCCG<br>661 TTTCTCCTGG CTCAGTTTAC TAGTGCAATT TGTTCAGTGG TGCGTAGGGC TTTCCCCCAC<br>721 TGTCTGGCTT TTAGTTATAT GGATGATCTG GTATTGGGGG CCAAATCTGT GCAGCATCTT<br>781 GAGTCCCTTT ATACCGCTGT TACCAATTTT TTGTTATCTG TGGGTATCCA TTTAAATACT<br>841 TCTAAAACAA AAAGATGGGG TTACAACCTA CATTTCATGG TTATGTTAT TGGTAGTTGG |
| 123 | Representative HBV F4 sequence, GenBank Acc. No. AB166850, positions 1-900 | 1 CTCAACCCAG TTCCACCAGG CCCTGTTGGA TCCGAGGGTA AGGGCTCTGT CTCCTCCTGC<br>61 TGGTGGCTCC AGTTCAGAGA CACAGAACCC TGCTCCGACT ATTGCCTCTC TCACATCATC<br>121 AATCTTCTCG AAAACTGGGG GCCCTGCTAT GAACATGGAC AACATCACAT CAGGACTCCT<br>181 AGGACCCCTG CTCGTGTTAC AGGCGGTGTG TTTCTTGTTG ACAAAAATCC GCACAATACC<br>241 ACAGAGTCTA GACTTGTGGT GGACTTCTCT CAATTTTCTA GGGGACTAC CCGGGTGTCC<br>301 TGGCCAAAAT TCGCAGTCCC CAACCTCCAA TCACTTACCA ACCTCCTGTC CTCCAACTTG<br>361 TCCTGGCTAT CGTTGGATGT GTCTGCGGCG TTTTATCATC TTCCTCTTCA TCCTGCTGCT<br>421 ATGCCTCATC TTCTTGTTGG TTCTTCTGGA CTATCAAGGT ATGTTGCCCG TTTGTCCTCT<br>481 AATTCCAGGA TCTACGACCA CCAGCACGGG ACCATGCAAA ACCTGCACAA CTCTTGCTCA |

TABLE OF SEQUENCES
In the following table, lower case letters indicate 2'Ome RNA and upper case letter indicate DNA.

| SEQ ID NO | Description | Sequence |
|---|---|---|
| | | 541 AGGAACCTCT ATGTTTCCCT CCTGTTGCTG TTCAAAACCT TCGGACGGAA ACTGCACCTG<br>601 TATTCCCATC CCATCATCTT GGGCTTTAGG AAAATACCTA TGGGAGTGGG CCTCAGCCCG<br>661 TTTCTCCTGG CTCAGTTTAC TAGTGCAATT TGTTCAGTGG TGCGTAGGGC TTTCCCCCAC<br>721 TGTCTGGCTT TTAGTTATAT GGATGATCTG GTATTGGGGG CCAAATCTGT GCAGCATCTT<br>781 GAGTCCCTTT ATACCGCTGT TACCAATTTT CTGTTATCTG TGGGTATCCA TTTGAATACC<br>841 TCTAAAACAA AAAGATGGGG TTACAATTTA CATTTCATGG GTTATATCAT GGTAGTTGG |
| 124 | Representative HBV G sequence, GenBank Acc. No. AB064312, positions 1-900 | 1 CTCTACAGCA TTCCACCAAG CTCTACAAAA TCCCACAGTC AGGGGCCTGT ATCTTCCTGC<br>61 TGGTGGCTCC AGTTCAGGGA TAGTGAACCC TGTTCCGACT ATTGCCTCTC ACATCTCGTC<br>121 AATCTTCTCC AGGATTGGGG ACCCTGCACC GAACATGGAG AACATCACAT CAGGATTCCT<br>181 AGGACCCCTG CTCGTGTTAC AGGCGGGGTT TTTCTTGTTG ACAAGAATCC TCACAATACC<br>241 GCAGAGTCTA GACTCGTGGT GGACTTCTCT CAATTTTCTA GGGGGAGTGC CCGTGTGTCC<br>301 TGGCCTAAAT TCGCAGTCCC CAACCTCCAA TCACTCACCA ATCTCCTGTC CTCCAACTTG<br>361 TCCTGGCTAT CGCTGGATGT GTCTGCGGCG TTTTATCATA TTCCTCTTCA TCCTGCTGCT<br>421 ATGCCTCATC TTCTTGTTGG TTCTTCTGGA CTATCAAGGT ATGTTGCCCG TTTGTCCTCT<br>481 GATTCCAGGA TCCTCGACCA CCAGTACGGG ACCCTGCAAA ACCTGCACGA CTCCTGCTCA<br>541 AGGCAACTCT ATGTATCCCT CATGTTGCTG TACAAAACCT TCGGACGGAA ATTGCACCTG<br>601 TATTCCCATC CCATCATCTT GGGCTTTCGC AAAATACCTA TGGGAGTGGG CCTCAGTCCG<br>661 TTTCTCTTGG CTCAGTTTAC TAGTGCCATT TGTTCAGTGG TTCGTAGGGC TTTCCCCCAC<br>721 TGTCTGGCTT TCAGCTATAT GGATGATGTG GTATTGGGGG CCAAATCTGT ACAACATCTT<br>781 GAGTCCCTTT ATACCGCTGT TACCAATTTT CTTTTGTCTT TGGGTATACA TCTAAACCCT<br>841 GACAAAACAA AAAGATGGGG TTATTCCTTA AATTTTATGG GATATGTAAT GGAAGTTGG |
| 125 | Representative HBV H sequence, GenBank Acc. No. AB059659, positions 1-900 | 1 CTCAACACAG TTCCACCAAG CACTGTTAGA TCCGAGAGTA AGGGGTCTGT ATTTTCCTGC<br>61 TGGTGGCTCC AGTTCAGAAA CACAGACCC TGCTCCGACT ATTGCCTCTC TCACATCATC<br>121 AATCTTCTCG AAGACTGGGG ACCCTGCTAT GAACATGGAG AACATCACAT CAGGACTCCT<br>181 AGGACCCCTT CCCGTGTTAC AGGGGGTGTT TTTCTCGTTG ACAAAAATCC TCACAATACC<br>241 ACAGAGTCTA GACTCGTGGT GGACTTCTCT CAATTTTCTA GAGGTACCAC CCGGGTGTCC<br>301 TGGCCAAAAT TCGCAGTCCC CAATCTCCAA TCACTTACCA ACCTCCTGTC CTCCAACTTG<br>361 TCCTGGCTAT CGTTGGATGT GTCTGCGGCG TTTTATCATC TTCCTCTTCA TCCTGCTGCT<br>421 ATGCCTCATC TTCTTGTTGG TTCTTCTGGA CTATCAAGGT ATGTTGCCCG TGTGTCCTCT<br>481 ACTTCCAGGA TCTACAACCA CCAGCACGGG ACCCTGCAAA ACCTGCACCA CTCTTGCTCA<br>541 AGGAACCTCT ATGTTTCCCT CCTGCTGCTG TACCAAACCT TCGGACGGAA ATTGCACCTG<br>601 TATTCCCATC CCATCATCTT GGGCTTTCGG AAAATACCTA TGGGAGTGGG CCTCAGCCCG<br>661 TTTCTCTTGG CTCAGTTTAC TAGTGCAATT TGTTCAGTGG TGCGTAGGGC TTTCCCCCAC<br>721 TGTCTGGCTT TTAGTTATAT GGATGATTTG GTATTGGGGG CCAAATCTGT GCAGCATCTT<br>781 GAGTCCCTTT ATACCGCTGT TACCAATTTT TTGTTATCTG TGGGCATCCA TTTGAACACA<br>841 GCTAAAACAA AAAGGTGGGG TTATTCCTTA CACTTTATGG GTTATATAAT GGGAGTTGG |

---

What is claimed is:

1. A method of detecting Hepatitis B virus in a sample, comprising:
contacting the sample with at least first, second, third, and fourth amplification oligomers, thereby forming a composition,
performing a nucleic acid amplification reaction in the composition which produces at least first and second amplicons in the presence of a Hepatitis B virus nucleic acid, and quantifying the first and second amplicons, wherein:
the first amplicon is produced through extension of the first and second amplification oligomers in the presence of the Hepatitis B virus nucleic acid;
the second amplicon is produced through extension of the third and fourth amplification oligomers in the presence of the Hepatitis B virus nucleic acid;
the second amplification oligomer comprises a target-hybridizing sequence comprising at least 10 contiguous nucleotides of one of SEQ ID NOs: 20, 21, or 22;
the third amplification oligomer comprises a target-hybridizing sequence comprising at least 10 contiguous nucleotides of SEQ ID NO: 41; and
(a) the first amplification oligomer comprises the sequence of SEQ ID NO: 2 and the fourth amplification oligomer comprises a target-hybridizing sequence comprising at least 14 contiguous nucleotides of Hepatitis B virus sequence, the at least 14 contiguous nucleotides of Hepatitis B virus sequence comprising at least 10 contiguous nucleotides of one of SEQ ID NOs: 34 or 35; or
(b) the first amplification oligomer comprises a target-hybridizing sequence comprising at least 10 contiguous nucleotides of one of SEQ ID NOs: 2 or 3 and the fourth amplification oligomer comprises at least 14 contiguous nucleotides of Hepatitis B virus sequence, the at least 14 contiguous nucleotides of Hepatitis B virus sequence comprising at least 10 contiguous nucleotides of SEQ ID NO: 35, wherein one of the at least 10 contiguous nucleotides of SEQ ID NO: 35 is the inosine at position 30 of SEQ ID NO: 35; or
(c) the first amplification oligomer comprises a target-hybridizing sequence comprising at least 10 contiguous nucleotides of one of SEQ ID NOs: 2 or 3, the fourth amplification oligomer comprises a target-hybridizing sequence comprising at least 14 contiguous nucleotides of Hepatitis B virus sequence, the at least 14 contiguous nucleotides of Hepatitis B virus sequence comprising at least 10 contiguous nucleotides of one of SEQ ID NOs: 34 or 35, and the method further comprises contacting the sample or composition with a probe oligomer comprising the sequence of SEQ ID NO: 29, wherein the sequence of SEQ ID NO: 29 includes a c9 linker between nucleotides 33 and 34 of SEQ ID NO: 29.

2. The method of claim 1, wherein the first amplification oligomer comprises the sequence of SEQ ID NO: 2.

3. The method of claim 1, wherein the fourth amplification oligomer comprises at least 10 contiguous nucleotides of SEQ ID NO: 35, wherein one of the at least 10 contiguous nucleotides of SEQ ID NO: 35 is the inosine at position 30 of SEQ ID NO: 35.

4. The method of claim 3, wherein the fourth amplification oligomer comprises at least 14 contiguous nucleotides of SEQ ID NO: 35 including the inosine at position 30 of SEQ ID NO: 35.

5. The method of claim 3, wherein the fourth amplification oligomer comprises at least 18 contiguous nucleotides of SEQ ID NO: 35 including the inosine at position 30 of SEQ ID NO: 35.

6. The method of claim 3, wherein the fourth amplification oligomer comprises the sequence of SEQ ID NO: 35.

7. The method of claim 1, further comprising contacting the sample or composition with a probe oligomer comprising the sequence of SEQ ID NO: 29, wherein the sequence of SEQ ID NO: 29 includes a c9 linker between nucleotides 33 and 34 of SEQ ID NO: 29.

8. The method of claim 7, wherein the probe oligomer further comprises a non-nucleotide detectable label.

9. The method of claim 7, wherein the probe oligomer further comprises a fluorescent label.

10. The method of claim 9, wherein the probe oligomer further comprises a quencher, wherein the quencher absorbs fluorescence to a greater extent when the probe is free than when the probe is annealed to a target nucleic acid.

11. The method of claim 10, wherein the fluorescent label is attached to the 5'-terminus of the probe oligomer and the quencher is attached to the 3'-terminus of the probe oligomer, or the fluorescent label is attached to the 3'-terminus of the probe oligomer and the quencher is attached to the 5'-terminus of the probe oligomer.

12. The method of claim 1, wherein the nucleic acid amplification reaction is isothermal.

13. The method of claim 1, wherein the nucleic acid amplification reaction is transcription-mediated amplification.

14. The method of claim 1, further comprising performing a linear amplification reaction wherein at least one amplification oligomer is extended before performing the nucleic acid amplification that produces at least first and second amplicons in the presence of a Hepatitis B virus nucleic acid.

15. The method of claim 14, wherein the nucleic acid amplification that produces at least first and second amplicons in the presence of a Hepatitis B virus nucleic acid is an exponential amplification reaction.

16. The method of claim 1, wherein the second amplification oligomer comprises the sequence of SEQ ID NO: 20.

17. The method of claim 1, wherein the second amplification oligomer comprises the sequence of SEQ ID NO: 21.

18. The method of claim 1, wherein the second amplification oligomer comprises the sequence of SEQ ID NO: 22.

19. The method of claim 1, wherein the third amplification oligomer comprises the sequence of SEQ ID NO: 41.

20. The method of claim 1, further comprising contacting the sample or composition with a probe oligomer, wherein the probe oligomer comprises a non-nucleotide detectable label, a first self-complementary region at its 5' end, and a second self-complementary region at its 3' end.

* * * * *

UNITED STATES PATENT AND TRADEMARK OFFICE
CERTIFICATE OF CORRECTION

PATENT NO. : 11,220,719 B2
APPLICATION NO. : 16/672224
DATED : January 11, 2022
INVENTOR(S) : Gao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 36 days.

Signed and Sealed this
Twenty-ninth Day of November, 2022

Katherine Kelly Vidal
*Director of the United States Patent and Trademark Office*

SEQUENCE LISTING

<160> NUMBER OF SEQ ID NOS: 191

<210> SEQ ID NO 1
<211> LENGTH: 3221
<212> TYPE: DNA
<213> ORGANISM: Hepatitis B virus
<300> PUBLICATION INFORMATION:
<308> DATABASE ACCESSION NUMBER: AB116092
<309> DATABASE ENTRY DATE: 2006-10-05
<313> RELEVANT RESIDUES IN SEQ ID NO: (1)..(3221)

<400> SEQUENCE: 1
ttccacagct ttccaccaag ctctgcaaga tcccagagtc aggggcctgt attttcctgc    60
tggtggctcc agttcaggaa cactcaaccc tgttccaact attgcctctc acatctcgtc   120
aatctcctcg aggattgggg accctgcacc gaacatggag aacatcacat caggattcct   180
aggacccctg ctcgtgttac aggcggggtt tttcttgttg acaagaatcc tcacaatacc   240
gcagagtcta gactcgtggt ggacttctct caattttcta ggggagcac ccgtgtgtct   300 tggccaaaat tcgcagtccc caacctccaa tcactcacca acctcctgtc tccaatttg   360 tcctggttat cgctggatgt gtctgcggcg ttttatcata ttcctcttca tcctgctgct   420

```
atgcctcatc ttcttattgg ttcttctgga ttatcaaggt atgttgcccg tttgtcctct      480
aattccagga tcaacaacaa ccagcacggg accctgcaaa acctgcacga ctcctgctca      540
agggaactct atgtttccct catgttgctg tacaaaacct acggatggaa attgcacctg      600
tattcccatc ccatcatctt ggggtttcgc aaaattccta tgggagtggg cctcagtccg      660
tttctcttgt ctcagtttac tagtgccatt tgttcagtgg ttcgtagggc tttcccccac      720
tgtttggctt ttagctatat ggatgatgtg gtactggggg ccaagtctgt acaacatctt      780
gagtcccttt acaccgctgt taccaatttt cttttgtctt tgggtataca tttaaaccct      840
aacaaaacaa agagatgggg ttattccctg aatttcatgg gttatgtaat tggaagttgg      900
ggtacattgc cacaggatca tattgtacaa aaatcaaac actgttttag aaaacttcct       960
gtaaatcgac ctattgattg gaaagtatgt cagagaattg tgggtctttt gggctttgca     1020
gctccattta cacaatgtgg ttaccctgca ttaatgcctt tgtatgcatg tatacaggcg     1080
aaacaggctt ttactttctc gccaacttac aaggcctttc taagtaaaca gtatatgaac     1140
ctttaccccg ttgcccggca acggcctggt ctgtgccaag tgtttgctga cgcaaccccc     1200
actggctggg gcttggccat cggccatcag cgcatgcgtg gaacctttgt ggctcctctg     1260
ccgatccata ctgcggaact cctagccgct tgttttgctc gcagcaggtc tggagcaaaa     1320
ctcatcggaa ctgataattc tgtcgtcctt tctcggaagt atacatcctt tccatggctg     1380
ctaggttgta ctgccaactg gattcttcgc gggacgtcct ttgtctacgt cccgtcggcg     1440
ctgaatcccg cggacgaccc ttcgcgaggc cgcttgggc tgtatcgtcc ccttctccgt      1500
ctgccgtacc gtccgaccac ggggcgcacc tctctttacg cggtctcccc gtctgtgcct     1560
tctcatctgc cggtccgtgt gcacttcgct tcacctctgc acgttgcatg gagaccaccg     1620
tgaacgccca tcaggtcctg cccaaggtct tatataagag gactcttgga ctctcagcaa     1680
tgtcaacgac cgaccttgag gcctacttca aagactgtgt gtttaaagac tgggaggagt     1740
tgggggagga gattaggtta atgatctttg tattaggagg ctgtaggcat aaattggtct     1800
gcgcaccatc atcatgcaac ttttcacct ctgcctaatc atctcttgta catgtcccac      1860
ttttcaagcc tccaagctgt gccttggatg gctttgggc atggacattg acccttataa      1920
agaatttgga gctactgtgg agttacttc atttttgcct tctgacttct ttccttccgt      1980
ccgggatcta ctagatacag tcgcagctct atttcgggat gccttagagt ctcctgagca     2040
ttgctcagct caccacacag cactaaggca agtcattctc tgctgggggg aattaatgac     2100
tctagctacc tgggtgggta ctaatttgca agatccagca tccagggatc tagtagtcag     2160
ttatgttaat gataacatgg gcctaaagat caggcaatta ttatggtttc atacttcttg     2220
cattactttg ggaagagaaa ctgtccttga gtatttggtc tctttcggag tgtggattcg     2280
cactcctcca gcctatagac caccaaatgc ccctatctta tcaacacttc cggaaactac     2340
tgttgttaga cgacgagacc gaggcaggtc ccctagaaga agaactccct cgcctcgcag     2400
acgaagatct caatcgccgc gtcgcagaag atctcaatct cgggaacctc aatgttagta     2460
ttccttggac tcataaggtg ggaaatttta ctggacttta ttcttctact gtccctatct     2520
ttaatcctga atggcaaaca ccgtcttttc ctaaaattca tttacatgaa gacattgcta     2580
ataggtgtca gcaatttgta ggccctctca ctgtaaatga aaaagaaga ctgaaattaa      2640 ttatgcctgc taggttttat cctaacagca caaaatattt gccttagac aaagggatta      2700 aaacttatta tcctgatcag gtagttaatc attactttca aacccgacat tatttacata     2760
```

```
ctctttggaa ggctgggatt ctatataaga gggaaactac acgtagcgcc tcatattgcg    2820
ggtcaccata ttcttgggaa caagagctac atcatgggag gttggtcatc aaaacctcgc    2880
aaaggcatgg ggacgaacct ttctgttccc aacccgctgg gattctttcc cgatcatcag    2940
ttggaccctg cattcggagc caatgcaaac aatccagatt gggacctcaa ccccatcaag    3000
gaccactggc cacaagccaa ccaggtagga gtgggagcat ttggaccagg gctcactccc    3060
ccacacggag gtgttttggg gtggagccct caggctcaag gcatattggc caccgtgcca    3120
acagtgcctc ctcctgcctc caccaatcgg cagtcgggaa ggcagcctac tcccatttct    3180
ccacctctaa gagacagtca tcctcaggcc atgcagtgga a                        3221
```

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 2

```
ggcacctagt ccagaagaac caa                                               23
```

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 3

```
ggcacctagt ccagaagaac c                                                 21
```

<210> SEQ ID NO 4
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 4

```
cagaagaacc                                                              10
```

<210> SEQ ID NO 5
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 5

```
tagtccagaa                                                              10
```

<210> SEQ ID NO 6
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 6

```
gcacctagtc                                                              10
```

<210> SEQ ID NO 7
<211> LENGTH: 10

```
<212> TYPE: DNA
<213> ORGANISM: Artificial Sequence
<220> FEATURE:
<223> OTHER INFORMATION: Synthetic Oligomer

<400> SEQUENCE: 7
gaagaaccaa                                                          10

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 8
taatacgact cactatag                                                 18

<210> SEQ ID NO 9
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 9
taatacgact cactataggg aga                                           23

<210> SEQ ID NO 10
<211> LENGTH: 31
<212> TYPE: DNA
<213> ORGANISM: Artificial Sequence
<220> FEATURE:
<223> OTHER INFORMATION: Synthetic Oligomer

<400> SEQUENCE: 10
taatacgact cactataggg agaccacaac g                                  31

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 11
aatttaatac gactcactat ag                                            22

<210> SEQ ID NO 12
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 12
aatttaatac gactcactat agggaga                                       27

<210> SEQ ID NO 13
<211> LENGTH: 35
<212> TYPE: DNA
<213> ORGANISM: Artificial Sequence
<220> FEATURE:
<223> OTHER INFORMATION: Synthetic Oligomer

<400> SEQUENCE: 13
```

```
aatttaatac gactcactat agggagacca caacg                                      35

<210> SEQ ID NO 14
<211> LENGTH: 49
<212> TYPE: DNA
<213> ORGANISM: Artificial Sequence
<220> FEATURE:
<223> OTHER INFORMATION: Synthetic Oligomer

<400> SEQUENCE: 14
aatttaatac gactcactat agggagagat gtgtctgcgg cgttttatc                       49

<210> SEQ ID NO 15
<211> LENGTH: 54
<212> TYPE: DNA
<213> ORGANISM: Artificial Sequence
<220> FEATURE:
<223> OTHER INFORMATION: Synthetic Oligomer

<400> SEQUENCE: 15
aatttaatac gactcactat agggagagat gtgtctgcgg cgttttatca tctt                 54

<210> SEQ ID NO 16
<211> LENGTH: 57
<212> TYPE: DNA
<213> ORGANISM: Artificial Sequence
<220> FEATURE:
<223> OTHER INFORMATION: Synthetic Oligomer

<400> SEQUENCE: 16
aatttaatac gactcactat agggagagat gtgtctgcgg cgttttatca tcttcct              57

<210> SEQ ID NO 17
<211> LENGTH: 35
<212> TYPE: DNA
<213> ORGANISM: Artificial Sequence
<220> FEATURE:
<223> OTHER INFORMATION: Synthetic Oligomer

<400> SEQUENCE: 17
ggagagatgt gtctgcggcg ttttatcatc ttcct                                      35

<210> SEQ ID NO 18
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 18
ggagagatgt gtctgcggcg ttttatc                                               27

<210> SEQ ID NO 19
<211> LENGTH: 32
<212> TYPE: DNA
<213> ORGANISM: Artificial Sequence
<220> FEATURE:
<223> OTHER INFORMATION: Synthetic Oligomer

<400> SEQUENCE: 19
ggagagatgt gtctgcggcg ttttatcatc tt                                         32

<210> SEQ ID NO 20
<211> LENGTH: 30
<212> TYPE: DNA
<213> ORGANISM: Artificial Sequence
```

```
<220> FEATURE:
<223> OTHER INFORMATION: Synthetic Oligomer

<400> SEQUENCE: 20
gatgtgtctg cggcgtttta tcatcttcct                                30

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 21
gatgtgtctg cggcgtttta tc                                        22

<210> SEQ ID NO 22
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 22
gatgtgtctg cggcgtttta tcatctt                                   27

<210> SEQ ID NO 23
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 23
gcgttttatc                                                      10

<210> SEQ ID NO 24
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 24
ctgcggcgtt                                                      10

<210> SEQ ID NO 25
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 25
tgtgtctgcg                                                      10

<210> SEQ ID NO 26
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 26
ttatcatctt                                                      10
```

```
<210> SEQ ID NO 27
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 27
tcatcttcct                                                              10

<210> SEQ ID NO 28
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 28
ggagagatgt                                                              10

<210> SEQ ID NO 29
<211> LENGTH: 38
<212> TYPE: RNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (33)..(34)
<223> OTHER INFORMATION: Non-nucleotide c9 linker inserted between base
      positions 33-34

<400> SEQUENCE: 29
cccacaagaa gaugaggcau agcagcagga ugaguggg                               38

<210> SEQ ID NO 30
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 30
aatttaatac gactcactat agggagacca caacggtggg cctcagtccg tttctc           56

<210> SEQ ID NO 31
<211> LENGTH: 62
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (57)..(57)
<223> OTHER INFORMATION: n = Inosine

<400> SEQUENCE: 31
aatttaatac gactcactat agggagacca caacggtggg cctcagtccg tttctcntgg       60
ct                                                                      62

<210> SEQ ID NO 32
<211> LENGTH: 34
<212> TYPE: DNA
<213> ORGANISM: Artificial Sequence
<220> FEATURE:
<223> OTHER INFORMATION: Synthetic Oligomer
```

<400> SEQUENCE: 32
ggagaccaca acggtgggcc tcagtccgtt tctc                          34

<210> SEQ ID NO 33
<211> LENGTH: 40
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (35)..(35)
<223> OTHER INFORMATION: n = Inosine

<400> SEQUENCE: 33
ggagaccaca acggtgggcc tcagtccgtt tctcntggct                    40

<210> SEQ ID NO 34
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 34
ccacaacggt gggcctcagt ccgtttctc                                29

<210> SEQ ID NO 35
<211> LENGTH: 35
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (30)..(30)
<223> OTHER INFORMATION: n = Inosine

<400> SEQUENCE: 35
ccacaacggt gggcctcagt ccgtttctcn tggct                         35

<210> SEQ ID NO 36
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 36
tccgtttctc                                                     10

<210> SEQ ID NO 37
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 37
ctcagtccgt                                                     10

<210> SEQ ID NO 38
<211> LENGTH: 10
<212> TYPE: DNA
<213> ORGANISM: Artificial Sequence
<220> FEATURE:
<223> OTHER INFORMATION: Synthetic Oligomer

```
<400> SEQUENCE: 38
tgggcctcag                                                          10

<210> SEQ ID NO 39
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (5)..(5)
<223> OTHER INFORMATION: n = Inosine

<400> SEQUENCE: 39 tctcntggct                                                          10

<210> SEQ ID NO 40
<211> LENGTH: 26
<212> TYPE: RNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (21)..(22)
<223> OTHER INFORMATION: Non-nucleotide c9 linker inserted between base
      positions 21-22

<400> SEQUENCE: 40
ugcgcuagua aacugagcca ggcgca                                        26

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 41
cctgcgaacc actgaacaaa                                               20

<210> SEQ ID NO 42
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 42
cactgaacaa a                                                        11

<210> SEQ ID NO 43
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 43
gaaccactga                                                          10

<210> SEQ ID NO 44
<211> LENGTH: 10
<212> TYPE: DNA
<213> ORGANISM: Artificial Sequence
```

```
<220> FEATURE:
<223> OTHER INFORMATION: Synthetic Oligomer

<400> SEQUENCE: 44
cctgcgaacc                                                          10

<210> SEQ ID NO 45
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (26)..(58)
<223> OTHER INFORMATION: Immobilized probe-binding region: Tail

<400> SEQUENCE: 45
gggctttccc ccactgtttg gctttttaa aaaaaaaaa aaaaaaaaaa aaaaaaa        58

<210> SEQ ID NO 46
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (26)..(58)
<223> OTHER INFORMATION: Immobilized probe-binding region: Tail

<400> SEQUENCE: 46
agttatatgg atgatgtggt attggtttaa aaaaaaaaa aaaaaaaaaa aaaaaaa        58

<210> SEQ ID NO 47
<211> LENGTH: 59
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (27)..(59)
<223> OTHER INFORMATION: Immobilized probe-binding region: Tail

<400> SEQUENCE: 47
ggtctgtgcc aagtgtttgc tgacgcttta aaaaaaaaa aaaaaaaaaa aaaaaaaa       59

<210> SEQ ID NO 48
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (29)..(58)
<223> OTHER INFORMATION: Immobilized probe-binding region: Tail

<400> SEQUENCE: 48
ttgttttgct cgcagccggt ctggagcgaa aaaaaaaaa aaaaaaaaaa aaaaaaa        58

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligomer
```

```
<400> SEQUENCE: 49
gggctttccc ccactgtttg gc                                              22

<210> SEQ ID NO 50
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 50
actgtttggc                                                            10

<210> SEQ ID NO 51
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 51
cccccactgt                                                            10

<210> SEQ ID NO 52
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 52
gggctttccc                                                            10

<210> SEQ ID NO 53
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 53
agttatatgg atgatgtggt attgg                                           25

<210> SEQ ID NO 54
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 54
gtggtattgg                                                            10

<210> SEQ ID NO 55
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 55
atgatgtggt                                                            10

<210> SEQ ID NO 56
<211> LENGTH: 10
```

```
<212> TYPE: DNA
<213> ORGANISM: Artificial Sequence
<220> FEATURE:
<223> OTHER INFORMATION: Synthetic Oligomer

<400> SEQUENCE: 56
tatggatgat                                                              10

<210> SEQ ID NO 57
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 57
ggtctgtgcc aagtgtttgc tgacgc                                            26

<210> SEQ ID NO 58
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 58
ttgctgacgc                                                              10

<210> SEQ ID NO 59
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 59
agtgtttgct                                                              10

<210> SEQ ID NO 60
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 60
tgccaagtgt                                                              10

<210> SEQ ID NO 61
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 61
ttgttttgct cgcagccggt ctggagcg                                          28

<210> SEQ ID NO 62
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 62
```
gtctggagcg                                                                              10

<210> SEQ ID NO 63
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 63
agccggtctg                                                                              10

<210> SEQ ID NO 64
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 64
ctcgcagccg                                                                              10

<210> SEQ ID NO 65
<211> LENGTH: 33
<212> TYPE: DNA
<213> ORGANISM: Artificial Sequence
<220> FEATURE:
<223> OTHER INFORMATION: Synthetic Oligomer

<400> SEQUENCE: 65
tttaaaaaaa aaaaaaaaaa aaaaaaaaaa aaa                                                    33

<210> SEQ ID NO 66
<211> LENGTH: 30
<212> TYPE: DNA
<213> ORGANISM: Artificial Sequence
<220> FEATURE:
<223> OTHER INFORMATION: Synthetic Oligomer

<400> SEQUENCE: 66
aaaaaaaaaa aaaaaaaaaa aaaaaaaaaa                                                        30

<210> SEQ ID NO 67
<211> LENGTH: 57
<212> TYPE: DNA
<213> ORGANISM: Artificial Sequence
<220> FEATURE:
<223> OTHER INFORMATION: Synthetic Oligomer

<400> SEQUENCE: 67
aatttaatac gactcactat agggagaaga ctcgtggtgg acttctctca attttct                          57

<210> SEQ ID NO 68
<211> LENGTH: 35
<212> TYPE: DNA
<213> ORGANISM: Artificial Sequence
<220> FEATURE:
<223> OTHER INFORMATION: Synthetic Oligomer

<400> SEQUENCE: 68
ggagaagact cgtggtggac ttctctcaat tttct                                                  35

<210> SEQ ID NO 69
<211> LENGTH: 30
<212> TYPE: DNA
<213> ORGANISM: Artificial Sequence

```
<220> FEATURE:
<223> OTHER INFORMATION: Synthetic Oligomer

<400> SEQUENCE: 69
agactcgtgg tggacttctc tcaattttct                                    30

<210> SEQ ID NO 70
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 70
tcaattttct                                                          10

<210> SEQ ID NO 71
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 71
ttctctcaat                                                          10

<210> SEQ ID NO 72
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 72
tggacttctc                                                          10

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 73
tatcaaggta tgttgcccgt                                               20

<210> SEQ ID NO 74
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 74
tgttgcccgt                                                          10

<210> SEQ ID NO 75
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 75
aggtatgttg                                                          10
```

```
<210> SEQ ID NO 76
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 76
tatcaaggta                                                           10

<210> SEQ ID NO 77
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 77
gattatatag gacgacaag                                                 19

<210> SEQ ID NO 78
<211> LENGTH: 49
<212> TYPE: DNA
<213> ORGANISM: Artificial Sequence
<220> FEATURE:
<223> OTHER INFORMATION: Synthetic Oligomer

<400> SEQUENCE: 78
aatttaatac gactcactat agggagagat gattgacttg tgattccgc                49

<210> SEQ ID NO 79
<211> LENGTH: 23
<212> TYPE: RNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (5)..(6)
<223> OTHER INFORMATION: Non-nucleotide c9 linker inserted between base
      positions 5-6

<400> SEQUENCE: 79
gcauggugcg aauugggaca ugc                                            23

<210> SEQ ID NO 80
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (25)..(57)
<223> OTHER INFORMATION: Immobilized probe-binding region: Tail

<400> SEQUENCE: 80
cguucacuau uggucucugc auuctttaaa aaaaaaaaa aaaaaaaaaa aaaaaaa         57

<210> SEQ ID NO 81
<211> LENGTH: 24
<212> TYPE: RNA
<213> ORGANISM: Artificial Sequence
<220> FEATURE:
<223> OTHER INFORMATION: Synthetic oligomer

<400> SEQUENCE: 81
```

```
cguucacuau uggucucugc auuc                                          24
```

<210> SEQ ID NO 82
<211> LENGTH: 28
<212> TYPE: RNA
<213> ORGANISM: Artificial Sequence
<220> FEATURE:
<223> OTHER INFORMATION: Synthetic oligomer

<400> SEQUENCE: 82

```
aagaagauga ggcauagcag caggauga                                      28
```

<210> SEQ ID NO 83
<211> LENGTH: 10
<212> TYPE: RNA
<213> ORGANISM: Artificial Sequence
<220> FEATURE:
<223> OTHER INFORMATION: Synthetic oligomer

<400> SEQUENCE: 83

```
gcuaguaaac                                                          10
```

<210> SEQ ID NO 84
<211> LENGTH: 16
<212> TYPE: RNA
<213> ORGANISM: Artificial Sequence
<220> FEATURE:
<223> OTHER INFORMATION: Synthetic oligomer

<400> SEQUENCE: 84

```
uaguaaacug agccag                                                   16
```

<210> SEQ ID NO 85
<211> LENGTH: 20
<212> TYPE: RNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (18)..(19)
<223> OTHER INFORMATION: Non-nucleotide c9 linker inserted between base
      positions 18-19

<400> SEQUENCE: 85

```
gcuaguaaac ugagccaggc                                               20
```

<210> SEQ ID NO 86
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 86

```
gatgattgac ttgtgattcc gc                                            22
```

<210> SEQ ID NO 87
<211> LENGTH: 59
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (27)..(59)
<223> OTHER INFORMATION: Immobilized probe-binding region: Tail

<400> SEQUENCE: 87
ggtctgtgcc aagtgtttgc tgacgcttta aaaaaaaaaa aaaaaaaaaa aaaaaaaaa    59

<210> SEQ ID NO 88
<211> LENGTH: 60
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (31)..(60)
<223> OTHER INFORMATION: Immobilized probe-binding region: Tail

<400> SEQUENCE: 88
tcctctgccg atccatactg cggaactcct aaaaaaaaaa aaaaaaaaaa aaaaaaaaaa    60

<210> SEQ ID NO 89
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (29)..(58)
<223> OTHER INFORMATION: Immobilized probe-binding region: Tail

<400> SEQUENCE: 89
ttgttttgct cgcagccggt ctggagcgaa aaaaaaaaaa aaaaaaaaaa aaaaaaa      58

<210> SEQ ID NO 90
<211> LENGTH: 56
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (24)..(56)
<223> OTHER INFORMATION: Immobilized probe-binding region: Tail

<400> SEQUENCE: 90
gggctttccc ccactgtttg gcttttaaaa aaaaaaaaaa aaaaaaaaaa aaaaaa        56

<210> SEQ ID NO 91
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (26)..(58)
<223> OTHER INFORMATION: Immobilized probe-binding region: Tail

<400> SEQUENCE: 91
agttatatgg atgatgtggt attggtttaa aaaaaaaaa aaaaaaaaaa aaaaaaaa      58

<210> SEQ ID NO 92
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (26)..(58)
<223> OTHER INFORMATION: Immobilized probe-binding region: Tail -continued

<400> SEQUENCE: 92
ccgctgttac caattttctt ttgtctttaa aaaaaaaaaa aaaaaaaaaa aaaaaaaa            58

<210> SEQ ID NO 93
<211> LENGTH: 59
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (27)..(59)
<223> OTHER INFORMATION: Immobilized probe-binding region: Tail

<400> SEQUENCE: 93
ggucugugcc aaguguuugc ugacgcttta aaaaaaaaaa aaaaaaaaaa aaaaaaaaa           59

<210> SEQ ID NO 94
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (26)..(58)
<223> OTHER INFORMATION: Immobilized probe-binding region: Tail

<400> SEQUENCE: 94
gucugugcca aguguuugcu gacgctttaa aaaaaaaaaa aaaaaaaaaa aaaaaaaa            58

<210> SEQ ID NO 95
<211> LENGTH: 58
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (26)..(58)
<223> OTHER INFORMATION: Immobilized probe-binding region: Tail

<400> SEQUENCE: 95
aguuauaugg augauguggu auuggtttaa aaaaaaaaaa aaaaaaaaaa aaaaaaaa            58

<210> SEQ ID NO 96
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 96
ggtctgtgcc aagtgtttgc tgacgc                                              26

<210> SEQ ID NO 97
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 97
tcctctgccg atccatactg cggaactcc                                           29

<210> SEQ ID NO 98

```
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 98
ttgttttgct cgcagccggt ctggagcg                                      28

<210> SEQ ID NO 99
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 99
gggctttccc ccactgtttg gctttt                                        26

<210> SEQ ID NO 100
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 100
agttatatgg atgatgtggt attgg                                         25

<210> SEQ ID NO 101
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 101
ccgctgttac caattttctt ttgtc                                         25

<210> SEQ ID NO 102
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 102
ggucugugcc aaguguuugc ugacgc                                        26

<210> SEQ ID NO 103
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 103
gucugugcca aguguuugcu gacgc                                         25

<210> SEQ ID NO 104
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 104
```

```
aguuauaugg augauguggu auugg                                            25
```

<210> SEQ ID NO 105
<211> LENGTH: 960
<212> TYPE: DNA
<213> ORGANISM: Hepatitis B virus
<300> PUBLICATION INFORMATION:
<308> DATABASE ACCESSION NUMBER: AY707087
<309> DATABASE ENTRY DATE: 2007-10-23
<313> RELEVANT RESIDUES IN SEQ ID NO: (1)..(900)

<400> SEQUENCE: 105

```
aattccactg ccttccacca agctctgcag gatcccaaag tcaggggtct gtattttcct      60
gctggtggct ccagttcagg aacagtaaac cctgctccga atattgcctc tcacatctcg     120
tcaatctccg cgaggactgg ggaccctgtg acgaatatgg agaacatcac atcaggattc     180
ctaggacccc tgctcgtgtt acaggcgggg ttttttcttgt tgacaagaat cctcacaata    240
ccgcagagtc tagactcgtg gtggacttct ctcaattttc taggggggatc acccgtgtgt    300 cttggccaaa attcgcagtc cccaacctcc aatcactcac caacctcctg tcctccaatt    360
tgtcctggtt atcgctggat gtgtctgcgg cgttttatca tattcctctt catcctgctg    420
ctatgcctca tcttcttgtt ggttcttctg gattatcaag gtatgttgcc cgtttgtcct    480
ctaattccag gaacaacaac aaccagtacg ggaccatgca aaacctgcac gactcctgct    540
caaggcaact ctatgtttcc ctcatgttgc tgtacaaaac cttcggatgg aaattgcacc    600
tgtattccca tcccatcgtc ttgggctttc gcaaaatacc tatgggagtg ggcctcagtc    660
cgtttctctt ggctcagttt actagtgcca tttgttcagt ggttcgtagg gctttccccc    720
actgtttggc tttcagctat atggatgatg tggtattggg ggccaagtct gtacagcatc    780
gtgagtccct ttataccgct gttaccaatt ttcttttgtc tctgggtata catttaaacc    840
ctaacaaaac aaaagatgg ggttattccc taaacttcat gggttacata attggaagtt     900
ggggaacgtt gccacaggat catattgtac aaaagatcaa acactgtttt agaaaacttc    960
```

<210> SEQ ID NO 106
<211> LENGTH: 900
<212> TYPE: DNA
<213> ORGANISM: Hepatitis B virus
<300> PUBLICATION INFORMATION:
<308> DATABASE ACCESSION NUMBER: AB194951
<309> DATABASE ENTRY DATE: 2007-11-17
<313> RELEVANT RESIDUES IN SEQ ID NO: (1)..(900)

<400> SEQUENCE: 106

```
ttccacaaat ttccaccaag ctctgcaaga tcccagagtc aggggcctgt atcttcctgc      60
tggtggctcc agttcaggaa cagtcaaccc tgctccgaat attgcctctc acatctcgtc    120
aatctcctcg aggattgggg accctgcgcc gaacatggag aacatcacat caggattcct    180 aggaccctg ctcgtgttac aggcgggtt tttctcgttg acaaaaatcc tcacaatacc     240
gcagagtcta gactcgtggt ggacttctct caattttcta ggggagcac ccgtgtgtct    300 tggccaaaat tcgcagtccc caacctccaa tcactcacca acctcctgtc tccaatttg    360 tcctggttat cgctggatgt gtctgcggcg ttttatcata ttcctcttca tcctgctgct    420
atgcctcatc ttcttattgg ttcttctgga ttgtcaaggt atgttgcccg tttgtcctct    480
aattccagga tccacaacca ccagtacggg accctgcaga acctgcacga ctcctgctca    540
aggcaactct atgtttccct catgttgctg tacaaaacct acggacggaa attgcacctg    600
```

| | |
|---|---|
| tattcccatc ccatcatcct gggctttcgc aaaataccta tggggtgggg cctcagtccg | 660 |
| tttctcctgg ctcagtttac tagtgccatt tgttcagtgg ttcgtagggc tttcccccat | 720 |
| tgtttggctt tcagctatat ggatgatgtg gtattggggg ccaagtctgt acaacatctt | 780 |
| gagtcccttt ataccgctgt taccaatttt cttttggctt tgggcataca tttaaaccct | 840 |
| aacaaaacaa aaagatgggg ttattccctt aacttcatgg gatacataat tggaagttgg | 900 |

```
<210> SEQ ID NO 107
<211> LENGTH: 900
<212> TYPE: DNA
<213> ORGANISM: Hepatitis B virus
<300> PUBLICATION INFORMATION:
<308> DATABASE ACCESSION NUMBER: AB014366
<309> DATABASE ENTRY DATE: 2006-11-02
<313> RELEVANT RESIDUES IN SEQ ID NO: (1)..(900)

<400> SEQUENCE: 107
```

| | |
|---|---|
| ttccaccact ttccaccaaa ctcttcaaga tcccagagtc agggctctgt accttcctgc | 60 |
| tggtggctcc agttcaggaa tagtaagccc tgctcagaat actgtctctg ccatatcgtc | 120 |
| aatcttatcg acgactgggg accctgtgcc gaacatggag aacatcgcat caggactcct | 180 |
| aggacccctg ctcgtgttac aggcggggtt tttctcgttg acaaaaatcc tcacaatacc | 240 |
| acagagtcta gactcgtggt ggacttctct cagttttcta ggggaacac ccgtgtgtct | 300 |
| tggccaaaat tcgcagtccc aaatctccag tcactcacca acctgttgtc tccaatttg | 360 |
| tcctggttat cgctggatgt atctgcggcg ttttatcatc tgcctctgca tcctgctgct | 420 |
| atgcctcatc ttcttgttgg ttcttctgga ctatcaaggt atgttgcccg tttgtcctct | 480 |
| aattccagga tcatcaacca ccagcacggg accatgcaag acctgcacaa ctcctgctca | 540 |
| aggaacctct atgtttccct catgttgctg tacaaaacct acggacggaa actgcacctg | 600 |
| tattcccatc ccatcatctt gggctttcgc aaaattccta tgggagtggg cctcagtccg | 660 |
| tttctcttgg ctcagtttac tagtgccatt tgttcagtgg ttcgtagggc tttcccccac | 720 |
| tgtctggctt tcagttatat ggatgatgtg gtattggggg ccaagtctgt acaacatctt | 780 |
| gagtcccttt atgccgctgt taccaatttt cttttgtctt gggtataca tttaaaccct | 840 |
| cacaaaacaa aaagatgggg atattccctt aatttcatgg gatatgtaat tgggagttgg | 900 |

```
<210> SEQ ID NO 108
<211> LENGTH: 900
<212> TYPE: DNA
<213> ORGANISM: Hepatitis B virus
<300> PUBLICATION INFORMATION:
<308> DATABASE ACCESSION NUMBER: AY596111
<309> DATABASE ENTRY DATE: 2004-08-24
<313> RELEVANT RESIDUES IN SEQ ID NO: (1)..(900)

<400> SEQUENCE: 108
```

| | |
|---|---|
| ctccaccact ttccaccaaa ctcttcaaga tcccagagtc agggccctgt actttcctgc | 60 |
| tggtggctcc agttcaggaa cagtgagccc tgctcagaat actgtctctg ccatatcgtc | 120 |
| aatcttatcg aagactgggg accctgtacc gaacatggag aacatcgcat caggactcct | 180 |
| aggacccctg ctcgtgttac aggcggggtt tttctcgttg acaaaaatcc tcacaatacc | 240 |
| acagagtcta gactcgtggt ggacttctct cagttttcta ggggaacac ccgtgtgtct | 300 |
| tggccaaaat tcgcagtccc aaatctccag tcactcacca acctgttgtc tccaatttg | 360 |
| tcctggttat cgctggatgt gtctgcggcg ttttatcatc ttcctctgca tcctgctgct | 420 |
| atgcctcatc ttcttgttgg ttcttctgga ctatcaaggt atgttgcccg tttgtcctct | 480 |

-continued

```
aattccagga tcatcaacaa ccagcaccgg accatgcaaa acctgcacaa cttctgctca    540
aggaacctct atgtttccct catgttgctg tacaaaacct acggacgaaa actgcacctg    600
tattcccatc ccatcatctt gggctttcgc aaaatacctg tgggagtggg cctcagtccg    660
tttctcttgg ctcagtttac tagtgccatt tgttcagtgg ttcgtagggc tttcccccac    720
tgtctggctt tcagttatat ggatgatgtg gttttggggg ccaagactgt acagcatctt    780
gagtcccttt atgccgctgt taccaatttt cttttgtctt tgggcataca tttaaaccct    840
cacaaaacaa aaagatgggg atattccctt aacttcatgg gatatgtaat tgggagttgg    900
```

<210> SEQ ID NO 109
<211> LENGTH: 900
<212> TYPE: DNA
<213> ORGANISM: Hepatitis B virus
<300> PUBLICATION INFORMATION:
<308> DATABASE ACCESSION NUMBER: M54923
<309> DATABASE ENTRY DATE: 2000-06-13
<313> RELEVANT RESIDUES IN SEQ ID NO: (1)..(900)

<400> SEQUENCE: 109

```
ctccaccacg ttccaccaaa ctcttcaaga tcccagagtc agggctctgt actttcctgc     60
tggtggctcc agttcaggaa cagtaaaccc tgttcagaac actgtctctt ccatatcgtc    120
aatcttatcg aagactgggg accctgtgcc gaacatggag aacatcgcat caggactcct    180 aggaccctg ctcgtgttac aggcggggtt tttcttgttg acaaaaatcc tcacaatacc    240
acagagtcta gactcgtggt ggacttctct caatttttcta gggggaacac ccgtgtgtct    300
tggccaaaat tcgcagtccc aaatctccag tcactcacca acttgttgtc ctccgatttg    360
tcctggttat cgctggatgt gtctgcggcg ttttatcatc ttcctctgca tcctgctgct    420
atgcctcatc ttcttgttgg ttcttctgga ctatcaaggt atgttgcccg tttgtcctct    480
aattccagga tcatcaacca ccagcaccgg accatgcaaa acctgcacga ctcctgctca    540
aggaacctct atgtttccct catgttgctg tacaaaacct acggacggaa actgcacctg    600
tattcccatc ccatcatctt gggctttcgc aaaatacctg tgggagtggg cctcagtccg    660
tttctcttgg ctcagtttac tagtgccatt tgttcagtgg ttcgtagggc tttcccccac    720
tgtctggctt tcagttatat ggatgatgtg gttttggggg ccaagtctgt acaacatctt    780
gagtcccttt atgccgctgt taccaatttt cttttgtctt tgggtataca tttaaaccct    840
cagaaaacaa aaagatgggg ctactccctc aacttcatgg ggtatgtaat tggaagttgg    900
```

<210> SEQ ID NO 110
<211> LENGTH: 900
<212> TYPE: DNA
<213> ORGANISM: Hepatitis B virus
<300> PUBLICATION INFORMATION:
<308> DATABASE ACCESSION NUMBER: AB073835
<309> DATABASE ENTRY DATE: 2002-06-04
<313> RELEVANT RESIDUES IN SEQ ID NO: (1)..(900)

<400> SEQUENCE: 110

```
ctccaccact ttccatcaaa ctcttcaaga tcccagagtc agggctctgt actttcctgc     60
tggtggctcc agttcaggaa tagtaaaccc tgctcagaat actgcctctg ccatatcatc    120
aaccttctcg aagactgggg accctgtacc gaacatggag aacatcgcat caggactcct    180 aggaccctg ctcgtgttac aggcggggtt tttcttgttg acaaaaatcc tcacaatacc    240
acagagtcta gactcgtggt ggacttctct caatttttcta gggggaacac ccgtgtgtct    300
```

```
tggccaaaat tcgcagtccc aaatctccag tcactcacca acttgttgtc ctccaacttg    360
tcctggttat cgctggatgt atctgcggcg tttatcata ttcctctgca tcctgctgct    420
atgcctcatc ttcttgttgg ttcttctgga ctatcaaggt atgttgcccg tttgtcctct    480
aattccagga tcatcaacca ccagcaccgg accctgcaga acctgcacga ctcctgctca    540
aggaacctct atgtttccct catgttgctg tacaaaacct acggacggaa actgcacctg    600
tattcccatc ccatcatctt gggctttcgc aaaattccta tgggagtggg cctcagtccg    660
tttctcttgg ctcagtttac tagtgccgtt tgttcagtgg ttcgtagggc tttcccccac    720
tgtctggctt tcagttatat ggatgatgtg gtattggggg ccaaatctgt acaacatctt    780
gagtcccttt atgccgctgt taccaatttt cttttgtctt tgggtataca tttaaaccct    840
cacaaaacaa aaagatgggg atattccctt aatttcatgg gatatgtaat tggtagttgg    900
```

<210> SEQ ID NO 111
<211> LENGTH: 900
<212> TYPE: DNA
<213> ORGANISM: Hepatitis B virus
<300> PUBLICATION INFORMATION:
<308> DATABASE ACCESSION NUMBER: AY123424
<309> DATABASE ENTRY DATE: 2002-08-16
<313> RELEVANT RESIDUES IN SEQ ID NO: (1)..(900)

<400> SEQUENCE: 111

```
aactccacaa cattccacca agctctgcta gaccccagag tgaggggcct atactttcct     60
gctggtggct ccagttccgg aacagtaaac cctgttccga ctactgcctc acccatatcg    120
tcaatcttct cgaggactgg ggaccctgca ccgaacatgg agcacaac atcaggattc     180 ctaggacccc tgctcgtgtt acaggcgggg ttttcttgt tgacaagaat cctcacaata    240
ccacagagtc tagactcgtg gtggacttct ctcaattttc taggggagc acccacgtgt    300 cttggccaaa attcgcagtc cccaacctcc aatcactcac caacctcttg tcctccaatt    360
tgtcctggtt atcgttggat gtgtctgcgg cgttttatca tattcctctt catcctgctg    420
ctatgcctca tcttcttgtt ggttcttctg gactaccaag gtatgttgcc cgtttgtcct    480
ctacttccaa gaacatcaac taccagcacg ggaccatgca agacctgcac gattcctgct    540
caaggaacct ctatgtttcc ctcttgttgc tgtacaaaac cttcggacgg aaactgcact    600
tgtattccca tccatcatc ttgggctttc gcaagattcc tatgggagtg ggcctcagtc    660
cgtttctcct ggctcagttt actagtgcca tttgttcagt ggttcgtagg gctttcccccc    720 actgtttggc tttcagttat atggatgatg tggtattggg ggccaagtct gtacaacatc    780
ttgagtccct ttttacctct attaccaatt ttcttttgtc tttgggtata catttgaacc    840
ccaataaaac caaacgttgg ggctattccc ttaatttcat gggatatgta attggatgtt    900
```

<210> SEQ ID NO 112
<211> LENGTH: 900
<212> TYPE: DNA
<213> ORGANISM: Hepatitis B virus
<300> PUBLICATION INFORMATION:
<308> DATABASE ACCESSION NUMBER: AF223955
<309> DATABASE ENTRY DATE: 2001-09-07
<313> RELEVANT RESIDUES IN SEQ ID NO: (1)..(900)

<400> SEQUENCE: 112

```
ctccagcaca ttccaccaag ctctgctaga tcccagagtg aggggcctat actttcctgc     60
tggtggctcc agttccggaa cagtaaaccc tgttccgact actgcctctc ccatatcgtc    120
aatcttctcg aggactgggg accctgcacc gaatatggag agcaccacat caggattcct    180
```

```
aggaccnctg ctcgtgttac aggcggggtt tttcttgttg acaagaatcc tcacaatacc      240
acagagtcta gactcgtggt ggacttctct caattttcta gggggagcac ccacgtgtcc      300
tggccaaaat ttgcagtccc caacctccaa tcactcacca acctcttgtc ctccaatttg      360
tcctggttat cgctggatgt gtctgcggcg ttttatcatc ttcctcttca tcctgctgct      420
atgcctcatc ttcttgttgg ttcttctgga ctaccaaggt atgttgcccg tttgtcctct      480
acttccagga acatcaacta ccagcacggg accatgcagg acctgcacga ttcctgctca      540
aggaacctct atgtttccct cttgttgctg tacaaaacct tcggacggaa attgcacttg      600
tattcccatc ccatcatctt gggctttcgc aagattccta tgggagtggg cctcagtccg      660
tttctcctgg ctcagtttac tagtgccatt tgttcagtgg ttcgtagggc tttcccccac      720
tgtttggctt tcagttatat ggatgatgtg gtattggggg ccaagtctgt acaacatctt      780
gaatcccttt ttaccgctat taccaatttt cttttgtctt tgggtataca tttaaaccct      840
aataaaacca aacgttgggg ctactcccct aactttatgg gatatgtcat tggaagttgg      900
```

<210> SEQ ID NO 113
<211> LENGTH: 900
<212> TYPE: DNA
<213> ORGANISM: Hepatitis B virus
<300> PUBLICATION INFORMATION:
<308> DATABASE ACCESSION NUMBER: X75665
<309> DATABASE ENTRY DATE: 2006-11-14
<313> RELEVANT RESIDUES IN SEQ ID NO: (1)..(900)

<400> SEQUENCE: 113

```
ctccacaaca ttccaacaag ctctgcagga tcccagagtc agggtccttt attttcctgc       60
tggtggctcc agttccggaa cagtaaaccc tgttccgact actgcctctc tcatttcgtc      120
aatcttctcg aggattgggg accctgtaac gaacatggag aacacaacat caggattcct      180
aggaccnctg ctcgtgttac aggcggggtt tttcttgttg acaaaaatcc tcacaatacc      240
acagagtcta gactcgtggt ggacttctct caattttcta gggggagcac ccgtgtgtcc      300
tggccaaaat tcgcagtccc caacctccaa tcactcacca acctcttgtc ctccaatttg      360
tcctggctat cgctggatgt gtctgcggcg ttttatcatc ttcctcttca tcctgctgct      420
atgcctcatc ttcttgttgg ttcttctgga ctaccaaggt atgttgcccg tttgtcctct      480
acttccagga acatcaacta ccagcacggg accatgcaag acctgcacga ttcctgctca      540
aggaacctct atgtttccct catgttgctg tacaaaacct tcggacggaa actgcacttg      600
tattcccatc ccatcatcct gggctttcgt aagattccta tgggagtggg cctcagtccg      660
tttctcctgg ctcagtttac tagcgccatt tgttcagtgg ttcgtagggc tttcccccac      720
tgtttggctt tcagttatat ggatgatgtg gtattggggg ccaagtctgt acaacatctt      780
gagtcccttt atacctctat taccaatttt cttttgtctt tgggtataca tttaaaccct      840
aataaaacca aaagatgggg ctattcccct aacttcatgg gctatgtaat tggaagttgg      900
```

<210> SEQ ID NO 114
<211> LENGTH: 900
<212> TYPE: DNA
<213> ORGANISM: Hepatitis B virus
<300> PUBLICATION INFORMATION:
<308> DATABASE ACCESSION NUMBER: AB104712
<309> DATABASE ENTRY DATE: 2003-06-26
<313> RELEVANT RESIDUES IN SEQ ID NO: (1)..(900)

<400> SEQUENCE: 114

```
aactccacta ccttccacca aactctgcaa gatcccagag tgagaggcct gtatttccct    60
gctggtggct ccagttcagg aacagtaaac cctgttccga ctactgtctc tcacatatcg   120
tcaatcttct cgaggattgg ggaccctgcg ctgaacatgg agaacatcac atcaggattc   180
ctaggacccc tgctcgtgtt acaggcgggg ttttcttgt tgacaagaat cctcacaata    240
ccgcagagtc tagactcgtg gtggacttct ctcaattttc taggggaac taccgtgtgt    300 cttggccaaa attcgcagtc cccaacctcc aatcactcac caacctcctg tcctccaact   360
tgtcctggtt atcgctggat gtgtctgcgg cgttttatca tcttcctctt catcctgctg   420
ctatgcctca tcttcttgtt ggttcttctg gactatcaag gtatgttgcc cgtttgtcct   480
ctaattccag gatcttcaac taccagcacg ggaccatgca gaacctgcac gactcctgct   540
caaggaacct ctatgtatcc ctcctgctgc tgtaccaaac cttcggacgg aaattgcacc   600
tgtattccca tcccatcatc ctgggctttc ggaaaattcc tatgggagtg gcctcagcc    660 cgtttctcct ggctcagttt actagtgcca tttgttcagt ggttcgtagg gctttccccc   720
actgtttggc tttcagttat atggatgatg tggtattggg ggccaagtct gtacagcatc   780
ttgagtccct ttttaccgct gttaccaatt ttcttttgtc tttgggtata catttaaacc   840
ctaacaaaac aaaaagatgg ggttactctt tacatttcat gggttatgtc attggatgtt   900

<210> SEQ ID NO 115
<211> LENGTH: 900
<212> TYPE: DNA
<213> ORGANISM: Hepatitis B virus
<300> PUBLICATION INFORMATION:
<308> DATABASE ACCESSION NUMBER: AB205126
<309> DATABASE ENTRY DATE: 2008-11-14
<313> RELEVANT RESIDUES IN SEQ ID NO: (1)..(900)

<400> SEQUENCE: 115
aactccacta ccttccacca aactctgcaa gatcccagag tgagaggcct gtatttccct    60
gctggtggct ccagttcagg aacagtaaac cctgttccga ctactgtctc tcacatatcg   120
tcaatcttct cgaggattgg ggaccctgcg ctgaacatgg agaacatcac atcaggattc   180
ctaggacccc tgctcgtgtt acaggcgggg ttttcttgt tgacaagaat cctcacaata    240
ccgcagagtc tagactcgtg gtggacttct ctcaattttc taggggaac taccgtgtgt    300 cttggccaaa attcgcagtc cccaacctcc aatcactcac caacctcctg tcctccaact   360
tgtcctggtt atcgctggat gtgtctgcgg cgttttatca tcttcctctt catcctgctg   420
ctatgcctca tcttcttgtt ggttcttctg gactatcaag gtatgttgcc cgtttgtcct   480
ctaattccag gatcttcaac taccagcacg ggaccatgca gaacctgcac gactcctgct   540
caaggaacct ctatgtatcc ctcctgctgc tgtaccaaac cttcggacgg aaattgcacc   600
tgtattccca tcccatcatc ctgggctttc ggaaaattcc tatgggagtg gcctcagcc    660 cgtttctcct ggctcagttt actagtgcca tttgttcagt ggttcgtagg gctttccccc   720
actgtttggc tttcagttat atggatgatg tggtattggg ggccaagtct gtacagcatc   780
ttgagtccct ttttaccgct gttaccaatt ttcttttgtc tttgggtata catttaaacc   840
ctaacaaaac aaaaagatgg ggttactctt tacatttcat gggttatgtc attggatgtt   900

<210> SEQ ID NO 116
<211> LENGTH: 900
<212> TYPE: DNA
<213> ORGANISM: Hepatitis B virus
<300> PUBLICATION INFORMATION:
<308> DATABASE ACCESSION NUMBER: AY233291
```

<309> DATABASE ENTRY DATE: 2004-04-23
<313> RELEVANT RESIDUES IN SEQ ID NO: (1)..(900)

<400> SEQUENCE: 116

```
ttccacaacc ttccaccaaa ctctgcaaga tcccagagtg agaggcctgt atttccctgc      60
tggtggctcc agttcaggaa cagtaaaccc tgttccgact actgcctctc ccttatcgtc     120
aatcttctcg aggattgggg accctgcgcc gaacatggag aacatcacat caggattcct     180
aggaccctg ctcgtgttac aggcggggtt tttcttgttg acaagaatcc tcacaatacc     240
gcagagtcta gactcgtggt ggacttctct caattttcta gggggaacta ccgtgtgtct     300
tggccaaaat tcgcagtccc caacctccaa tcactcacca acctcctgtc ctccaacttg     360
tcctggttat cgctggatgt gtctgcggcg ttttatcatc ttcctcttca tcctgctgct     420
atgcctcatc ttcttgttgg ttcttctgga ctatcaaggt atgttgcccg tgtgtcctct     480
aattccagga tcctcaacca ccagcacggg accatgccga acctgcacga ctcctgctca     540
aggaacctct atgtatccct cctgttgctg taccaaacct tcggacggaa attgcacctg     600
tattcccatc ccatcatcct ggcctttcgg aaaattccta tgggagtggg cctcagcccg     660
tttctcctgg ctcagtttac tagtgccatt tgttcagtgg ttcgtagggc tttccccccac     720
tgtttggctt tcagttatat ggatgatgtg gtattggggg ccaagtctgt acagcatctt     780
gagtcccttt ttaccgctgt taccaatttt cttttgtctt tgggtataca tttaaaccct     840
aacaaaacaa agagatgggg ttactctcta aattttatgg ggtatgtcat tggatgttat     900
```

<210> SEQ ID NO 117
<211> LENGTH: 900
<212> TYPE: DNA
<213> ORGANISM: Hepatitis B virus
<300> PUBLICATION INFORMATION:
<308> DATABASE ACCESSION NUMBER: AB048702
<309> DATABASE ENTRY DATE: 2001-03-23
<313> RELEVANT RESIDUES IN SEQ ID NO: (1)..(900)

<400> SEQUENCE: 117

```
ctccacaacc ttccaccaaa ctctgcaaga tcccagagtg agaggcctgt atctccctgc      60
tggtggctcc agttcaggaa cagtaaaccc tgttccgact actgcctctc ccatatcgtc     120
aatcttctcg aggattgggg accttgcgct gaacatggag aacatcacat caggattcct     180
aggaccctg ctcgtgttac aggcggggtt tttcttgttg acaagaatcc tcacaatacc     240
gcagagtcta gactcgtggt ggacttctct caattttcta gggggaacta ccgtgtgtct     300
tggccaaaat tcgcagtccc caacctccaa tcactcacca acctcctgtc ctccaacttg     360
tcctggttat cgctggatgt ttctgcggcg ttttatcatc ttcctcttca tcctgctgct     420
atgcctcatc ttcttgttgg ttcttctgga ttatcaaggt atgttgcccg tttgtcctct     480
aattccagga tcatcaacca ccagcacggg accctgcaga acctgcacga ctcctgctca     540
aggaacctct atgtatccct cctgttgctg tacaaaacct tcggatggaa actgcacctg     600
tattcccatc ccatcatcct gggctttcgg aaaattccta tgggagtggg cctcagcccg     660
tttctcttgg ctcagtttac tagtgccatt tgttcagtgg ttcgtagggc tttccccccac     720
tgtttggctt tcagttatat ggatgatgtg gtattggggg ccaagtctgt acagcacctt     780
gagtcccttt ttaccgctgt taccaatttt cttttgtctt tgggtataca tttaaaccct     840
aacaaaacaa aaagatgggg ttattctcta aatttcatgg ctatgtcat tggaagttgg     900
```

<210> SEQ ID NO 118

<211> LENGTH: 900
<212> TYPE: DNA
<213> ORGANISM: Hepatitis B virus
<300> PUBLICATION INFORMATION:
<308> DATABASE ACCESSION NUMBER: AB205191
<309> DATABASE ENTRY DATE: 2006-01-12
<313> RELEVANT RESIDUES IN SEQ ID NO: (1)..(900)

<400> SEQUENCE: 118

```
ttccacaaca ttccaccaag ctctgcagga tcccagagta agaggcctgt attttcctgc      60
tggtggctcc agttccggaa cagtgaaccc tgttccgact actgcctcac tcatctcgtc     120
aatcttctcg aggattgggg accctgcacc gaacatggaa ggcatcacat caggattcct     180
aggacccctg ctcgtgttac aggcggggtt tttcttgttg acaaaaatcc tcacaatacc     240
gcagagtcta gactcgtggt ggacttctct caattttcta gggggagctc ccgtgtgtct     300
tggccaaaat tcgcagtccc caacctccaa tcactcacca acctcttgtc ctccaatttg     360
tcctggctat cgctggatgt gtctgcggcg ttttatcatc ttcctcttca tcctgctgct     420
atgcctcatc ttcttgttgg ttcttctgga ctatcaaggt atgttgcccg tttgtcctct     480
aattccagga tcatcaacca ccagtacggg accctgccga acctgcacga ctcttgctca     540
aggaacctct atgtttccct catgttgctg ttcaaaacct tcggacggaa attgcacttg     600
tattcccatc ccatcatcat gggctttcgg aaaattccta gggagtgggg cctcagcccg     660
tttctcctgg ctcagtttac tagtgccatt tgttcagtgg ttcgccggc tttccccac      720
tgtctggctt tcagttatat ggatgatgtg gtattggggg ccaagtctgt acaacatctt     780
gagtcccttt ataccgctgt taccaatttt cttttgtctt gggtataca tttaaatcca     840
aacaaaacaa aagatggggg atattcccta aatttcatgg gttatgtaat tggaagttgg     900
```

<210> SEQ ID NO 119
<211> LENGTH: 900
<212> TYPE: DNA
<213> ORGANISM: Hepatitis B virus
<300> PUBLICATION INFORMATION:
<308> DATABASE ACCESSION NUMBER: AY090459
<309> DATABASE ENTRY DATE: 2002-08-07
<313> RELEVANT RESIDUES IN SEQ ID NO: (1)..(900)

<400> SEQUENCE: 119

```
gaactcaact cagttccacc aggctctgtt agatccgagg gtaagggctc tgtattttcc      60
tgctggtggc tccagttcag agacacagaa ccctgctccg actattgcct ctctcacatc     120
atcaatcttc ttgaagactg ggggccctgc tatgaacatg dacaacatca catcaggact     180
cctaggaccc ctgctcgtgt tacaggcggt gtgtttcttg ttgacaaaaa tcctcacaat     240
accacagagt ctagactcgt ggtggacttc tctcaatttt ctagggggaa caccagggtg     300
tcctggccaa aattcgcagt ccccaacctc caatcactta ccaacctcct gtcctccaac     360
ttgtcctggt tatcgctgga tgtgtctgcg gcgttttatc atcttcctct tcatcctgct     420
gctatgcctc atcttcttgt tggttcttct ggactatcaa gtatgttgc cgtttgtcc      480
tctacttcca ggatccacga ccaccagcac gggaccatgc aaaacctgca caactcttgc     540
tcaaggaacc tctatgtttc cctcctgctg ctgttccaaa ccttcggacg aaactgcac      600
ttgtattccc atcccatcat cctgggcttt aggaaaatac ctatgggagt gggcctcagc     660
ccgtttctcc tggctcagtt tactagtgca atttgttcag tggtgcgtag gctttcccc      720
cactgtttgg cttttagtta tatggatgat ctggtattgg gggccaaatc tgtgcagcat     780
cttgagtccc tttataccgc tgttaccaat tttctgttat ctgtgggtat ccatttaaat     840
```

```
acctctaaaa cgaaaagatg gggctatact ttaaatttca tgggatatgt tattggcagt    900
```

<210> SEQ ID NO 120
<211> LENGTH: 900
<212> TYPE: DNA
<213> ORGANISM: Hepatitis B virus
<300> PUBLICATION INFORMATION:
<308> DATABASE ACCESSION NUMBER: AF223963
<309> DATABASE ENTRY DATE: 2001-01-17
<313> RELEVANT RESIDUES IN SEQ ID NO: (1)..(900)

<400> SEQUENCE: 120

```
ctccactcag ttccaccagg ctctgttaga tccgagggta agggctctgt attttcctgc     60
tggtggctcc agttcagaga cacagaaccc tgctccgact attgcctctc tcacatcatc    120
aatcttcttg aagactgggg gccctgctac gaacatggac aacatcacat caggactcct    180
aggacccctg ctcgtgttac aggcggtgtg tttcttgttg acaaaaatcc tcacaatacc    240
acagagtcta gactcgtggt ggacttctct caatttttcta ggggaacac ccgggtgtcc    300
tggccaaaat tcgcagtccc caacctccaa tcacttacca acctcctgtc ctccaacttg    360
tcctggctat cgctggatgt gtctgcggcg ttttatcatc ttcctcttca tcctgctgct    420
atgcctcatc ttcttgttgg ttcttgtgga ctatcaaggt atgttgcccg tttgtcctcc    480
acttccagga tccacgacca ccagcacggg accatgcaaa acctgcacaa ctcttgctca    540
aggaacctct atgtttccct cttgctgctg ttccaaaccc tcggacggaa actgcacttg    600
tattcccatc ccatcatcct gggctttagg aaaataccta tggagtgggg cctcagcccg    660
tttctcctgg ctcagtttac tagtgcaatt tgttcagtgg tgcgtagggc tttcccccac    720
tgtctggctt ttagttatat ggatgatctg gtattggggg ccaaatctgt gcagcatctt    780
gagtcccttt ataccgctgt taccaatttt ctgttatctg tgggtatcca tttaaatacc    840
tcgaaaacaa aaagatgggg ttataccta aatttcatgg gttatgttat tggcagttgg    900
```

<210> SEQ ID NO 121
<211> LENGTH: 900
<212> TYPE: DNA
<213> ORGANISM: Hepatitis B virus
<300> PUBLICATION INFORMATION:
<308> DATABASE ACCESSION NUMBER: AY311369
<309> DATABASE ENTRY DATE: 2006-08-28
<313> RELEVANT RESIDUES IN SEQ ID NO: (1)..(900)

<400> SEQUENCE: 121

```
ctcaacccag ttccaccagg ctctgttgga tcccagggta agggctctgt acttccctgc     60
tggtggctcc agttcaggga cacagaaccc tgctccgact attgcctctc tcacatcatc    120
aatcttctcg aagactgggg gccctgctat gaacatggac aacattacat caggactcct    180
aggacccctg ctcgtgttac aggcggtgtg tttcttgttg acaaaaatcc tcacaatacc    240
acagagtcta gactcgtggt ggacttctct caatttttcta ggggactac ccgggtgtcc    300
tggccaaaat tcgcagtccc caacctccaa tcacttacca acctcctgtc ctccaacttg    360
tcctggctat cgttggatgt gtctgcggcg ttttatcatc ttcctcttca tcctgctgct    420
atgcctcatc ttcttgttgg ttcttctgga ctatcaaggt atgttgcccg tttgtcctct    480
acttccagga tccacgacca ccagcacggg accctgcaaa acctgcacaa ctcttgcaca    540
aggaacctct atgtttccct cctgttgctg ttccaaaccc tcggacggaa actgcacttg    600
tattcccatc ccatcatctt gggctttagg aaaataccta tggagtgggg cctcagcccg    660
```

```
tttctcctgg ctcagtttac tagtgcaatt tgttcagtgg tgcgtcgggc tttcccccac    720
tgtttggctt ttagttatat ggatgatctg gtattggggg ccaaatctgt gcagcatctt    780
gagtcccttt ataccgctgt taccaatttt ctgttatctg tgggtatcca tttaaatacc    840
tctaaaacaa aaagatgggg gtactcccta cattttatgg gctatgtcat tggtagttgg    900
```

<210> SEQ ID NO 122
<211> LENGTH: 900
<212> TYPE: DNA
<213> ORGANISM: Hepatitis B virus
<300> PUBLICATION INFORMATION:
<308> DATABASE ACCESSION NUMBER: AB036915
<309> DATABASE ENTRY DATE: 2001-02-20
<313> RELEVANT RESIDUES IN SEQ ID NO: (1)..(900)

<400> SEQUENCE: 122

```
ctcaacccag ttccaccagg ctctgttaga tccgagggta agggctctgt attttcctgc     60
tggtggctcc agttcaggga cacagaaccc tgttccgact attgcctctc tcacatcatc    120
aatcttctcg aagactgggg gccctgctat gaacatggaa acatcacat caggactcct    180 aggacccctg ctcgtgttac aggcggtgtg tttcttgttg acaaaaatcc tcacaatacc    240
acagagtcta gactcgtggt ggacttctct caattttcta gggggactac ccgggtgtcc    300
tggccaaaat tcgcagtccc caacctccaa tcacttacca acctcctgtc ctccaacttg    360
tcctggctat cgttggatgt gtctgcggcg ttttatcatc ttcctcttca tcctgctgct    420
atgcctcatc ttcttgttgg ttcttctgga ctatcaaggt atgttgcccg tttgtcctct    480
acttccagga tccacaacca ccagcacggg accatgcaaa acctgcacaa ctcttgctca    540
aggaacctct atgtttccct cctgttgctg ttccaaaccc tcggacggaa actgcacctg    600
tattcccatc ccatcatctt gggctttagg aaaataccta tgggagtggg cctcagcccg    660
tttctcctgg ctcagtttac tagtgcaatt tgttcagtgg tgcgtagggc tttcccccac    720
tgtctggctt ttagttatat ggatgatctg gtattggggg ccaaatctgt gcagcatctt    780
gagtcccttt ataccgctgt taccaatttt tgttatctg tgggtatcca tttaaatact    840
tctaaaacaa aaagatgggg ttacaaccta catttcatgg gttatgttat tggtagttgg    900
```

<210> SEQ ID NO 123
<211> LENGTH: 900
<212> TYPE: DNA
<213> ORGANISM: Hepatitis B virus
<300> PUBLICATION INFORMATION:
<308> DATABASE ACCESSION NUMBER: AB166850
<309> DATABASE ENTRY DATE: 2010-02-09
<313> RELEVANT RESIDUES IN SEQ ID NO: (1)..(900)

<400> SEQUENCE: 123

```
ctcaacccag ttccaccagg ccctgttgga tccgagggta agggctctgt ctcctcctgc     60
tggtggctcc agttcagaga cacagaaccc tgctccgact attgcctctc tcacatcatc    120
aatcttctcg aaaactgggg gccctgctat gaacatggac aacatcacat caggactcct    180
aggacccctg ctcgtgttac aggcggtgtg tttcttgttg acaaaaatcc gcacaatacc    240
acagagtcta gacttgtggt ggacttctct caattttcta gggggactac ccgggtgtcc    300
tggccaaaat tcgcagtccc caacctccaa tcacttacca acctcctgtc ctccaacttg    360
tcctggctat cgttggatgt gtctgcggcg ttttatcatc ttcctcttca tcctgctgct    420
atgcctcatc ttcttgttgg ttcttctgga ctatcaaggt atgttgcccg tttgtcctct    480
aattccagga tctacgacca ccagcacggg accatgcaaa acctgcacaa ctcttgctca    540
```

```
aggaacctct atgtttccct cctgttgctg ttcaaaacct tcggacggaa actgcacctg    600
tattcccatc ccatcatctt gggctttagg aaaataccta tggagtgggg cctcagcccg    660
tttctcctgg ctcagtttac tagtgcaatt tgttcagtgg tgcgtagggc tttcccccac    720
tgtctggctt ttagttatat ggatgatctg gtattggggg ccaaatctgt gcagcatctt    780
gagtcccttt ataccgctgt taccaatttt ctgttatctg tgggtatcca tttgaatacc    840
tctaaaacaa aaagatgggg ttacaattta catttcatgg gttatatcat tggtagttgg    900
```

<210> SEQ ID NO 124
<211> LENGTH: 900
<212> TYPE: DNA
<213> ORGANISM: Hepatitis B virus
<300> PUBLICATION INFORMATION:
<308> DATABASE ACCESSION NUMBER: AB064312
<309> DATABASE ENTRY DATE: 2002-06-04
<313> RELEVANT RESIDUES IN SEQ ID NO: (1)..(900)

<400> SEQUENCE: 124

```
ctctacagca ttccaccaag ctctacaaaa tcccacagtc aggggcctgt atcttcctgc     60
tggtggctcc agttcaggga tagtgaaccc tgttccgact attgcctctc acatctcgtc    120
aatcttctcc aggattgggg accctgcacc gaacatggag aacatcacat caggattcct    180
aggacccctg ctcgtgttac aggcggggtt tttcttgttg acaagaatcc tcacaatacc    240
gcagagtcta gactcgtggt ggacttctct caattttcta ggggagtgc ccgtgtgtcc    300 tggcctaaat tcgcagtccc caacctccaa tcactcacca atctcctgtc tccaacttg    360 tcctggctat cgctggatgt gtctgcggcg ttttatcata ttcctcttca tcctgctgct    420
atgcctcatc ttcttgttgg ttcttctgga ctatcaaggt atgttgcccg tttgtcctct    480
gattccagga tcctcgacca ccagtacggg accctgcaaa acctgcacga ctcctgctca    540
aggcaactct atgtatccct catgttgctg tacaaaacct tcggacggaa attgcacctg    600
tattcccatc ccatcatctt gggctttcgc aaaataccta tggagtgggg cctcagtccg    660
tttctcttgg ctcagtttac tagtgccatt tgttcagtgg ttcgtagggc tttcccccac    720
tgtctggctt tcagctatat ggatgatgtg gtattggggg ccaaatctgt acaacatctt    780
gagtcccttt ataccgctgt taccaatttt cttttgtctt tgggtataca tctaaaccct    840
gacaaaacaa aaagatgggg ttattcctta aattttatgg gatatgtaat tggaagttgg    900
```

<210> SEQ ID NO 125
<211> LENGTH: 900
<212> TYPE: DNA
<213> ORGANISM: Hepatitis B virus
<300> PUBLICATION INFORMATION:
<308> DATABASE ACCESSION NUMBER: AB059659
<309> DATABASE ENTRY DATE: 2002-12-04
<313> RELEVANT RESIDUES IN SEQ ID NO: (1)..(900)

<400> SEQUENCE: 125

```
ctcaacacag ttccaccaag cactgttaga tccgagagta aggggtctgt attttcctgc     60
tggtggctcc agttcagaaa cacagaaccc tgctccgact attgcctctc tcacatcatc    120
aatcttctcg aagactgggg accctgctat gaacatggag aacatcacat caggactcct    180
aggacccctt cccgtgttac agggggtgtt tttctcgttg acaaaaatcc tcacaatacc    240
acagagtcta gactcgtggt ggacttctct caattttcta gaggtaccac ccgggtgtcc    300
tggccaaaat tcgcagtccc caatctccaa tcacttacca acctcctgtc tccaacttg    360
```

```
tcctggctat cgttggatgt gtctgcggcg ttttatcatc ttcctcttca tcctgctgct    420
atgcctcatc ttcttgttgg ttcttctgga ctatcaaggt atgttgcccg tgtgtcctct    480
acttccagga tctacaacca ccagcacggg accctgcaaa acctgcacca ctcttgctca    540
aggaacctct atgtttccct cctgctgctg taccaaacct tcggacggaa attgcacctg    600
tattcccatc ccatcatctt gggctttcgg aaaatacctg tgggagtggg cctcagcccg    660
tttctcttgg ctcagtttac tagtgcaatt tgttcagtgg tgcgtagggc ttcccccac    720 tgtctggctt ttagttatat ggatgatttg gtattggggg ccaaatctgt gcagcatctt    780
gagtcccttt ataccgctgt taccaatttt ttgttatctg tgggcatcca tttgaacaca    840
gctaaaacaa aaggtgggg ttattcctta cactttatgg gttatataat tgggagttgg    900

<210> SEQ ID NO 126
<211> LENGTH: 66
<212> TYPE: DNA
<213> ORGANISM: Hepatitis B virus

<400> SEQUENCE: 126
tcgtagggct ttcccccact gtttggcttt cagctatatg gatgatgtgg tattgggggc    60
caagtc                                                               66

<210> SEQ ID NO 127
<211> LENGTH: 66
<212> TYPE: DNA
<213> ORGANISM: Hepatitis B virus

<400> SEQUENCE: 127
tcgtagggct ttcccccact gtttggcttt cagctatatg gatgatgtgg tattgggggc    60
caagtc                                                               66

<210> SEQ ID NO 128
<211> LENGTH: 66
<212> TYPE: DNA
<213> ORGANISM: Hepatitis B virus

<400> SEQUENCE: 128
tcgtagggct ttcccccact gtctggcttt cagttatatg gatgatgtgg ttttgggggc    60
caagtc                                                               66

<210> SEQ ID NO 129
<211> LENGTH: 66
<212> TYPE: DNA
<213> ORGANISM: Hepatitis B virus

<400> SEQUENCE: 129
tcgtagggct ttcccccact gtttggcttt cagttatatg gatgatgtgg tattgggggc    60
caagtc                                                               66

<210> SEQ ID NO 130
<211> LENGTH: 66
<212> TYPE: DNA
<213> ORGANISM: Hepatitis B virus

<400> SEQUENCE: 130
tcgtagggct ttcccccact gtttggcttt cagttatatg gatgatgtgg tattgggggc    60
caagtc                                                               66
```

```
<210> SEQ ID NO 131
<211> LENGTH: 66
<212> TYPE: DNA
<213> ORGANISM: Hepatitis B virus

<400> SEQUENCE: 131
tcgtagggct tccccccact gtttggcttt cagttatatg gatgatgtgg tattgggggc   60
caagtc                                                             66

<210> SEQ ID NO 132
<211> LENGTH: 66
<212> TYPE: DNA
<213> ORGANISM: Hepatitis B virus

<400> SEQUENCE: 132
tcgccgggct tccccccact gtctggcttt cagttatatg gatgatgtgg tattgggggc   60
caagtc                                                             66

<210> SEQ ID NO 133
<211> LENGTH: 66
<212> TYPE: DNA
<213> ORGANISM: Hepatitis B virus

<400> SEQUENCE: 133
gcgtagggct tccccccact gtctggcttt tagttatatg gatgatctgg tattgggggc   60
caaatc                                                             66

<210> SEQ ID NO 134
<211> LENGTH: 66
<212> TYPE: DNA
<213> ORGANISM: Hepatitis B virus

<400> SEQUENCE: 134
tcgtagggct tccccccact gtctggcttt cagctatgtg gatgatgtgg tattgggggc   60
caaatc                                                             66

<210> SEQ ID NO 135
<211> LENGTH: 66
<212> TYPE: DNA
<213> ORGANISM: Hepatitis B virus

<400> SEQUENCE: 135
gcgtagggct tccccccact gtctggcttt tagttatatg gatgatttgg tattgggggc   60
caaatc                                                             66

<210> SEQ ID NO 136
<211> LENGTH: 34
<212> TYPE: DNA
<213> ORGANISM: Hepatitis B virus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 136
gsngyttgtt ttgctcgcag ccggtctgga gcnv                              34

<210> SEQ ID NO 137
```

```
<211> LENGTH: 34
<212> TYPE: DNA
<213> ORGANISM: Hepatitis B virus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 137
rcngcttgtt ttgctcgcag caggtctgga gcnm                              34

<210> SEQ ID NO 138
<211> LENGTH: 34
<212> TYPE: DNA
<213> ORGANISM: Hepatitis B virus
<220> FEATURE:
<221> NAME/KEY: misc_feature
<222> LOCATION: (3)..(3)
<223> OTHER INFORMATION: n is a, c, g, or t

<400> SEQUENCE: 138
gcngyttgtt ttgctcgcag caggtctggg gcdm                              34

<210> SEQ ID NO 139
<211> LENGTH: 34
<212> TYPE: DNA
<213> ORGANISM: Hepatitis B virus
<220> FEATURE:
<221> NAME/KEY: misc_feature
<222> LOCATION: (3)..(3)
<223> OTHER INFORMATION: n is a, c, g, or t

<400> SEQUENCE: 139
gcngcttgtt ttgctcgcag ccggtctggg gcra                              34

<210> SEQ ID NO 140
<211> LENGTH: 34
<212> TYPE: DNA
<213> ORGANISM: Hepatitis B virus
<220> FEATURE:
<221> NAME/KEY: misc_feature
<222> LOCATION: (3)..(3)
<223> OTHER INFORMATION: n is a, c, g, or t

<400> SEQUENCE: 140
gcngcttgtt tcgctcgcag ccggtctgga gcrv                              34

<210> SEQ ID NO 141
<211> LENGTH: 34
<212> TYPE: DNA
<213> ORGANISM: Hepatitis B virus

<400> SEQUENCE: 141
gcmgcttgct ttgctcgcag caggtctgga gcra                              34

<210> SEQ ID NO 142
<211> LENGTH: 34
<212> TYPE: DNA
<213> ORGANISM: Hepatitis B virus
<220> FEATURE:
<221> NAME/KEY: misc_feature
<222> LOCATION: (3)..(3)
<223> OTHER INFORMATION: n is a, c, g, or t

<400> SEQUENCE: 142
```
gcngcctgtt ttgctcgcag ccggtctgga gcdr    34

<210> SEQ ID NO 143
<211> LENGTH: 34
<212> TYPE: DNA
<213> ORGANISM: Hepatitis B virus
<220> FEATURE:
<221> NAME/KEY: misc_feature
<222> LOCATION: (1)..(34)
<223> OTHER INFORMATION: "N" marks the absence of a nucleotide (i.e., a deletion).

<400> SEQUENCE: 143
nnnnnnnnnn nnnnnnnnnn nnnnnnnnnn nnnn    34

<210> SEQ ID NO 144
<211> LENGTH: 34
<212> TYPE: DNA
<213> ORGANISM: Hepatitis B virus

<400> SEQUENCE: 144
gcvgcttgtt tcgctcgcag caggtctgga gcgr    34

<210> SEQ ID NO 145
<211> LENGTH: 34
<212> TYPE: DNA
<213> ORGANISM: Hepatitis B virus

<400> SEQUENCE: 145
gcagcctgtt tcgctcgcag ccggtctgga gcga    34

<210> SEQ ID NO 146
<211> LENGTH: 27
<212> TYPE: DNA
<213> ORGANISM: Hepatitis B virus

<400> SEQUENCE: 146
gtctgtgcca agtgtttgct gacgctt    27

<210> SEQ ID NO 147
<211> LENGTH: 30
<212> TYPE: DNA
<213> ORGANISM: Hepatitis B virus
<220> FEATURE:
<221> NAME/KEY: misc_feature
<222> LOCATION: (2)..(2)
<223> OTHER INFORMATION: n is a, c, g, or t

<400> SEQUENCE: 147
hnrgtctgtg ccaagtgttt gctgacgcaa    30

<210> SEQ ID NO 148
<211> LENGTH: 30
<212> TYPE: DNA
<213> ORGANISM: Hepatitis B virus
<220> FEATURE:
<221> NAME/KEY: misc_feature
<222> LOCATION: (2)..(2)
<223> OTHER INFORMATION: n is a, c, g, or t

<400> SEQUENCE: 148
cnrgtctctg ccaagtgttt gctgacgcva    30

<210> SEQ ID NO 149
<211> LENGTH: 30

<212> TYPE: DNA
<213> ORGANISM: Hepatitis B virus
<220> FEATURE:
<221> NAME/KEY: misc_feature
<222> LOCATION: (2)..(2)
<223> OTHER INFORMATION: n is a, c, g, or t

<400> SEQUENCE: 149
cnrgtctgtg ccaagtgttt gctgatgcaa                              30

<210> SEQ ID NO 150
<211> LENGTH: 30
<212> TYPE: DNA
<213> ORGANISM: Hepatitis B virus
<220> FEATURE:
<221> NAME/KEY: misc_feature
<222> LOCATION: (2)..(2)
<223> OTHER INFORMATION: n is a, c, g, or t

<400> SEQUENCE: 150
cnggtctttg ccaagtgttt gctgacgcaa                              30

<210> SEQ ID NO 151
<211> LENGTH: 30
<212> TYPE: DNA
<213> ORGANISM: Hepatitis B virus
<220> FEATURE:
<221> NAME/KEY: misc_feature
<222> LOCATION: (2)..(2)
<223> OTHER INFORMATION: n is a, c, g, or t

<400> SEQUENCE: 151
cnggtctatg ccaagtgttt gctgacgcaa                              30

<210> SEQ ID NO 152
<211> LENGTH: 30
<212> TYPE: DNA
<213> ORGANISM: Hepatitis B virus

<400> SEQUENCE: 152
cdggcctgtg ccaagtgttt gctgacgcaa                              30

<210> SEQ ID NO 153
<211> LENGTH: 30
<212> TYPE: DNA
<213> ORGANISM: Hepatitis B virus
<220> FEATURE:
<221> NAME/KEY: misc_feature
<222> LOCATION: (1)..(30)
<223> OTHER INFORMATION: "N" marks the absence of a nucleotide (i.e., a
      deletion).

<400> SEQUENCE: 153
nnnnnnnnnn nnnnnnnnnn nnnnnnnnnn                              30

<210> SEQ ID NO 154
<211> LENGTH: 30
<212> TYPE: DNA
<213> ORGANISM: Hepatitis B virus

<400> SEQUENCE: 154
cwggtctctg ccaagtgttt gctgatgcra                              30

<210> SEQ ID NO 155
<211> LENGTH: 30
<212> TYPE: DNA
<213> ORGANISM: Hepatitis B virus

```
<400> SEQUENCE: 155
cmggtctatg ccaagtgttt gctgatgcaa                                       30

<210> SEQ ID NO 156
<211> LENGTH: 30
<212> TYPE: DNA
<213> ORGANISM: Hepatitis B virus

<400> SEQUENCE: 156
chggtgtctg ccaagtgttt gctgacgcaa                                       30

<210> SEQ ID NO 157
<211> LENGTH: 132
<212> TYPE: DNA
<213> ORGANISM: Hepatitis B virus

<400> SEQUENCE: 157
actcaccaac ctcctgtcct ccaatttgtc ctggttatcg ctggatgtgt ctgcggcgtt      60
ttatcatatt cctcttcatc ctgctgctat gcctcatctt cttattggtt cttctggatt    120
atcaaggtat gt                                                         132

<210> SEQ ID NO 158
<211> LENGTH: 132
<212> TYPE: DNA
<213> ORGANISM: Hepatitis B virus

<400> SEQUENCE: 158
actcaccaac ctcctgtcct ccaatttgtc ctggctatcg ctggatgtgt ctgcggcgtt      60
ttatcatatt cctcttcatc ctgctgctat gcctcatctt cttattggtt cttctggatt    120
atcaaggtat gt                                                         132

<210> SEQ ID NO 159
<211> LENGTH: 132
<212> TYPE: DNA
<213> ORGANISM: Hepatitis B virus

<400> SEQUENCE: 159
actcaccaac ttgttgtcct ccgatttgtc ctggttatcg ctggatgtgt ctgcggcgtt      60
ttatcatctt cctctgcatc ctgctgctat gcctcatctt cttgttggtt cttctggact    120
atcaaggtat gt                                                         132

<210> SEQ ID NO 160
<211> LENGTH: 132
<212> TYPE: DNA
<213> ORGANISM: Hepatitis B virus

<400> SEQUENCE: 160
actcaccaac ctcttgtcct ccaatttgtc ctggctatcg ctggatgtgt ctgcggcgtt      60
ttatcatctt cctcttcatc ctgctgctat gcctcatctt cttgttggtt cttctggact    120
accaaggtat gt                                                         132

<210> SEQ ID NO 161
<211> LENGTH: 132
<212> TYPE: DNA
<213> ORGANISM: Hepatitis B virus

<400> SEQUENCE: 161
```

```
actcaccaac ctcttgtcct ccaatttgtc ctggctatcg ttggatgtgt ctgcggcgtt    60
ttatcatatt cctcttcatc ctgctgctat gcctcatctt cttgttggtt cttctggact   120
accaaggtat gt                                                       132
```

<210> SEQ ID NO 162
<211> LENGTH: 132
<212> TYPE: DNA
<213> ORGANISM: Hepatitis B virus

<400> SEQUENCE: 162

```
actcaccaac ctcctgtcct ccaacttgtc ctggttatcg ctggatgtgt ctgcggcgtt    60
ttatcatctt cctcttcatc ctgctgctat gcctcatctt cttgttggtt cttctggact   120
atcaaggtat gt                                                       132
```

<210> SEQ ID NO 163
<211> LENGTH: 132
<212> TYPE: DNA
<213> ORGANISM: Hepatitis B virus

<400> SEQUENCE: 163

```
actcaccaac ctcttgtcct ccaacttgtc ctggctatcg ctggatgtgt ctgcggcgtt    60
ttatcatctt cctcttcatc ctgctgctat gcctcatctt cttgttggtt cttctggact   120
atcaaggtat gt                                                       132
```

<210> SEQ ID NO 164
<211> LENGTH: 132
<212> TYPE: DNA
<213> ORGANISM: Hepatitis B virus

<400> SEQUENCE: 164

```
acttaccaac ctcctgtcct ccaacttgtc ctggctatcg ctggatgtgt ctgcggcgtt    60
ttatcatctt cctcttcatc ctgctgctat gcctcatctt cttgttggtt cttctggact   120
atcaaggtat gt                                                       132
```

<210> SEQ ID NO 165
<211> LENGTH: 132
<212> TYPE: DNA
<213> ORGANISM: Hepatitis B virus

<400> SEQUENCE: 165

```
actcactaat ctcctgtcct ccaacttgtc ctggctatcg ctggatgtgt ctgcggcgtt    60
ttatcatatt cctcttcatc ctgctgctat gcctcatctt cttgttggtt cttctggact   120
atcaaggtat gt                                                       132
```

<210> SEQ ID NO 166
<211> LENGTH: 132
<212> TYPE: DNA
<213> ORGANISM: Hepatitis B virus

<400> SEQUENCE: 166

```
acttaccaac ctcctgtcct ccaacttgtc ctggctatcg ttggatgtgt ctgcggcgtt    60
ttatcatctt cctcttcatc ctgctgctat gcctcatctt cttgttggtt cttctggact   120
atcaaggtar gt                                                       132
```

<210> SEQ ID NO 167
<211> LENGTH: 102

<212> TYPE: DNA
<213> ORGANISM: Hepatitis B virus

<400> SEQUENCE: 167
gcagtcccca acctccaatc actcaccaac ctcctgtcct ccaatttgtc ctggctatcg    60
ctggatgtgt ctgcggcgtt ttatcatatt cctcttcatc ct                     102

<210> SEQ ID NO 168
<211> LENGTH: 102
<212> TYPE: DNA
<213> ORGANISM: Hepatitis B virus

<400> SEQUENCE: 168
gcagtcccaa atctccagtc actcaccaac ttgttgtcct ccgatttgtc ctggttatcg    60
ctggatgtgt ctgcggcgtt ttatcatctt cctctgcatc ct                     102

<210> SEQ ID NO 169
<211> LENGTH: 102
<212> TYPE: DNA
<213> ORGANISM: Hepatitis B virus

<400> SEQUENCE: 169
gcagtcccca acctccaatc actcaccaac ctcttgtcct ccaatttgtc ctggctatcg    60
ctggatgtgt ctgcggcgtt ttatcatctt cctcttcatc ct                     102

<210> SEQ ID NO 170
<211> LENGTH: 102
<212> TYPE: DNA
<213> ORGANISM: Hepatitis B virus

<400> SEQUENCE: 170
gcagtcccca acctccaatc actcaccaac ctcttgtcct ccaatttgtc ctggctatcg    60
ttggatgtgt ctgcggcgtt ttatcatatt cctcttcatc ct                     102

<210> SEQ ID NO 171
<211> LENGTH: 102
<212> TYPE: DNA
<213> ORGANISM: Hepatitis B virus

<400> SEQUENCE: 171
gcagtcccca acctccaatc actcaccaac ctcctgtcct ccaacttgtc ctggttatcg    60
ctggatgtgt ctgcggcgtt ttatcatctt cctcttcatc ct                     102

<210> SEQ ID NO 172
<211> LENGTH: 102
<212> TYPE: DNA
<213> ORGANISM: Hepatitis B virus

<400> SEQUENCE: 172
gcagtcccca acctccaatc actcaccaac ctcttgtcct ccaacttgtc ctggctatcg    60
ctggatgtgt ctgcggcgtt ttatcatctt cctcttcatc ct                     102

<210> SEQ ID NO 173
<211> LENGTH: 102
<212> TYPE: DNA
<213> ORGANISM: Hepatitis B virus

<400> SEQUENCE: 173
gcagtcccca acctccaatc acttaccaac ctcctgtcct ccaacttgtc ctggctatcg    60

```
ctggatgtgt ctgcggcgtt ttatcatctt cctcttcatc ct                  102
```

<210> SEQ ID NO 174
<211> LENGTH: 102
<212> TYPE: DNA
<213> ORGANISM: Hepatitis B virus

<400> SEQUENCE: 174

```
gcagtcccca acctccaatc actcactaat ctcctgtcct ccaacttgtc ctggctatcg   60
ctggatgtgt ctgcggcgtt ttatcatatt cctcttcatc ct                    102
```

<210> SEQ ID NO 175
<211> LENGTH: 102
<212> TYPE: DNA
<213> ORGANISM: Hepatitis B virus

<400> SEQUENCE: 175

```
gcagtcccca atctccaatc acttaccaac ctcctgtcct ccaacttgtc ctggctatcg   60
ttggatgtgt ctgcggcgtt ttatcatctt cctcttcatc ct                    102
```

<210> SEQ ID NO 176
<211> LENGTH: 102
<212> TYPE: DNA
<213> ORGANISM: Hepatitis B virus

<400> SEQUENCE: 176

```
gcagtcccca acctccaatc actcaccaac ctcctgtcct ccaacttgtc ctggttatcg   60
ctggatgtgt gtgctgcgcg gcatcatatt actcttcctc tt                    102
```

<210> SEQ ID NO 177
<211> LENGTH: 147
<212> TYPE: DNA
<213> ORGANISM: Hepatitis B virus

<400> SEQUENCE: 177

```
cagtccccaa cctccaatca ctcaccaacc tcctgtcctc caatttgtcc tggttatcgc   60
tggatgtgtc tgcggcgttt tatcatattc ctcttcatcc tgctgctatg cctcatcttc  120
ttattggttc ttctggatta tcaaggt                                     147
```

<210> SEQ ID NO 178
<211> LENGTH: 39
<212> TYPE: DNA
<213> ORGANISM: Hepatitis B virus

<400> SEQUENCE: 178

```
cagcccatct tcttgttggt tcttctggac tatcaaggt                         39
```

<210> SEQ ID NO 179
<211> LENGTH: 20
<212> TYPE: DNA
<213> ORGANISM: Hepatitis B virus

<400> SEQUENCE: 179

```
aaacaagtca ccaagcgtcc                                              20
```

<210> SEQ ID NO 180
<211> LENGTH: 197
<212> TYPE: DNA
<213> ORGANISM: Hepatitis B virus

<400> SEQUENCE: 180

```
gtattcccat cccatcgtcc tgggctttcg caaaatacct atgggagtgg gcctcagtcc    60
gtttctcttg gctcagttta ctagtgccat ttgttcagtg gttcgtaggg ctttccccca   120
ctgtttggct ttcagctata tggatgatgt ggtattgggg gccaagtctg tacagcatcg   180
tgagtccctt tataccg                                                  197
```

\<210\> SEQ ID NO 181
\<211\> LENGTH: 197
\<212\> TYPE: DNA
\<213\> ORGANISM: Hepatitis B virus

\<400\> SEQUENCE: 181

```
gtattcccat cccatcgtcc tgggctttcg caaaatacct atgggagtgg gcctcagtcc    60
gtttctcttg gctcagttta ctagtgccat ttgttcagtg gttcgtaggg ctttccccca   120
ctgtttggct ttcagctata tggatgatgt ggtattgggg gccaagtctg tacagcatcg   180
tgagtccctt tataccg                                                  197
```

\<210\> SEQ ID NO 182
\<211\> LENGTH: 197
\<212\> TYPE: DNA
\<213\> ORGANISM: Hepatitis B virus

\<400\> SEQUENCE: 182

```
gtattcccat cccatcatct tgggctttcg caaaatacct atgggagtgg gcctcagtcc    60
gtttctcttg gctcagttta ctagtgccat ttgttcagtg gttcgtaggg ctttccccca   120
ctgtctggct ttcagttata tggatgatgt ggttttgggg gccaagtctg tacaacatct   180
tgagtccctt tatgccg                                                  197
```

\<210\> SEQ ID NO 183
\<211\> LENGTH: 197
\<212\> TYPE: DNA
\<213\> ORGANISM: Hepatitis B virus

\<400\> SEQUENCE: 183

```
gtattcccat cccatcatcc tgggctttcg caagattcct atgggagtgg gcctcagtcc    60
gtttctcctg gctcagttta ctagtgccat ttgttcagtg gttcgtaggg ctttccccca   120
ctgtttggct ttcagttata tggatgatgt ggtattgggg gccaagtctg tacaacatct   180
tgagtccctt tttacct                                                  197
```

\<210\> SEQ ID NO 184
\<211\> LENGTH: 197
\<212\> TYPE: DNA
\<213\> ORGANISM: Hepatitis B virus

\<400\> SEQUENCE: 184

```
gtattcccat cccatcatct tgggctttcg caagattcct atgggagtgg gcctcagtcc    60
gtttctcctg gctcagttta ctagtgccat ttgttcagtg gttcgtaggg ctttccccca   120
ctgtttggct ttcagttata tggatgatgt ggtattgggg gccaagtctg tacaacatct   180
tgagtccctt tttacct                                                  197
```

\<210\> SEQ ID NO 185
\<211\> LENGTH: 197
\<212\> TYPE: DNA
\<213\> ORGANISM: Hepatitis B virus

<400> SEQUENCE: 185

```
gtattcccat cccatcatcc tgggctttcg gaaaattcct atgggagtgg gcctcagccc      60
gtttctcctg gctcagttta ctagtgccat tgttcagtg gttcgtaggg ctttccccca     120
ctgtttggct ttcagttata tggatgatgt ggtattgggg gccaagtctg tatcgcatct    180
tgagtccctt tttaccg                                                   197
```

<210> SEQ ID NO 186
<211> LENGTH: 197
<212> TYPE: DNA
<213> ORGANISM: Hepatitis B virus

<400> SEQUENCE: 186

```
gtattcccat cccatcatca tgggctttcg gaaaattcct atgggagtgg gcctcagccc      60
gtttctcctg gctcagttta ctagtgccat tgttcagtg gttcgccggg ctttccccca     120
ctgtctggct ttcagttata tggatgatgt ggtattgggg gccaagtctg tacaacatct    180
tgagtccctt tatacct                                                   197
```

<210> SEQ ID NO 187
<211> LENGTH: 197
<212> TYPE: DNA
<213> ORGANISM: Hepatitis B virus

<400> SEQUENCE: 187

```
gtattcccat cccatcatcc tgggctttag gaaaataacct atgggagtgg gcctcagccc     60
gtttctcctg gctcagttta ctagtgcaat tgttcagtg gtgcgtaggg ctttccccca     120
ctgtctggct tttagttata tggatgatct ggtattgggg gccaaatctg tgcagcatct    180
tgagtccctt tataccg                                                   197
```

<210> SEQ ID NO 188
<211> LENGTH: 197
<212> TYPE: DNA
<213> ORGANISM: Hepatitis B virus

<400> SEQUENCE: 188

```
gtattcccat cccatcatct tgggctttcg caaaattcct atgggagtgg gcctcagtcc      60
gtttctcatg gctcagttta ctagtgccat tgttcagtg gttcgtaggg ctttccccca     120
ctgtctggct ttcagctatg tggatgatgt ggtattgggg gccaaatctg tacaacatct    180
tgagtccctt tataccg                                                   197
```

<210> SEQ ID NO 189
<211> LENGTH: 197
<212> TYPE: DNA
<213> ORGANISM: Hepatitis B virus

<400> SEQUENCE: 189

```
gtattcccat cccatcatct tgggctttcg gaaaataacct atgggagtgg gcctcagccc     60
gtttctcttg gctcagttta ctagtgcaat tgttcagtg gtgcgtaggg ctttccccca     120
ctgtctggct tttagttata tggatgattt ggtattgggg gccaaatctg tgcagcatct    180
tgagtccctt tataccg                                                   197
```

<210> SEQ ID NO 190
<211> LENGTH: 12
<212> TYPE: RNA
<213> ORGANISM: Hepatitis B virus

```
<220> FEATURE:
<221> NAME/KEY: misc_feature
<222> LOCATION: (7)..(8)
<223> OTHER INFORMATION: Non-nucleotide c9 linker inserted between base
      positions 7-8

<400> SEQUENCE: 190
aggaugagug gg                                                         12

<210> SEQ ID NO 191
<211> LENGTH: 23
<212> TYPE: DNA
<213> ORGANISM: Hepatitis B virus

<400> SEQUENCE: 191
ggcacctagt ccagaagaac caa                                             23
```